US012214197B2

(12) United States Patent
ÓLaighin et al.

(10) Patent No.: US 12,214,197 B2
(45) Date of Patent: Feb. 4, 2025

(54) APPARATUS FOR MANAGEMENT OF A PARKINSON'S DISEASE PATIENT'S GAIT

(71) Applicant: NATIONAL UNIVERSITY OF IRELAND, GALWAY, Galway (IE)

(72) Inventors: Gearóid Ó Laighin, Galway (IE); Leo Quinlan, County Galway (IE); Dean Sweeney, County Donegal (IE); Gavin Corley, County Clare (IE); James Feehilly, Galway (IE); Patrick Browne, County Galway (IE)

(73) Assignee: National University of Ireland, Galway, Galway (IE)

( * ) Notice: Subject to any disclaimer, the term of this patent is extended or adjusted under 35 U.S.C. 154(b) by 314 days.

(21) Appl. No.: 17/535,920

(22) Filed: Nov. 26, 2021

(65) Prior Publication Data

US 2022/0118256 A1 Apr. 21, 2022

Related U.S. Application Data

(63) Continuation-in-part of application No. 16/938,606, filed on Jul. 24, 2020, now Pat. No. 11,672,984,
(Continued)

(30) Foreign Application Priority Data

Apr. 17, 2015 (EP) ..................... 15163987

(51) Int. Cl.
*A61N 1/36* (2006.01)
*A61H 3/00* (2006.01)

(52) U.S. Cl.
CPC ........... *A61N 1/36067* (2013.01); *A61H 3/00* (2013.01); *A61N 1/36003* (2013.01);
(Continued)

(58) Field of Classification Search
CPC .. A61N 1/36067; A61N 1/36003; A61H 3/00; A61H 2003/007; A61H 2201/165;
(Continued)

(56) References Cited

U.S. PATENT DOCUMENTS

| 7,917,225 B2 | 3/2011 | Wyler et al. |
| 2004/0082979 A1 | 4/2004 | Tong et al. |

(Continued)

FOREIGN PATENT DOCUMENTS

| EP | 1 558 333 A1 | 8/2005 |
| EP | 2 586 489 B1 | 12/2014 |
| WO | 2004/037344 A1 | 5/2004 |

OTHER PUBLICATIONS

International Search Report issued in PCT/EP2016/058341; mailed Jun. 15, 2016.
(Continued)

*Primary Examiner* — Paula J Stice
(74) *Attorney, Agent, or Firm* — Studebaker & Brackett PC

(57) ABSTRACT

A gait management apparatus applies stimulation to a user suffering from a neurological disease (such as Parkinson's Disease) gait dysfunction. Motion sensors are arranged to be worn by a patient, and electrical stimulation electrodes are on the legs for stimulation. A controller receives motion sensing signals, and processes these signals to generate stimulation signals for operation of the electrodes to stimulate limb movement upon detection of a gait abnormality. There may be a user actuator for user actuation of electrical stimulation, and the inputs may be a series of taps. The controller may provide signals to prevent occurrence of freezing of gait when it senses that a patient is walking or has an intention to walk. Also, it may apply stimulation at an intensity level which is insufficient for functional muscle
(Continued)

stimulation but sufficiently high to trigger activation of efferent nerves.

12 Claims, 33 Drawing Sheets

Related U.S. Application Data which is a continuation of application No. 15/566,967, filed as application No. PCT/EP2016/058341 on Apr. 15, 2016, now Pat. No. 10,744,324.

(52) U.S. Cl.
CPC .. *A61H 2003/007* (2013.01); *A61H 2201/165* (2013.01); *A61H 2201/5023* (2013.01); *A61H 2201/5079* (2013.01); *A61H 2201/5084* (2013.01); *A61H 2230/105* (2013.01)

(58) Field of Classification Search
CPC .... A61H 2201/5023; A61H 2201/5079; A61H 2201/5084; A61H 2230/105
See application file for complete search history.

(56) References Cited

U.S. PATENT DOCUMENTS

| | | |
|---|---|---|
| 2007/0250134 A1 | 10/2007 | Miesel et al. |
| 2008/0208288 A1 | 8/2008 | Gesotti |
| 2009/0099627 A1 | 4/2009 | Molnar et al. |
| 2013/0053734 A1* | 2/2013 | Barriskill ............ A61H 1/0229 601/5 |
| 2013/0171599 A1 | 7/2013 | Bleich et al. |
| 2014/0163444 A1* | 6/2014 | Ingvarsson ........ A61N 1/36003 602/2 |
| 2014/0249452 A1 | 9/2014 | Marsh et al. |
| 2014/0249600 A1 | 9/2014 | Heruth et al. |

OTHER PUBLICATIONS

International Preliminary Report On Patentability issued in PCT/EP2016/058341; mailed Oct. 17, 2017.
Ahlrichs et al., "Detecting Freezing of Gait With a Tri-axial Accelerometer in Parkinson's Disease Patients," Med. Biol., Eng. Compu. (2016) 54:223-233.
Perez-Lopez et al., Dopaminergic-induced Dyskinesia Assessment Based on a Single Belt-Worn Accelerometer, Artificial Intelligence in Medicine, 67 (2016) 47-56.

* cited by examiner

APPARATUS FOR MANAGEMENT OF A PARKINSON'S DISEASE PATIENT'S GAIT

FIELD OF THE INVENTION

The invention relates to the management of gait for persons suffering from Parkinson's disease or with similar neurological conditions.

PRIOR ART DISCUSSION

Parkinson's disease ("PD") is a progressive neurological condition resulting from the loss of dopaminergic neurons in a specialized area of the brain called the substantia nigra. PD can present at any age, however less than 10% of cases are reported before the age of 40. The annual incidence of PD in Europe is 10-20 cases/100,000 inhabitants/year. Approximately 1.6% of people aged over 65 years have PD. There are approximately 5.2 million PD patients worldwide and they have a mortality that is 2 to 5 times higher than age-matched controls. The majority of PD patients are elderly people and this population cohort is expanding rapidly. Thus PD is becoming an increasing public health and socioeconomic challenge. The primary issues in PD are due to reduced capacity for self-care, performance of activities of daily living and reduced quality of life. The high healthcare costs involved with PD (medical and social) are considerable and affect multiple sectors. The main elements of this cost base are hospital care and prescription drugs. PD patients have 45% more hospitalizations and typically stay 20% longer in hospital than disease free age-matched populations.

Gait disturbances are a common feature of neurological disease. Particularly in people with Parkinson's disease, gait disturbances have a significant impact on daily life and often lead to falls and hospitalisation.

Human gait is a cyclic phenomenon of limb repeating movements which we refer to as the human gait cycle. In describing human gait, it is typical to look at the activity of one leg over one cycle, called the Gait Cycle.

Progression during a gait cycle is expressed as a percentage of the Gait Cycle, where 0% is the beginning of the gait cycle (which could be marked by an initial Contact or heel strike) and 100% is the end of the gait cycle (which could be the next initial contact or heel strike). The time to complete one Gait Cycle is referred to as the "Stride Time" or "Gait Cycle Time". The Stride Time for a leg (left or right) is often measured from one heel strike event for that leg (also called initial contact) to the next heel strike for the same leg. A typical value for a healthy human stride time is 1 s. There can be some difference between the left and right leg Stride Time and during walking and there can be some variability in Stride Time from stride to stride.

The Step Time for a leg (left or right) is often measured from one heel strike event for that leg to the next heel strike for the contralateral (other) leg. A typical value for a healthy human Step Time is 0.5 s. There can be some difference between the left and right leg Step Time and during walking there can be some variability in Step Time from step to step.

During gait, each leg goes through two main phases, which are continuously repeated. The phases are:
  The stance phase, where the foot of that leg is in contact with the ground. The stance phase commences at the heel-strike event for that leg (also called initial contact) which is the 0% point of the Gait Cycle and ends at the toe-off event for that leg. Typically, the stance phase duration is 60% of the Gait Cycle; and
  The swing phase, where that leg is swinging through the air to aid progression, the swing phase commences at the toe-off event for that leg and ends at the heel-strike event for the same leg. Typically, the swing phase duration is 40% of the Gait Cycle.

The left and right legs each have swing phases, which are out-of-phase with each other and the left and right leg each have stance phases, which are also out-of-phase with each other.

The symptoms of PD can be broadly classified into motor symptoms and non-motor symptoms.

Motor symptoms (MS) include rigidity, tremor, bradykinesia (slow movement) and postural alterations. These symptoms are cardinal features of PD and contribute to progressive gait disturbances, which are strongly linked to a reduced quality of life. These gait disturbances present in terms of a reduction in stride length and walking speed, increased stride variability and episodes called Freezing Of Gait (FOG). Gait alterations in PD become increasingly problematic as the disease advances despite best pharmacological therapy. In particular, FOG occurs in excess of 40% of PD patients and is characterized by a rapid onset and variable duration (typically <1 min) causing a breakdown in gait fluency. FOG can appear in the initiation of gait or randomly within the gait cycle and is often medication refractory leading to it being a major source of disability for PD patients. FOG can affect people both in the so-called "ON" state (i.e. on normal prescribed medications and the medication effects of the medications are still present) and in the so called "OFF" state (i.e. where the effect of normal medication has worn off).

The biological mechanisms underlying FOG are yet to be elucidated. The most common forms of FOG are reported to be initiation FOG or turning FOG. Attempting to walk in narrow passageways, adjusting one's stride length when reaching a destination, and stressful situations also commonly trigger FOG. The gait disturbances associated with PD and in particular FOG can lead to falls. In PD populations falls are a leading cause of morbidity and mortality.

The primary treatment for PD symptoms is to prescribe drugs such as Levodopa™, a precursor for the neurotransmitter dopamine. This replacement therapy aims to replace endogenous dopamine that is lost due to neurodegeneration in the brain. Commonly, symptoms such as FOG can be medication refractory. Thus conventional therapy for gait disturbance is based on clinical diagnosis of a disturbance and appropriate alteration of the profile and dosage of medication. However a significant issue for PD patients is that the effectiveness of the drugs diminishes over time, leading to the condition as a whole becoming resistant to current pharmacological therapies.

Other therapies do exist, for example Deep Brain Stimulation (DBS), but not all patients are suitable for this type of intervention and the therapy is highly invasive and highly expensive. DBS is a neurosurgical procedure, which involves the implantation of a medical device, sometimes called a brain pacemaker, which sends electrical impulses, through implanted electrodes to specific parts of the brain for the treatment of movement and affective disorders. A deep brain stimulator requires the implantation of all components of the apparatus. The lead with electrodes is placed in the brain and the implanted pulse generator (IPG) is implanted subcutaneously below the clavicle or in the abdomen, with an insulated wire running from the IPG to the lead in the brain. The wire is routed below the skin, from the head, down the side of the neck, behind the ear to the IPG. Lead implantation involves an approximately 14 mm hole being drilled in the skull.

There is mounting evidence from a range of studies that cueing methodologies can improve gait performance in PD populations. These cues are temporal, spatial, audio or visual stimuli, which facilitate the initiation and continuation of repetitive sequential movements such as gait and can assist in handling, or even overcoming, gait irregularities, in particular freezing of gait episodes.

Some devices have been developed that provide cues as a means to stop gait irregularities. Other devices have been developed that provide cues as a means to prevent gait irregularities occurring in the first place. Such devices are activated (manually or automatically) when motion is detected, and provide continuous cueing, by for example repetitive sound from a metronome being delivered via an earpiece. More advanced systems aim to assess user cadence and adapt the delivered cue rhythm to the user's normal gait. An example of such a system is described in US2014/0249452A1.

The cue is normally intended to provide supportive information to the PD patient about step frequency or amplitude leading to a change in the motor response of the subject. The mechanism by which established cueing modalities work is not proven but reports suggest activation of alternate neural pathways bypassing the defective basal ganglia and accessing the motor programs controlling gait.

It appears that the technologies used to implement the prior systems are not very compatible with normal daily living requirements. They have the disadvantage of not being very discreet (earpiece worn on the ear, light-wand carried by patient) and they can be ineffective in busy, bright (seeing the light pattern from the light-wand/distinguishing the light pattern from the light-wand from varying ambient light conditions) or noisy (hearing the audio cue in your earpiece while being subject to a range of ambient noises) environments that one can typically encounter as you go about your daily life.

U.S. Pat. No. 7,917,225 (Advanced Neuromodulation Systems) describes application of electrical stimulation to a location of a patient's brain in response to a range of disorders including movement disorder. The approach proposed involves an invasive surgery to implant one or more electrodes directly at identified brain sites in the central nervous system.

EP2586489 (Bioness Neuromodulation Ltd) describes a system for improved stimulation systems based on gait signals associated with heel-contact events. It discloses improvements for force-sensitive resistors as part of an FES device system for controlling lower limb muscle contractions. The disclosure includes stimulation of muscles of the lower limb to control and guide muscle activity related to gait characteristics determined by a foot pressure sensor.

US2009/0099627 (Molnar et al) discloses detection of a movement state based on brain signals such as an electroencephalogram (ECG) signals, and delivery of a movement disorder therapy in the form a cue elicited by mechanical vibration applied to the skin. The therapy cue may be functional electrical stimulation (FES) or transcutaneous electrical stimulation (TENS) of a muscle or muscle group in order to help initiate movement or help a patient to control movement of a limb or other body part.

US2014/0249600 (Heruth et al) discloses detection of a patient's gait parameter, and providing stimulation by way of electrodes in the brain.

US2014/0249452 (March et al) discloses a freezing of gait cue apparatus. A visual cue is provided, in the form of a light beam on the ground.

The invention is directed towards providing a simpler and/or more effective system for improved management of gait problems in patients.

SUMMARY OF THE INVENTION

According to a first aspect of the invention, there is provided a gait management apparatus. The gait management apparatus may comprise at least one cueing actuator. The cueing actuator may comprise at least one stimulation apparatus configured to be disposed at one or more cueing sites on each side of a patient's body to provide bilateral stimulation. The gait management apparatus may comprise a memory for storing a non-transitory computer program. The gait management apparatus may comprise a controller programmed to execute the program stored in the memory to allow the controller to activate cueing. The at least one cueing actuator, the memory, and the controller may be in electrical contact. The controller may be programmed to activate cueing customized to the patient.

Bilateral cueing may be achieved by providing stimulation to the left and rights sides of the user's body in an alternating manner. For example, stimulation may be provided to the left side of a user's body to initiate/maintain movement of a limb on the left side of the user's body, and then stimulation may be provided to the right side of a user's body to initiate/maintain movement of a limb on the right side of the user's body.

The stimulation apparatus may be configured to provide electrical stimulation. The stimulation apparatus may be configured to provide haptic stimulation. The stimulation apparatus may be configured to provide electrical and haptic stimulation. The stimulation apparatus may be configured to provide electrical and haptic stimulation simultaneously.

The controller may be programmed to activate cueing based on the patient's gait cycle. Programming the controller to activate cueing based on a user's gait cycle enables stimulation to be provided at the desired times, which assists the user when walking. By using the user's specific gait cycle, the apparatus ensures that stimulation is provided at the correct point in the gait cycle.

The controller may be programmed to activate cueing based on fixed timings. The length of the user's average gait cycle may be pre-recorded and stored in the memory of the apparatus.

The controller may be programmed to activate cueing based on adaptive timings. The controller may be programmed to determine, the length of the user's previous gait cycle. The controller may be programmed to determine, the length of a one or more of the user's previous gait cycles and calculate the user's average recent gait cycle.

The controller may be programmed to activate cueing to prevent or mitigate a gait dysfunction when the controller determines the patient is walking or has an intention to walk. The controller may be programmed to activate cueing to relieve a gait dysfunction when the controller determines the patient is experiencing a gait dysfunction.

The stimulation apparatus may be disposed at a plurality of cueing sites on each side of the patient's body. The plurality of cueing sites may be located across a plurality of body parts. A plurality of cueing sites may be disposed on a plurality of body parts. A single cueing site may be present on a plurality of body parts.

The gait management apparatus may comprise a motion sensing system including one or more motion sensing elements configured to detect motion of the patient. The controller may be programmed to activate cueing in response to signals received from the motion sensing system.

The controller may be programmed to determine gait cycles of one or more previous strides of the patient using signals received from the motion sensing system. The controller may be programmed to determine gait activity of the patient using signals received from the motion sensing system.

The controller may be programmed to activate cueing for a current stride of the patient based on the gait cycles of the one or more previous strides. The controller may be programmed to activate cueing for a current stride of the patient based on the gait activity.

The motion sensing system may be configured to be disposed on an arm of the patient. The motion sensing system may be configured to be disposed on a leg of the patient. The motion sensing system may be configured to be disposed on both a leg and an arm.

The controller may be programmed to determine movement of a leg of the patient during the current stride. The controller may be programmed to activate cueing to provide stimulation to a contralateral arm of the patient to enable a timing relationship between the movement of the contralateral arm of the patient with movement of the leg of the patient.

The controller may be programmed to determine movement of an arm of the patient during the current stride. The controller may be programmed to activate cueing to provide stimulation to a contralateral leg of the patient to enable a timing relationship between the movement of the contralateral leg of the patient with movement of the arm of the patient.

According to a second aspect of the invention, there is provided a gait management apparatus. The gait management apparatus may comprise at least one cueing actuator. The cueing actuator may comprise at least one stimulation apparatus configured to be disposed on one side of a patient's body to provide mono-lateral stimulation. The gait management apparatus may comprise a memory for storing a non-transitory computer program. The gait management apparatus may comprise a controller programmed to execute the program stored in the memory to allow the controller to activate cueing. The at least one cueing actuator, the memory, and the controller may be in electrical contact. The controller may be programmed to activate cueing customized to the patient.

Mono-lateral cueing may be achieved by providing stimulation to one side of the user's body once per gait cycle. For example, stimulation may be provided to the user's body to initiate/maintain movement of a limb at the same point each in each gait cycle.

The stimulation apparatus may be configured to provide electrical stimulation. The stimulation apparatus may be configured to provide haptic stimulation. The stimulation apparatus may be configured to provide electrical and haptic stimulation. The stimulation apparatus may be configured to provide electrical and haptic stimulation simultaneously.

The controller may be programmed to activate cueing based on the patient's gait cycle. Programming the controller to activate cueing based on a user's gait cycle enables stimulation to be provided at the desired times, which assists the user when walking. By using the user's specific gait cycle, the apparatus ensures that stimulation is provided at the correct point in the gait cycle.

The controller may be programmed to activate cueing based on fixed timings. The length of the user's average gait cycle may be pre-recorded and stored in the memory of the apparatus.

The controller may be programmed to activate cueing based on adaptive timings. The controller may be programmed to determine, the length of the user's previous gait cycle. The controller may be programmed to determine, the length of a one or more of the user's previous gait cycles and calculate the user's average recent gait cycle.

The controller may be programmed to activate cueing to prevent or mitigate a gait dysfunction when the controller determines the patient is walking or has an intention to walk. The controller may be programmed to activate cueing to relieve a gait dysfunction when the controller determines the patient is experiencing a gait dysfunction.

The stimulation apparatus may be disposed at a plurality of cueing sites on each side of the patient's body. The plurality of cueing sites may be located across a plurality of body parts. A plurality of cueing sites may be disposed on a plurality of body parts. A single cueing site may be present on a plurality of body parts.

The gait management apparatus may comprise a motion sensing system including one or more motion sensing elements configured to detect motion of the patient. The controller may be programmed to activate cueing in response to signals received from the motion sensing system.

The controller may be programmed to determine gait cycles of one or more previous strides of the patient using signals received from the motion sensing system. The controller may be programmed to determine gait activity of the patient using signals received from the motion sensing system.

The controller may be programmed to activate cueing for a current stride of the patient based on the gait cycles of the one or more previous strides. The controller may be programmed to activate cueing for a current stride of the patient based on the gait activity.

The motion sensing system may be configured to be disposed on an arm of the patient. The motion sensing system may be configured to be disposed on a leg of the patient. The motion sensing system may be configured to be disposed on both a leg and an arm.

According to a third aspect of the invention, there is provided a gait management apparatus. The gait management apparatus may comprise at least one cueing actuator. The cueing actuator may comprise at least one stimulation apparatus configured to provide stimulation to a patient. The stimulation may be defined by at least one stimulation parameter. The gait management apparatus may comprise a memory for storing a non-transitory computer program. The gait management apparatus may comprise a controller programmed to execute the program stored in the memory to allow the controller to activate cueing. The at least one cueing actuator, the memory, and the controller may be in electrical contact. The controller may be programmed to activate cueing customized to the patient. The controller may be programmed to vary the at least one parameter of the stimulation so as to prevent user habituation to the stimulation.

The at least one stimulation parameter may be changed through different modalities in a predetermined manner. The at least one stimulation parameter may be changed through different modalities in a randomised manner. The at least one stimulation parameter may be changed through different modalities with or without patient initiation of the transition to the next modality in the cycle.

The at least one stimulation parameter may include: a stimulation pulse width; a stimulation pulse frequency; an inter-pulse interval; a ramp-up time; an ON-time; an OFF-time; a ramp-down time; or a stimulation intensity.

The at least one stimulation apparatus may be configured to be disposed at a plurality of sites across the patient's body. The at least one stimulation parameter may include a site at which the cueing is activated.

The stimulation apparatus may be configured to provide electrical stimulation. The stimulation apparatus may be configured to provide haptic stimulation. The stimulation apparatus may be configured to provide electrical and haptic stimulation. The stimulation apparatus may be configured to provide electrical and haptic stimulation simultaneously. The at least one parameter may include a type of stimulation provided to the patient The at least one stimulation parameters may comprise a mode of stimulation. The mode of stimulation may be selected from a mode of stimulation configured to relieve a gait dysfunction and a mode of stimulation configured to prevent or mitigate a gait dysfunction.

According to the invention, there is provided a gait management apparatus comprising: at least one motion sensor, at least one cueing actuator with electrical stimulation electrodes, a controller configured to process motion sensing signals from said at least one motion sensor, to perform automatic detection of a gait dysfunction or potential gait dysfunction, and to activate said cueing actuator automatically upon said detection, wherein the controller and the cueing actuator are configured to perform sensory level cueing and motor level cueing, wherein the controller is configured to determine if cueing at a sensory level is required or if cueing at a motor level is required, and to provide output signals to the cueing actuator accordingly, and wherein the controller is configured to determine characteristics of a patient and to activate cueing customised to the patient.

In one embodiment, said gait dysfunction is freezing of gait. In one embodiment, said characteristics include skin impendence, and/or sensory threshold, and/or motor threshold, and/or pain threshold, and/or pain tolerance. In one embodiment, said characteristics include the patient's changing response to motor level stimulation as a cue and/or the patient's changing response to sensory level stimulation as a cue.

In one embodiment, the controller is configured to activate the cueing actuator to prevent gait dysfunction when the controller senses that a patient is walking or has an intention to walk.

In one embodiment, the controller is configured to apply electrical stimulation cueing at an intensity level which is insufficient for functional muscle contraction, in which said cueing includes stimulation of either afferent or efferent nerves, in which afferent nerve stimulation causes a patient central nervous system to cause an action, and efferent nerve stimulation directly causes a muscle contraction with consequent triggering of afferent nerves causing the patient's central nervous system to trigger an action giving rise to a natural motor response, and in which said efferent nerve cueing is at an intensity level which is insufficient for functional muscle contraction.

In one embodiment, the controller is configured to control cueing to exceed a multi-modal somatosensory threshold but not to cause a functional muscular contraction, in which electrode stimulation intensity is across a full continuum from a simple muscle twitch response up to but not including a muscle contraction of sufficient intensity as would aid in the execution of a functional movement.

Preferably, the controller is configured to operate in a continuous cueing mode or an adaptive cueing mode, in which: in the continuous mode, cueing is performed whenever the user is not seated, standing still or lying, in which cueing is performed upon detection of intention to walk until the controller determines that the user stops walking, and in the adaptive mode cueing is performed to prevent freezing-of-gait only in response to alterations in gait dynamics or detection of a freezing-of-gait pre-cursor.

In one embodiment, the controller is configured to activate cueing with a series of bursts until it automatically determines that gait dysfunction has ended. In one embodiment, the controller is configured to dynamically modify cueing in real time according to conditions. Preferably, the controller is configured to modulate stimuli in real-time using closed loop control. In one embodiment, the controller is configured to maintain and monitor at least one three dimensional stimulus space, one for cutaneous multi-modal somatosensory electrical stimulation and/or one for motor multi-modal somatosensory electrical stimulation.

In one embodiment, the controller is configured to manage a stimulus effect of independent stimulation parameters working together to increase or decrease the effect of the electrical stimulus. In one embodiment, said parameters include stimulus intensity voltage, ramp-up time, and pulse Frequency. In one embodiment, the controller is configured to identify stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation.

In one embodiment, the controller is configured to modulate stimulus intensity by moving along a stimulation modulation profile line from a point of lowest intensity to a point of highest intensity with adjustment of all parameters simultaneously, using an adjustable window size. In one embodiment, the controller is configured to divide the stimulation modulation profile line into multiple steps from a minimum stimulus point to a maximum stimulus point.

In one embodiment, the controller is configured to operate in a freezing-of-gait prevention mode in which the controller measures a percentage of time the patient was in a freezing-of-gait state for a last time window and modulates stimulus to be used for a next cycle on the basis of this measurement. Preferably, the controller is configured to operate in the freezing-of-gait prevention mode at a lowest stimulation point while the patient is detected to be walking.

In one embodiment, the controller is configured to move along the line according to the extent of freezing-of-gait detected in a previous time window. In one embodiment, the controller is configured to choose per-patient a line to follow as part of the patient characteristics.

In one embodiment, the controller is configured to operate in a freezing-of-gait relief mode in which there is progressively greater stimuli applied in steps along said profile line until freezing-of-gait has stopped. In one embodiment, the controller is configured to receive a user input of how aggressively stimulus will be increased to relieve freezing-of-gait if it persists.

In one embodiment, the controller is configured to activate cueing by providing cueing signals with a pulse width of up to 1000 μs, and an inter-pulse interval of up to 1000 μs.

In one embodiment, the inter-pulse width is up to 100 μs. In one embodiment, the controller is configured to activate cueing by providing cueing signals with a pulse frequency of up to 60 Hz. In one embodiment, the controller is configured to activate cueing by providing cueing signals for a maximum electrode stimulation surface voltage of up to 100 V. In one embodiment, the controller is configured to activate cueing by providing cueing signals for a maximum electrode stimulation surface voltage of up to 68 V.

In one embodiment, at least some electrodes are implantable and the controller is configured to provide stimulation signals for said implantable electrodes to provide a current in the range up to 200 mA. In one embodiment, the controller is configured to provide stimulation signals for said implantable electrodes to provide a current in the range from 10 μA to 50 mA.

In one embodiment, the controller is configured to provide cueing actuator signals with an envelope having a ramp-up time of up to 5000 ms, an ON time of up to 10,000 ms, a ramp-down of up to 1000 ms, and an OFF time of up to 10,000 ms. In one embodiment, the ramp-down time is in the range of up to 500 ms and the OFF time is up to 5000 ms.

In one embodiment, at least one actuator pair of electrodes is arranged to be skin surface mounted. In one embodiment, at least one actuator pair of electrodes is arranged to be implanted under a patient's skin.

In one embodiment, the apparatus further comprises a patient interface, and the controller is configured to activate cueing in response to a manual cueing instruction at said interface. In one embodiment, the interface comprises a button for manual cueing activation.

In one embodiment, the controller is configured to recognise at least one tap as a patient trigger to activate cueing. In one embodiment, the controller is configured to be customised to parameters specific to a patient for recognising taps. Preferably, the controller is configured to recognise a series of multiple taps as said patient trigger. In one embodiment, the controller is configured to recognise a series of two taps as said patient trigger.

In one embodiment, the controller is configured to recognise said taps if they comply with parameters of (a) latency, being a minimum time which must elapse between the first and the second tap being performed, (b) threshold, which is a minimum acceleration which must be detected before an acceleration spike is recognised as a tap, (c) time limit, which is the maximum time which can elapse from the acceleration signal exceeding the threshold to returning below the threshold, and (d) window, which is the time after the latency, by which time the subsequent tap must have crossed the threshold.

In one embodiment, the controller is configured to operate with the following limits for said parameters: latency time up to 635 ms, threshold acceleration 5 m/s$^2$ to 100 m/s$^2$, time limit up to 1270 ms, and window time up to 1270 ms.

In one embodiment, the controller is configured to recognise said tapping on an enclosure of the controller.

In one embodiment, the apparatus comprises at least one accelerometer linked with the controller and the controller is configured to use inputs from said accelerometer as tap inputs.

In one embodiment, at least one cueing actuator is wirelessly linked with the controller, and the controller may include a smartphone programmed with apparatus control software.

In one embodiment, at least one cueing actuator is configured to be worn, for example wrist-worn.

In one embodiment, the cueing actuator includes a mechanical stimulation device.

In one embodiment, the mechanical stimulation device is configured to perform mechanical vibration.

In another aspect, the invention provides a gait management method comprising steps performed by a controller with a digital processor linked to at least one motion sensor and with at least one cueing actuator including electrical stimulation electrodes, the method including the steps of: receiving patient motion signals from the at least one motion sensor, processing said motion sensing signals to perform automatic detection of a gait dysfunction or potential gait dysfunction, and activating the cueing actuator automatically upon said detection, in a manner customised to a patient and being at a sensory level or a motor level, according to said motion signals and characteristics of a patient.

In one embodiment, said gait dysfunction is freezing of gait.

In one embodiment, said characteristics include skin impendence, and/or sensory threshold, and/or motor threshold, and/or pain threshold, and/or pain tolerance.

In one embodiment, said characteristics include a patient's changing response to motor level stimulation as a cue and/or the patient's changing response to sensory level stimulation as a cue.

In one embodiment, the controller activates the cueing actuator to prevent gait dysfunction when the controller senses that a patient is walking or has an intention to walk.

In one embodiment, the controller applies electrical stimulation cueing at an intensity level which is insufficient for functional muscle contraction, in which said cueing includes stimulation of either afferent or efferent nerves, in which afferent nerve stimulation causes a patient central nervous system to cause an action, and efferent nerve stimulation directly causes a muscle contraction with consequent triggering of afferent nerves causing the patient's central nervous system to trigger an action giving rise to a natural motor response, and in which said efferent nerve cueing is at an intensity level which is insufficient for functional muscle contraction.

In one embodiment, the controller controls cueing to exceed a multi-modal somatosensory threshold but not to cause a functional muscular contraction, in which electrode stimulation intensity is across a full continuum from a twitch response up to but not including a muscle contraction of sufficient intensity as would aid in the execution of a functional movement.

In one embodiment, the controller operates in a continuous cueing mode or an adaptive cueing mode, in which: in the continuous mode, cueing is performed whenever the user is not seated, standing still or lying, in which cueing is performed upon detection of intention to walk until the controller determines that the user stops walking, and in the adaptive mode cueing is performed to prevent freezing-of-gait only in response to alterations in gait dynamics or detection of a freezing-of-gait pre-cursor.

In one embodiment, the controller activates cueing with a series of bursts until it automatically determines that gait dysfunction has ended. In one embodiment, the controller dynamically modifies cueing in real time according to conditions. In one embodiment, the controller modulates stimuli in real-time using closed loop control.

In one embodiment, the controller maintains and monitors at least one multi-dimensional stimulus space, one for cutaneous multi-modal somatosensory electrical stimulation and/or one for motor multi-modal somatosensory electrical stimulation.

In one embodiment, the controller manages a stimulus effect of independent stimulation parameters working together to increase or decrease the effect of the electrical stimulus.

In one embodiment, said parameters include stimulus intensity voltage, ramp-up time, and pulse frequency. In one embodiment, the controller identifies stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation, and the controller modulates stimulus intensity by moving along a stimulation modulation profile line from a point of lowest intensity to a point of highest intensity with adjustment of all parameters simultaneously, using an adjustable window size.

In one embodiment, the controller recognises at least one tap as a patient trigger to activate cueing. In one embodiment, the controller is customised to parameters specific to a patient for recognising taps. Preferably, the controller recognises a series of multiple taps as said patient trigger. In one embodiment, the controller recognises a series of two taps as said patient trigger.

In one embodiment, the controller recognises said taps if they comply with parameters of (a) latency, being a minimum time which must elapse between the first and the second tap being performed, (b) threshold, which is a minimum acceleration which must be detected before an acceleration spike is recognised as a tap, (c) time limit, which is the maximum time which can elapse from the acceleration signal exceeding the threshold to returning below the threshold, and (d) window, which is the time after the latency, by which time the subsequent tap must have crossed the threshold.

In another aspect, the invention provides a non-transitory computer readable medium comprising software code for performing the steps of a method of any embodiment when executed by a digital computer According to the invention, there is provided a gait management apparatus for a user suffering from a neurological disease displaying gait dysfunction, the apparatus comprising: at least one motion sensor, at least one cueing actuator or device with an electrical stimulation electrode, a controller configured to process motion sensing signals, to perform automatic detection of a gait dysfunction or potential gait dysfunction, and to activate said cueing actuator automatically upon said detection.

In one embodiment, the cueing actuators include a haptic actuator. In one embodiment, at least one actuator is arranged to be skin surface mounted. In one embodiment, at least one actuator is arranged to be implanted under a patient's skin. In one embodiment, at least one haptic actuator is arranged to be wrist-worn. In one embodiment, the apparatus further comprises a user interface and wherein the controller is configured to allow the user to activate cueing manually.

In one embodiment, the controller at least in part comprises a smartphone. In one embodiment, the controller is configured to activate one of haptic or electrical cueing in response to a manual cueing instruction. In one embodiment, the interface comprises a button for manual cueing activation. In one embodiment, at least one cueing actuator is configured to be worn.

In one embodiment, at least one cueing actuator is wirelessly linked with the controller.

In one embodiment, the controller is configured to detect freezing of gait occurrences and to activate cueing upon said detection. In one embodiment, the controller is configured to generate an output sensory level cueing signal to relieve or prevent gait abnormality. In one embodiment, the controller is configured to generate an output motor level cueing signal to relieve or prevent gait abnormality. In one embodiment, the controller is configured to generate cueing signals for surface-mounted electrodes. In one embodiment, the controller is configured to generate cueing signals for implanted electrodes.

In one embodiment, the controller is configured to apply electrical stimulation cueing to prevent the occurrence of freezing of gait when the controller senses that a patient is walking or has an intention to walk.

In one embodiment, the controller is configured to determine characteristics of a patient and to deliver electrical stimulation cueing customised to determined requirements of the patient. In one embodiment, said characteristics include skin impendence, and/or sensory threshold, and/or motor threshold, and/or pain threshold, and/or pain tolerance. In one embodiment, the controller is configured to apply cueing with a series of bursts until it automatically determines that a gait abnormality has ended.

In one embodiment, the processor is configured to apply electrical stimulation cueing at an intensity level which is insufficient for muscle contraction but sufficiently high to elicit a sensory response. In one embodiment, at least one cueing actuator comprises a wrist-worn haptic device such as a digital watch with haptic functionality for sensory stimulation.

In one embodiment, the controller is configured to determine if stimulation at a sensory level for cueing purposes is required or if stimulation at a motor level is required, and to provide output signals accordingly.

In one embodiment, the controller is configured to output stimulation signals with a pulse width of up to 1000 µs, and an inter-pulse interval of up to 100 µs. In one embodiment, the controller is configured to output stimulation signals with a pulse frequency of up to 60 Hz.

In one embodiment, the controller is configured to output stimulation signals for a maximum stimulation surface voltage of 68 V. In one embodiment, the controller is configured to output stimulation signals for an implanted stimulation current range from 10 µA to 50 mA.

In one embodiment, the controller is configured to output stimulation signals with an envelope having characteristics of a ramp-up time of up to 5000 ms, an ON time of up to 10,000 ms, a ramp-down of up to 500 ms, and an OFF time of up to 5000 ms.

In various embodiments the invention provides a gait management apparatus for a user suffering from a neurological disease displaying gait dysfunction. The apparatus comprises: a controller, sensors (for example, accelerometers, gyroscopes and EMG) which may be worn externally on the person or implanted, and a cueing actuator(s). Cueing modality is in the form of an electrical or haptic (mechanical) cue, for electrical cueing electrodes for cueing delivery at least one anatomical site either on the skin surface or implanted just below the skin surface, a haptic cueing device worn at the wrist or other appropriate site. There may be an interface for coupling with electrical stimulation electrodes, a controller configured to receive sensing signals, a controller configured to allow the user to activate cueing manually, and a controller to process motion sensing signals to activate cueing automatically at the electrodes or haptic cue site to relieve or prevent a gait abnormality. An interface (such as a smartphone) may be provided to control, change, store and transmit required cueing parameters.

The apparatus may have some or all of the following features: An actuator for user self-actuation (manual activation) of electrical cueing. An actuator for user self-actuation (manual activation) of haptic cueing. The actuator comprises a device configured to be worn on the person. The cueing device is wirelessly linked with the processor. The motion sensing module is configured to detect freezing of gait occurrences and to activate cueing upon said detection. The controller is further configured to generate an output sensory level cueing signal to relieve or prevent gait abnormality. The controller is further configured to generate an output motor level cueing signal to relieve or prevent gait abnormality. The controller is configured to generate cueing signals for surface-mounted electrodes. The controller is configured to generate cueing signals for implanted electrodes. The processor is programmed to apply electrical stimulation cueing to prevent the occurrence of freezing of gait when the controller senses that a patient is walking or has an intention to walk. The controller is configured to determine characteristics of a patient and to deliver electrical stimulation cueing customised to determined requirements of the patient, and these characteristics may include skin impendence, sensory threshold, motor threshold, pain threshold and pain tolerance. The processor is configured to apply stimulation (electrical or haptic) with a series of bursts until it automatically determines that a gait abnormality has ended. The processor is configured to apply electrical stimulation at an intensity level which is insufficient for muscle stimulation but sufficiently high to elicit a sensory response. The processor is operating on a mobile platform such as Apple iPhone™ and via the Apple Watch applies haptic (mechanical vibrations) cueing at an intensity level which is sufficient for sensory stimulation. The processor is operating on a mobile device such as Android™, Android Wear™ or Microsoft™ platforms and via a smartwatch applies haptic (mechanical vibrations) cueing at an intensity level which is sufficient for sensory stimulation. The processor is configured to determine if stimulation at a sensory level for cueing purposes is required or if stimulation at a motor level is required and provides output signals accordingly. The processor is configured to output stimulation signals with a pulse width of up to 1000 µs, and an inter-pulse interval of up to 100 µs. The processor is configured to output stimulation signals with a pulse frequency of up to 60 Hz. The processor is configured to output stimulation signals for a maximum stimulation surface voltage of 68V. The processor is configured to output stimulation signals for an implanted stimulation current range from 10 µA to 50 mA. The processor is configured to output stimulation signals with an envelope having characteristics of a ramp-up time of up to 5000 ms, an ON time of up to 10,000 ms, a ramp-down of up to 500 ms, and an OFF time of up to 5000 ms.

DETAILED DESCRIPTION OF THE INVENTION

BRIEF DESCRIPTION OF THE DRAWINGS

The invention will be more clearly understood from the following description of some embodiments thereof, given by way of example only with reference to the accompanying drawings in which:—

FIG. 21 shows examples of somatosensory receptors in more detail, FIG. 22 shows the somatosensory receptors found in tendons and skeletal muscle (proprioceptors) the Golgi Tendon Organ and Muscle Spindle respectively, and FIG. 23 shows joint somatosensory receptors in a typical joint such as the knee joint;

DESCRIPTION OF THE EMBODIMENTS

Overview

A cueing system is described for the relief and prevention of freezing of gait (FOG) particularly for Parkinson's disease. It provides in various embodiments a cue in the form of a burst of electrical stimulus either on the skin surface or directly on a sensory and/or motor nerve when a FOG event (common with neurological diseases like Parkinson's disease) is detected. FOG can be detected automatically by the system using a range of sensors or when the user senses their FOG episode themselves, he/she can manually activate the system. The system may also provide a regular pattern of electrical pulses (acting as a cue) when the person is walking to prevent FOG occurring.

Figure 22:
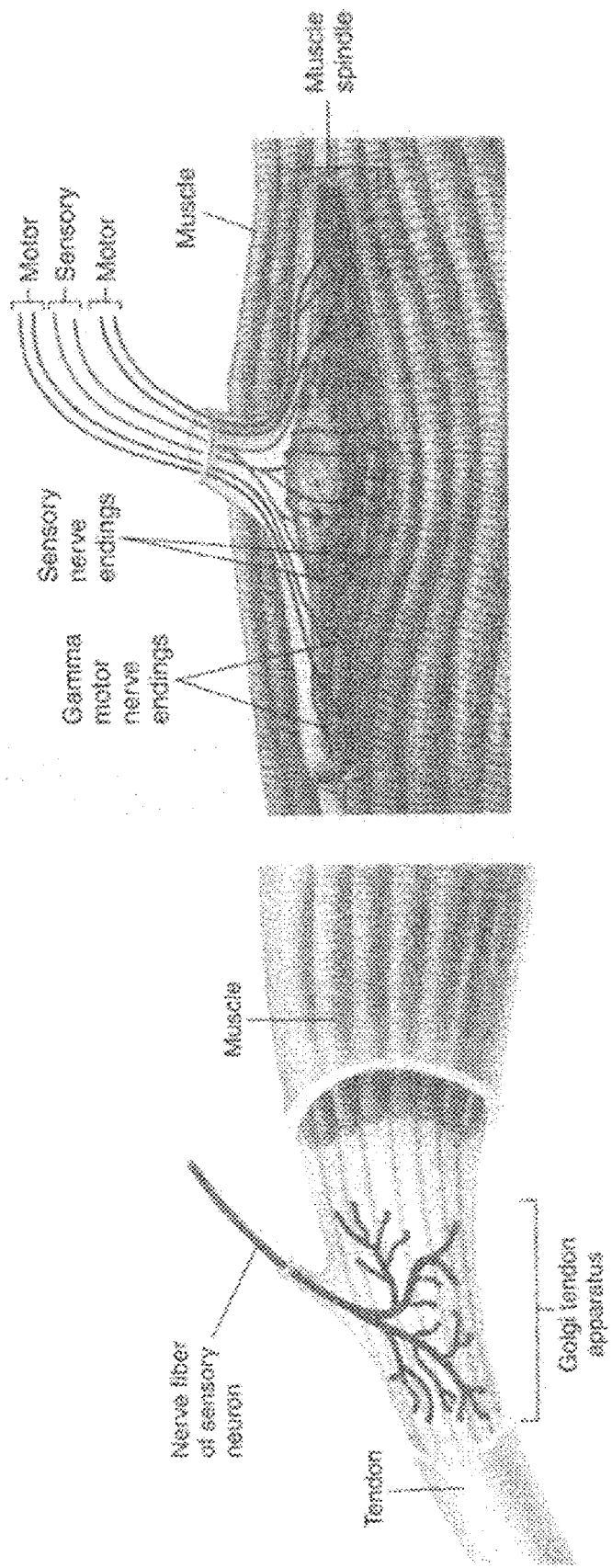
Figure 23:
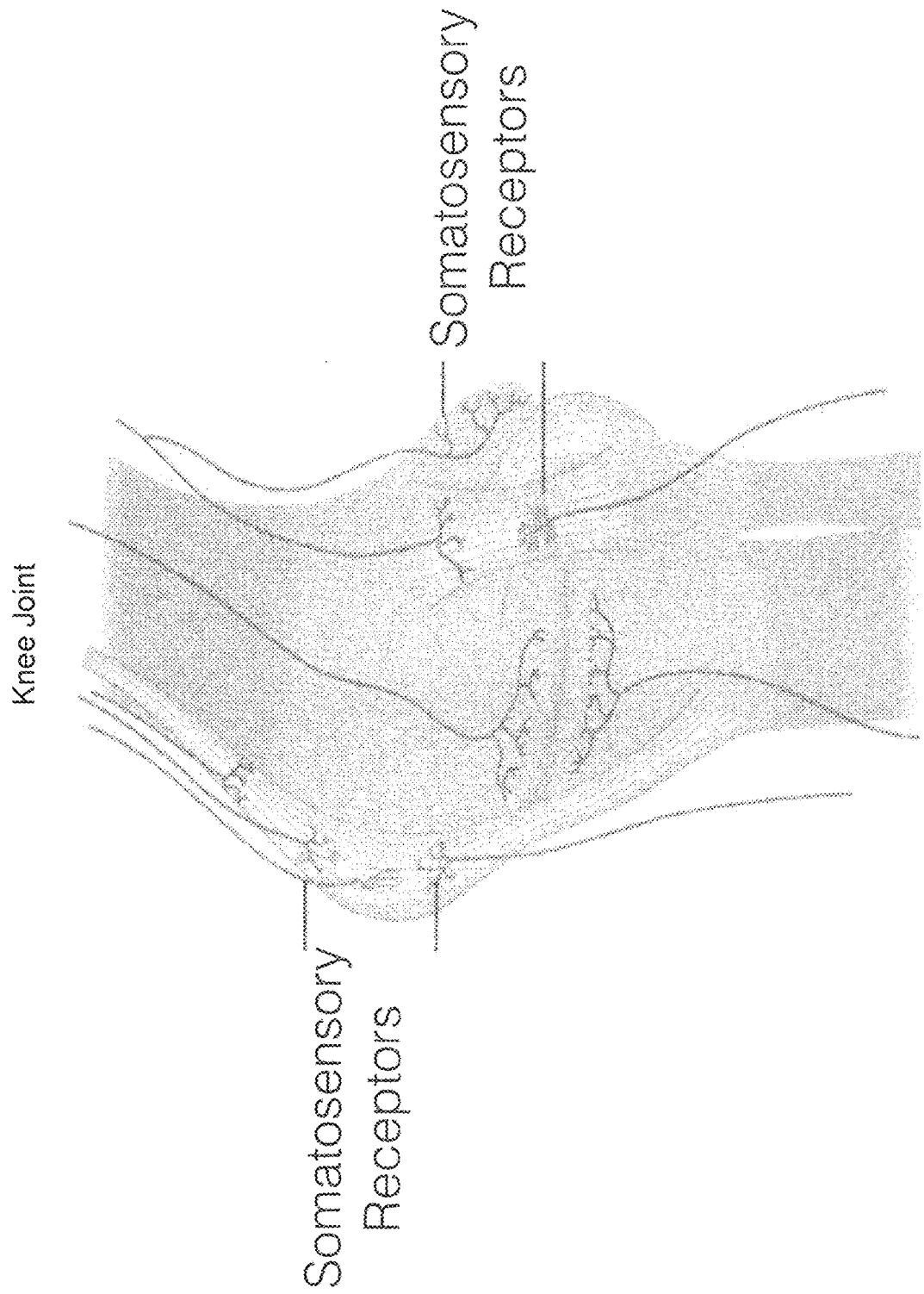
Figure 24:
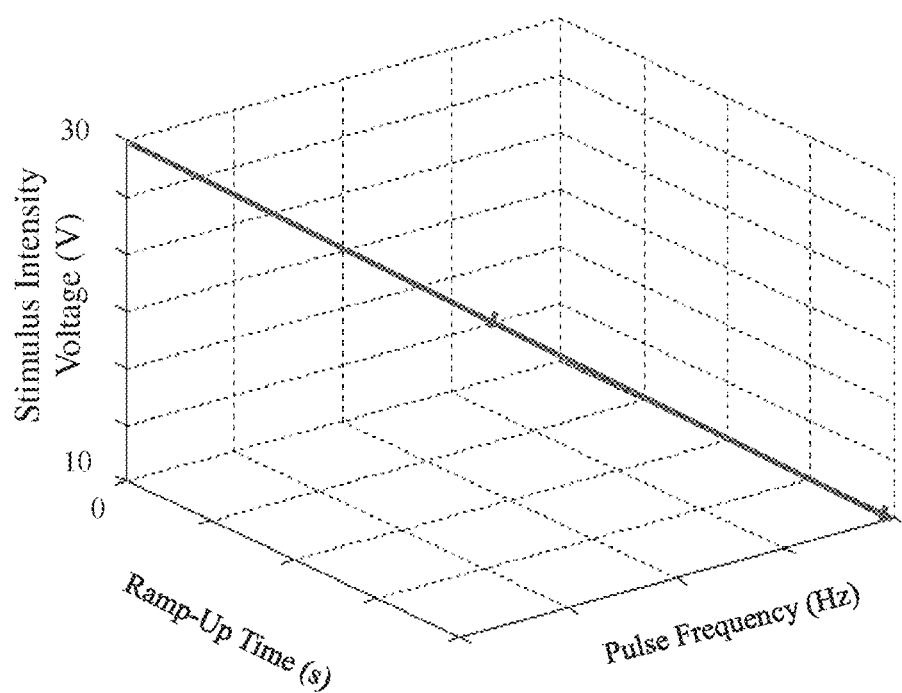
FIGS. 24 and 25 are 3D plots illustrating dynamic modification of cueing by following a line representing combinations of three parameters.
Figure 25:
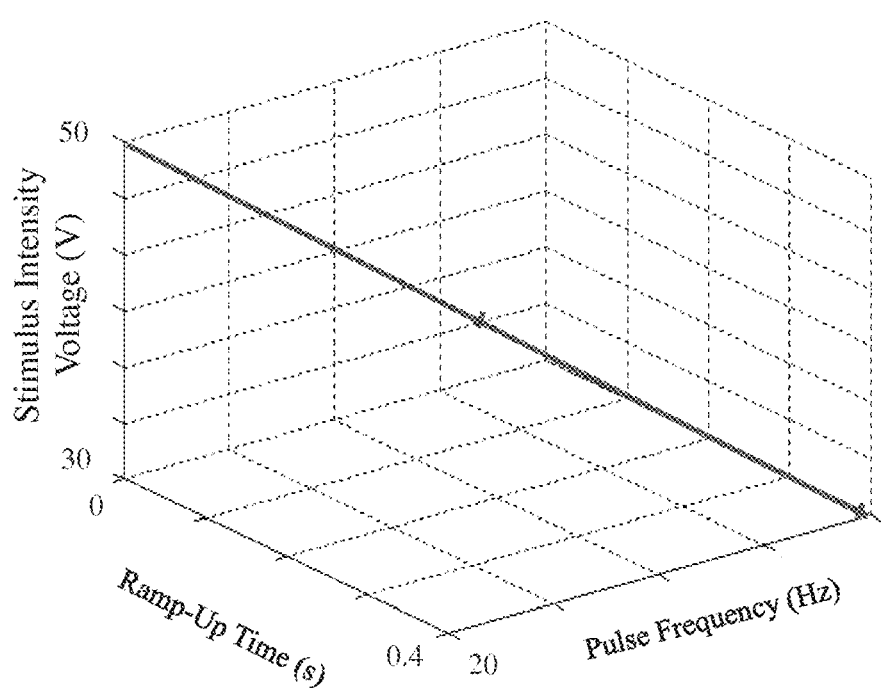
Figure 26:
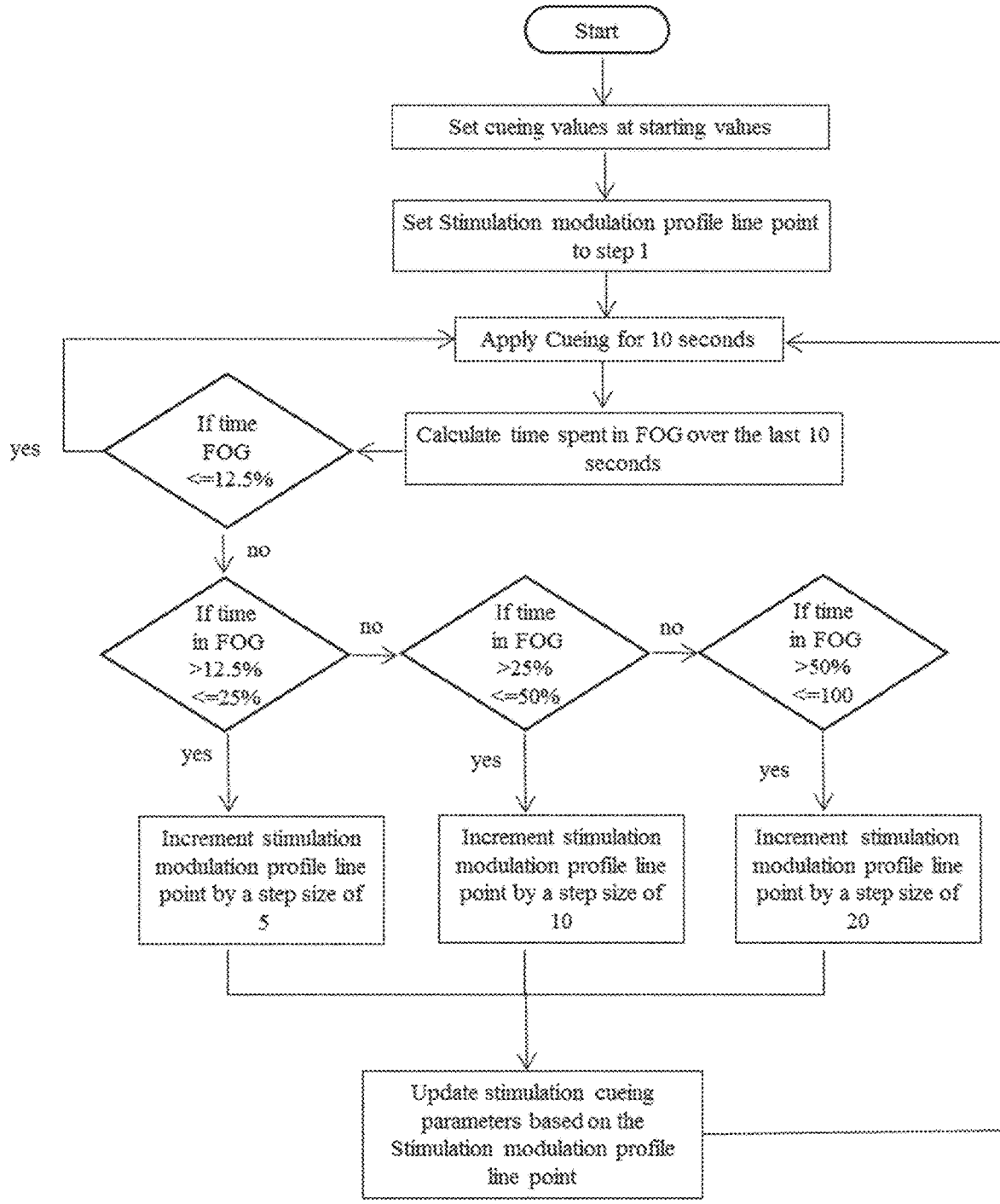
FIG. 26 is a flow diagram for operation of the controller for dynamic cueing modification.

FIGS. 1 to 19 inclusive and FIGS. 24 to 26 inclusive illustrate various embodiments, and FIGS. 20 to 23 illustrate a patient's anatomy which is responsive to cueing provided by the apparatus.

The somatosensory system is targeted in all cases and it represents several somatic sensation modalities such as cutaneous sensations (e.g. touch, temperature and pain) and proprioception sensations (e.g. muscle status (length/rate of change of length and tension) and joint angle). Each of these modalities and their sub-modalities (e.g. the cutaneous sensation of pain can be sharp, dull or deep) is represented by neurons that exhibit modality specificity. That is, when a specific somatosensory neuron is stimulated naturally (e.g., by touching the skin) or artificially (e.g., by electrical stimulation), the sensation perceived is specific to the neuron that is activated. Thus, a "touch" somatosensory neuron will naturally only respond to its adequate stimulus, which is touch and will not for example naturally respond to different stimulus, for example a change in skin temperature.

Figure 20:
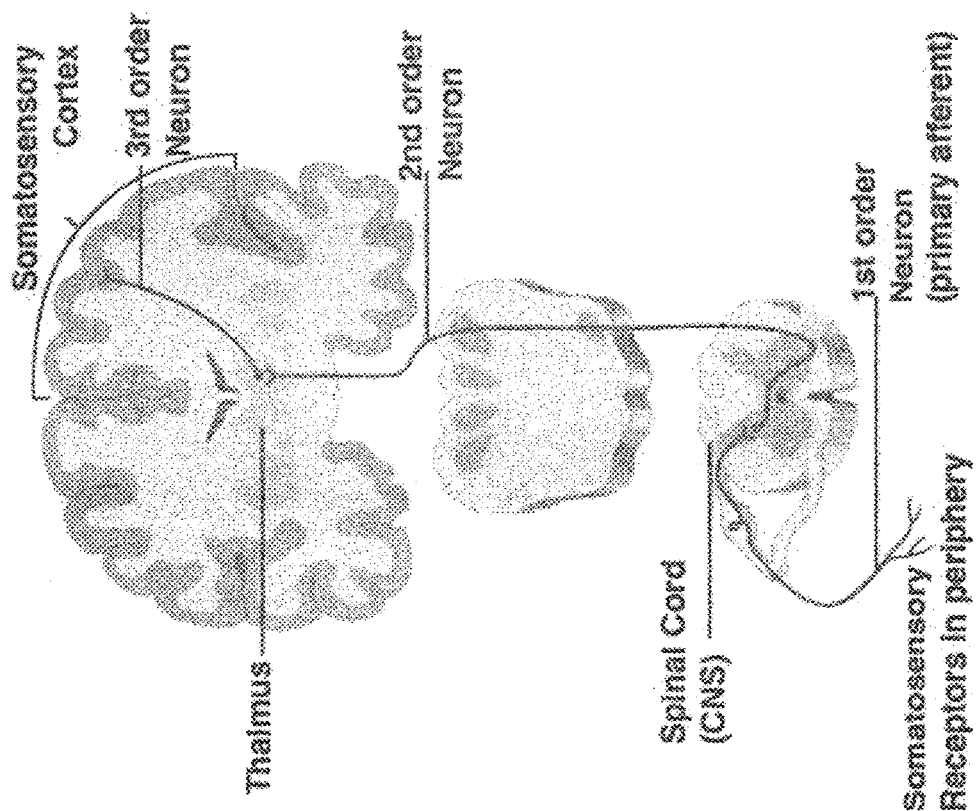
FIGS. 20 to 23 are diagrams illustrating anatomical and physiological components of the human somatosensory system to provide context to the invention, FIG. 20 showing the typical pathway from a peripherally located somatosensory receptor to the somatosensory cortex.

The somatosensory system is organised such that there is a chain of neurons starting at the sensory receptor and ending in the somatosensory cortex in the brain (FIG. 20).

The first neuron in this chain of neurons is referred to as the primary afferent neuron and is organised such that its axon and cell body are part of the peripheral nervous system. An afferent neuron is one which carries information from the periphery to the CNS. In contrast an efferent neuron carries information from the CNS. These peripheral nerves thus contain the specific sensory receptors for each modality and travel between the skin, muscles, tendons or joints and the central nervous system.

Figure 21:
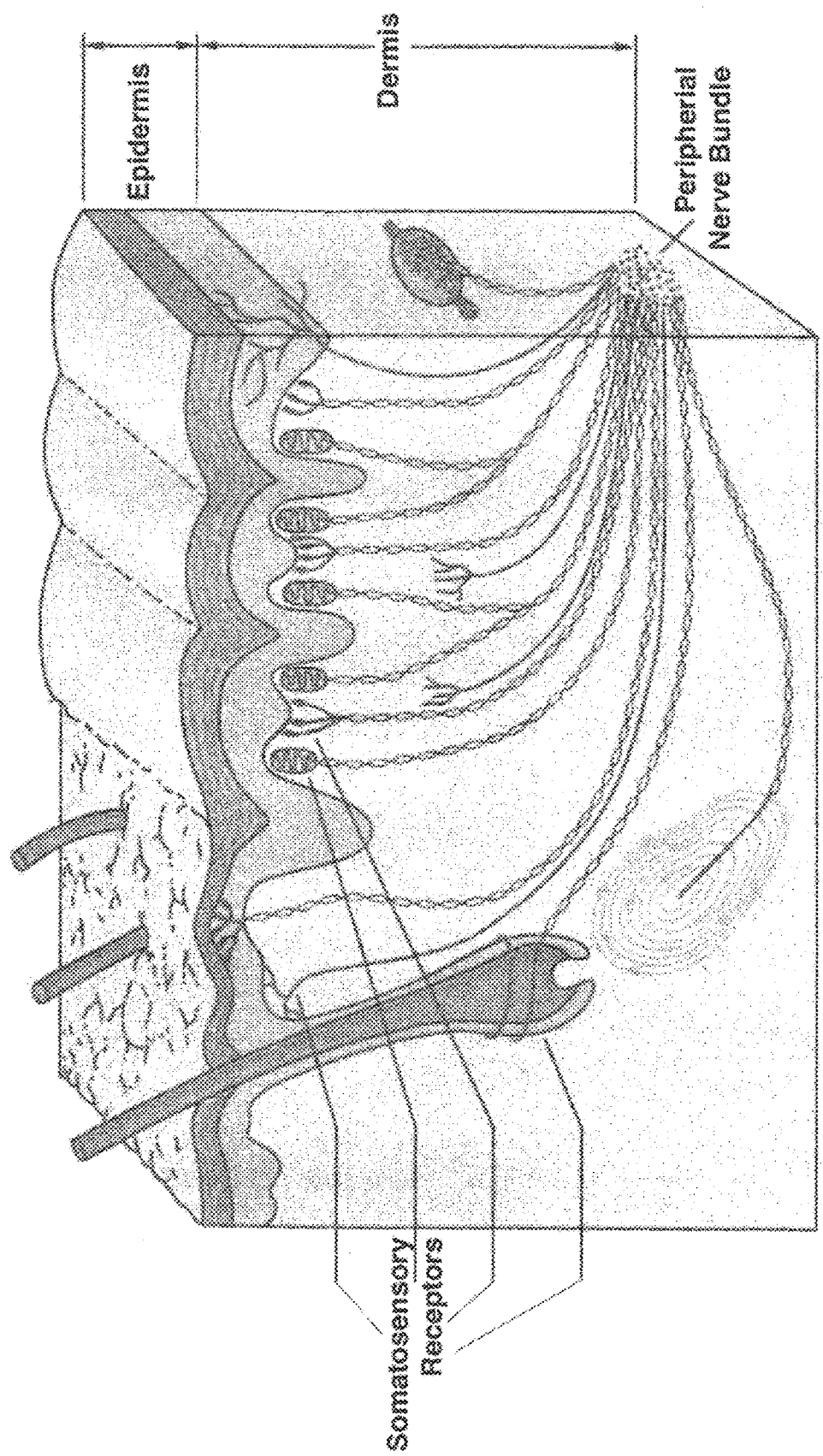

The peripheral nerve bundle pathways carrying the skin somatosensory information to the CNS, form a nerve bundle just below the skin surface, which allows for the convenient artificial activation of multiple modalities using appropriate electrical stimulation parameter values (amplitude, pulse width, inter-pulse interval, frequency, ramp up time, ramp-down, ON-time and OFF-time) delivered using either skin surface electrodes or implanted electrodes in proximity to the nerve bundle (FIG. 21).

Proprioceptors are located in muscles, tendons, joint ligaments and in joint capsules (FIGS. 22 and 23).

In skeletal muscle, there are two types of proprioceptors associated with skeletal muscle namely the muscle spindles and Golgi tendon organs. The muscle spindles are proprioceptors which monitor muscle length and its rate of change and signal the rate of change in muscle length by changing the discharge rate of the afferent nerve action potentials. The Golgi tendon organ monitors changes in muscle tension. Thus any stimulus that results in muscle contraction across the continuum from a simple twitch response to a maximal contraction resulting in a change in the joint angle, will result in the activation of additional (additional to the cutaneous somatosensory modalities) somatosensory sensory signals, proprioception somatosensory signals.

These proprioception somatosensory signals arise in response to muscle activation, thus acting as a potential cue to relieve or prevent FOG.

Additionally, within the joints, there are encapsulated nerve endings similar to those found in the skin, as well as numerous free nerve endings which fire in response to changes in joint angle. Thus electrical stimulation of skeletal muscle which results in muscle contraction across the continuum from a simple twitch response to a maximal contraction will produce somatosensory proprioceptive inputs to the CNS that may be effective cues for the relief and/or prevention of FOG. In this invention there are two distinct anatomical components involved: the Peripheral Nervous System (PNS) and the Central Nervous System (CNS). Arising from artificial electrical stimulation of the PNS, sensory action potential signals travel from the PNS to the CNS where this sensory input gives rise to a natural motor response (re-commence walking in the case of FOG relief or maintain walking in the case of FOG prevention).

The artificial electrical stimulation (using either surface or implanted means) of the PNS is where electrical stimulation is used to trigger either a one-step or a two-step somatosensory response.

In a one-step response, electrical stimulation triggers activation of a sensory nerve or nerves and the action potentials from these afferent sensory nerves travel to the CNS where they are processed. This one-step response is a cutaneous multi-modal somatosensory response from the PNS.

In a two-step response, Step one sees artificial electrical stimulation triggering activation of a motor nerve or nerves (efferent nerves) and the corresponding skeletal muscle is activated (albeit at a level below that required to produce a functional contraction). Step 2 then sees the firing of sensory receptors in the activated skeletal muscle (muscle spindle) or tendon (Golgi tendon organ) in response to this skeletal muscle activation. The action potentials from these sensory nerves (afferent nerves) then travel to the CNS where they are processed. The second step of this response is a multi-modal somatosensory response from the PNS.

The CNS is where the artificially induced sensory action potentials received from the PNS via afferent pathways, are acted on giving rise to a natural motor response (re-commence walking in the case of FOG relief or maintain walking in the case of FOG prevention).

Systems of the invention in various embodiments perform electrical stimulation to artificially cause multi-modal somatosensory stimulation, and different cueing modalities are triggered either individually or in combination through the use of appropriate electrical stimulation parameters. Advantageously, the processor is configured to dynamically choose how to perform stimulation, and this is performed according to the patient's individual characteristics. Preferably, the stimulation is somatosensory up to a level of non-functional movement, Hence the cueing can be sufficient to maybe cause muscle contraction, but will not be sufficient to aid in the execution of a functional movement. Ranges of appropriate electrical stimulation parameters include but are not limited to: pulse widths ranging from 0 µs up to 1000 µs, inter-pulse intervals ranging from Op up to 1000 µs, pulse frequencies ranging from 0 Hz up to 60 Hz, surface stimulation intensity voltages up to 100 V, surface stimulation intensity currents up to 200 mA, implanted stimulation intensity currents ranging from 0 µA to 200 mA, stimulation signals with an stimulation intensity envelope having characteristics of a ramp-up time of up to 1000 ms, an ON time of up to 10,000 ms, a ramp-down of up to 1000 ms, and an OFF time of up to 10,000 ms.

The apparatus has at least one motion sensor, and at least one cueing actuator or device with a pair of skin surface electrical stimulation electrodes or a pair of implanted electrical stimulation electrodes positioned to trigger activation of peripheral motor or sensory nerves. The skin surface electrical stimulation electrodes may be wired, in which case the electrode is simply a passive electrode 'patch', or the electrode may be wireless, where it is an active electronic device that communicates wireless with the actuator as well as incorporating the passive electrode 'patch'. For stimulation of motor nerves it is preferred that it is up to and including a stimulation that results in a muscle contraction which will not be sufficient to aid in the execution of a functional movement. A controller is configured in hardware and software programming to process motion sensing signals, to perform automatic detection of a gait dysfunction or potential gait dysfunction, and to activate the cueing actuator automatically upon detection.

A functional muscle contraction is a biomechanical-task based muscle contraction which is achieved by enabling a muscle contraction of sufficient intensity as to facilitate a functional movement, for example hand grasping in upper limb rehabilitation or drop foot correction in lower limb stroke rehabilitation. In each of these cases the muscle is contracted to a level to facilitate a functional task through limb movement.

A non-functional muscle contraction is a muscle contraction where the intensity of contraction is across the full continuum from a twitch response up to but not including a muscle contraction which will aid in the execution of a functional movement.

There may be at least one electrical stimulation actuator which is arranged to be wrist-worn. The apparatus may have a user interface and the controller may be programmed to allow the user to activate cueing manually.

In some examples, the controller may be configured in hardware and/or software to perform cueing with a stimulation which does not directly cause a functional muscle contraction. However, for the purposes of relieving or preventing gait abnormality, the cueing is sufficient to cause in the patient the full continuum of muscle contraction: from a simple twitch response of the skeletal muscle up to but not including a muscle contraction of sufficient intensity as would aid in the execution of a functional movement.

In several embodiments, the controller is configured to generate cueing signals at peripheral anatomical sites.

The controller in some examples determines characteristics of a patient and delivers electrical stimulation cueing customised to determined individualized requirements of the patient.

The cueing actuator may comprise a wrist-worn electrical stimulation device such as a digital watch with functionality for multi-modal somatosensory electrical stimulation in response to electrical stimulation of peripheral sensory nerve bundles in the vicinity of the wrist using skin surface electrical stimulation electrodes at the wrist or implanted electrical stimulation electrodes located internally in the vicinity of the wrist.

The controller of some examples determines in real time if for cueing purposes, and to generate an effective cueing signal, stimulation should be at a sensory level (sensory threshold being less than motor threshold) or at a motor level and to provide output electrical stimulation signals accordingly.

The sensors may for example be accelerometers, gyroscopes and EMG devices which may be worn externally on the person or implanted. There may be an interface for coupling with electrical stimulation electrodes. The controller may be configured to allow the user to activate cueing manually, and/or to activate cueing automatically to relieve or prevent a gait abnormality. An interface (such as a smartphone) may be provided to control, change, store and transmit required cueing parameters.

The controller is configured in various embodiments to: apply electrical stimulation cueing to prevent the occurrence of freezing of gait when the controller senses that a patient is walking or has an intention to walk, and determine characteristics of a patient and to deliver electrical stimulation cueing customised to the unique requirements of the patient, and these characteristics may include skin impendence, sensory threshold, motor threshold, pain threshold and pain tolerance.

The patient characteristics can be learned by logging and monitoring the motion sensor inputs and/or it can be inputted as a patient profile before use.

In the case of automatic, sensor-controlled FOG relief, the processor is configured to apply electrical stimulation with a series of bursts until it automatically determines that a gait abnormality has ended.

In the case of patient-activated FOG relief, the processor is configured to apply electrical stimulation with a predetermined number of bursts when instructed to do so by the patient.

The processor may be configured to apply electrical stimulation at an intensity level which is insufficient for muscle stimulation but sufficiently high to elicit a cutaneous multimodal somatosensory response from the PNS. The action potentials from these sensory nerves (afferent nerves) then travel to the CNS where they are processed and acted on giving rise to a natural motor response (re-commence walking in the case of FOG relief or maintain walking in the case of FOG prevention).

The processor may be configured to apply electrical stimulation at an intensity level which is sufficient for muscle stimulation, albeit at a level below that required to produce a functional contraction, giving rise to a multimodal somatosensory response from the PNS. The action potentials from these sensory nerves (afferent nerves) then travel to the CNS where they are processed and acted on giving rise to a natural motor response (re-commence walking in the case of FOG relief or maintain walking in the case of FOG prevention).

Ranges of appropriate electrical stimulation parameters include but are not limited to: pulse widths ranging from 0 µs up to 1000 µs, inter-pulse intervals up to 1000 µs, pulse frequencies ranging up to 60 Hz, surface stimulation intensity voltages up to 100 V, surface stimulation intensity currents up to 200 mA, implanted stimulation intensity currents ranging up 200 mA, stimulation signals with an stimulation intensity envelope having characteristics of a ramp-up time of up to 1000 ms, an ON time of up to 10,000 ms, a ramp-down of up to 1000 ms, and an OFF time of up to 10,000 ms.

A system of the invention may comprises a body-worn surface electrical stimulation device and/or a minimally invasive implanted electrical stimulation device, such as an injectable micro-stimulator, both of which deliver electrical stimulation elicited cues under manual or sensor control, to either relieve FOG (when it is detected) through the delivery of short duration bursts of electrical stimulation or to prevent FOG through the delivery of repetitive regularly timed bursts of electrical stimulation during walking. The system is a low-cost, minimally invasive system that is capable of operating effectively in a wide range of environmental conditions as the user goes about their daily life.

With the invention the electrical stimulation is primarily delivered to elicit a multi-modal somatosensory response from the PNS which is in turn acted on by the CNS and it is through this multi-modal somatosensory response that cueing occurs. Thus, stimulation levels are such as to exceed the multi-modal somatosensory threshold but are not in many cases at the levels normally used for functional muscular contraction. We refer to this electrical stimulation as "Multi-modal Somatosensory Electrical Stimulation Cueing". With a surface electrical stimulation electrode implementation, Multi-modal Somatosensory Electrical Stimulation Cueing is achieving by delivering electrical stimulus through a pair of skin surface electrodes, which can be placed close to each other (typically between 0-15 cm apart) on the skin at a wide range of sites. These sites can be chosen using a combination of three criteria: (i) a location on the skin where there is enhanced somato-sensory sensitivity, (ii) a location on the skin where electrodes will be concealed by clothing, (iii) a location on the skin where connection to a body-worn (waist-worn or wrist-worn) electronic unit is facilitated by the location (on surface of the quadriceps or hamstrings muscles when the body worn electronic unit is worn on the waist, on the wrist when the unit is worn on the wrist).

Another embodiment of the invention involves the use of skin surface mechanical stimulation as a cueing mechanism, rather than electrical stimulation cueing. The mechanical vibration would be delivered via a system of vibration motors fitted on a wrist worn device so that skin surface of the wrist is mechanically stimulated in a controlled manner under user or sensor control. The haptic feedback mechanism on a digital watch could be adapted for this purpose with a watch haptic engine delivering the skin surface mechanical stimulation cueing on the skin surface at the wrist. The algorithms and methods of control for controlling the delivery of this mechanical stimulation would be identical to those described herein for controlling the delivery of Sensory Electrical Stimulation cueing as shown in FIG. 7, FIG. 8, FIG. 10, FIG. 11, and FIG. 12. The cueing system using this method of the invention would be in the form of an App for a digital watch and the sensing mechanism would use the built-in watch sensors such as accelerometers, gyroscopes, barometers and magnetometers as well as the sensors in the accompanying smartphone. The self-activation of the delivery of mechanical stimulation cueing would be triggered by the user making a characteristic swipe on the digital watch surface, which could be recognized by the App, or by the user using a double tap action on the surface of the watch. An example of the type of digital watch is the Apple Watch™.

For sensor control of the electrical stimulation device, a range of sensors can be used such as accelerometers, gyroscopes, and physiological sensing such as EMG. These sensors can be located at different anatomical sites on the surface of the body and mounted into enclosures to facilitate attachment of the sensor at this site. For example, sensors could be mounted in an enclosure fitted on the wrist and/or mounted in an enclosure fitted on the waist. These sensors can be implanted using minimally invasive implantation techniques (for example using injectable techniques).

The invention facilitates manual, direct user controlled activation of electrical cues (button press, tapping (single or double), capacitive sensing of touch) or automatic motion sense detection as possible mechanisms to activate the electrical stimulus actuator directly. The apparatus also allows for manual activation via a wireless communication enabled wrist-worn switch or smartwatch type device. Additionally, the apparatus has the capacity for the automatic detection of alterations in gait patterns including FOG via built-in accelerometers and gyroscopes. This apparatus provides an electrical stimulation elicited cue for gait correction and FOG relief to enable a user to get out of FOG (FOG relief) and also allows for continuous or adaptive electrical stimulation cueing to prevent FOG occurring in real-time.

The apparatus can be deployed to deliver electrical stimulus to a range of anatomical sites. One manifestation for example of our invention involves the use of the actuator (body-worn wireless communication enabled stimulator device) worn on the waist connected via a wired connection to a pair of skin surface electrodes positioned on the skin over the quadriceps or hamstrings muscle. In the event that a FOG episode is experienced by the user, they can press a button on a wireless communication-enabled wrist-worn device, which triggers activation of the electrical stimulus actuator to relieve the FOG. The apparatus offers a highly significant contribution to PD healthcare in improving quality of life through gait correction, FOG relief and FOG prevention and contributing to less frequent hospitalization by reducing falls.

The apparatus is capable of non-invasively, automatically or directly under user control, supporting gait correction and/or gait facilitation in Parkinson's disease patients by means of an advantageous electrical cueing or mechanical cueing modality.

The apparatus carries out this cueing function in real time, as the user goes about their daily life and provides a mechanism for both FOG relief and FOG prevention. The level or intensity of electrical/mechanical stimulus used for each patient can be adjusted within custom-defined limits locally at the device level or can be adjusted remotely over the Internet possibly by a clinician responsibly for the persons care. The apparatus can be used in a wide variety of environments with equal effectiveness. Examples of use include in the users' home where gait disturbances and FOG events frequently occur as the user passes through doorways or when moving along a corridor. The apparatus can also be used outside the home and importantly, unlike other cueing systems, is unaffected by ambient light or noise.

The primary function of the apparatus is to provide an electrical cue (sensory or motor) or mechanical (sensory) upon occurrence of a gait irregularity or to prevent that gait irregularity occurring in the first place.

Apparatus Examples

Figure 1:
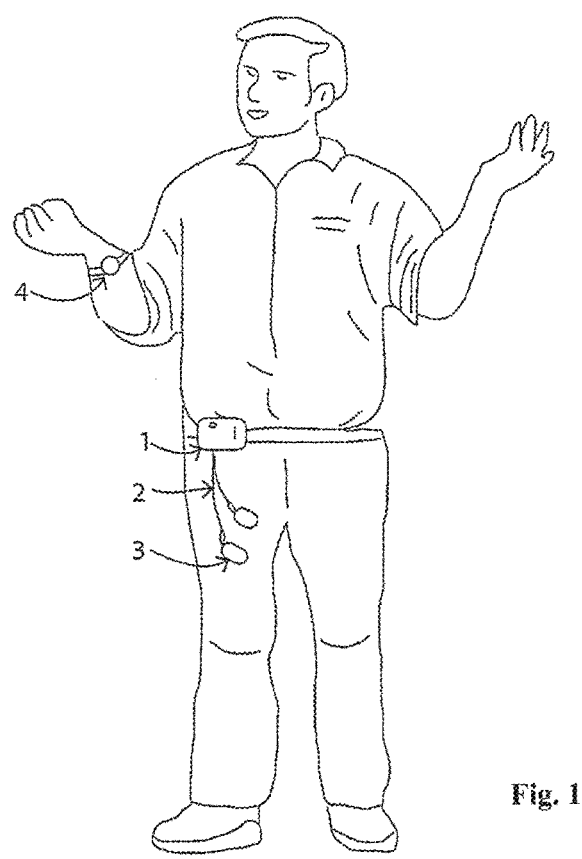
FIG. 1 is a diagram illustrating positioning of components of a system or "apparatus" of the invention on a patient.
Figure 2:
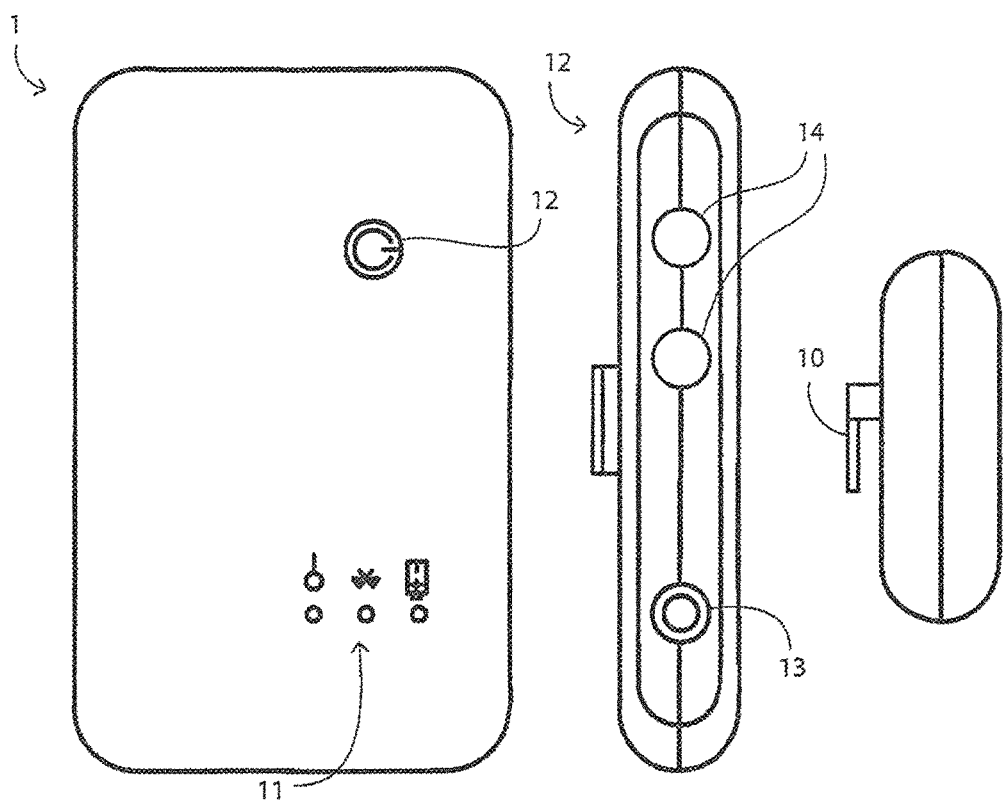
FIG. 2 is a set of front, plan, and side views of a control unit of the system.

In one embodiment the apparatus has a waist-worn electrical stimulation unit 1, connected by cables 2 to at least one pair of surface electrical stimulation electrodes 3 placed on the skin surface. Additionally, a wireless wrist worn accompanying device 4 can be employed with or without a smartphone. These components are shown in FIGS. 1 and 2.

The control unit 1 is worn attached to a belt or can be placed in a custom belt for easy placement at the waist. The control unit is connected via a cable running under the clothing to a pair of electrodes placed directly on the surface of the skin, the quadriceps in this case. The wrist worn companion device 4 is also shown and can be used for manual activation of cueing.

The unit 1 has a belt clip 10, status LEDs 11, an ON/OFF button 12, and output jacks 14 for stimulus delivery.

Apparatus Architecture and Manual Activation

Figure 3:
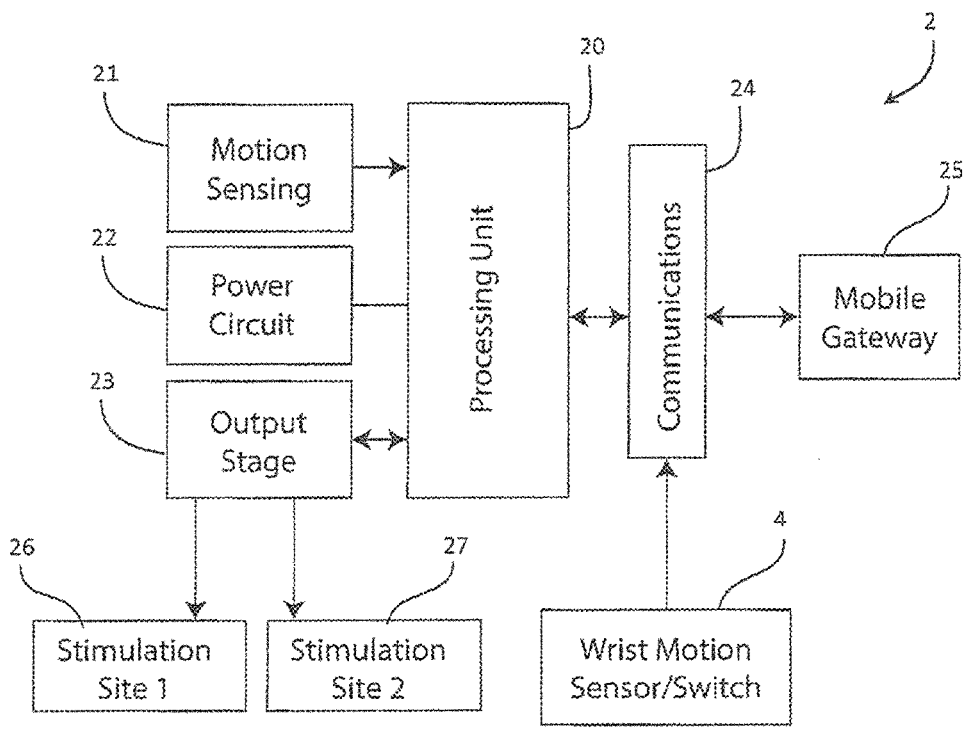
FIG. 3 is a block diagram of the system.

Referring to FIG. 3, the apparatus has a processing unit 20 linked with at least one motion sensor 21, an output stage 23, a communications module 24 and companion devices. The processor 20 uses the motion sensors for gait assessment and manual activation of cueing depending on the configuration.

For gait disturbance detection, the motion sensors 21 capture gait information and the processing unit determines if a gait disturbance (for example a FOG episode) is present. When a gait disturbance is confirmed from the data collected by the motion sensors, electrical cueing is activated. Alternatively manual activation of cueing can be achieved when the motion sensors capture a user specific tapping action on the control unit enclosure, which generates an interrupt signal. The interrupt signal is passed to the processing unit and electrical cueing is activated. Manual activation can also be achieved through the wrist-worn companion device 4. A simple tap or signature motion can be detected at the wrist and wireless transmitted to the processing unit in the waist worn unit whereupon electrical cueing is activated. The wrist worn unit can also be a simple ON/OFF switch, which is pressed by the patient or a capacitive touch sensitive area which is touched by the patient when they require cueing. In its most simple form of cueing, where a body worn unit is used, the apparatus delivers a burst of electrical stimulus to a skin surface site. Typical sites include the skin over the major muscle groups of the lower limbs (FIG. 4), the wrist, or ear lobe.

Lower Limb Stimulation

Figure 4:
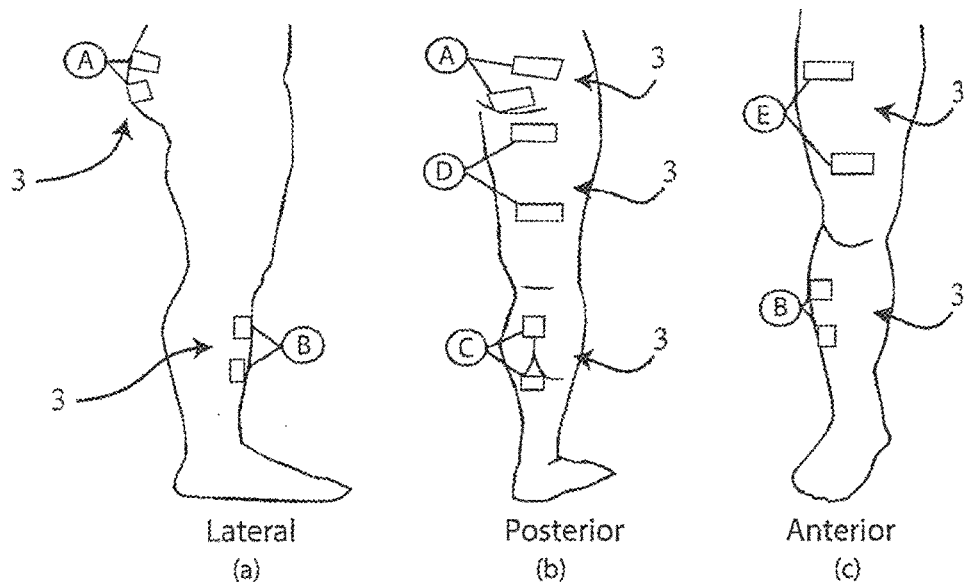
FIGS. 4(a), (b), and (c) are diagrammatic views showing possible locations of surface stimulation electrodes of the system.

FIG. 4 shows electrical stimulation cueing sites of the lower limbs. All electrodes are placed in pairs over the desired muscle group and connected back to the control unit. Muscle groups include, A gluteus maximus, B tibialis anterior, C soleus, D hamstrings and E quadriceps. While the electrodes are placed over the muscle groups, the intention is not to deliver sufficient stimulus to trigger contraction of the muscle, instead stimulus is delivered at an intensity level, which elicits a sensory response. We refer to this specifically as Sensory Electrical Stimulation Cueing, whereas when cueing is achieved through contraction of a muscle and limb movement, we refer to this as Motor Electrical Stimulation Cueing.

Figure 5:
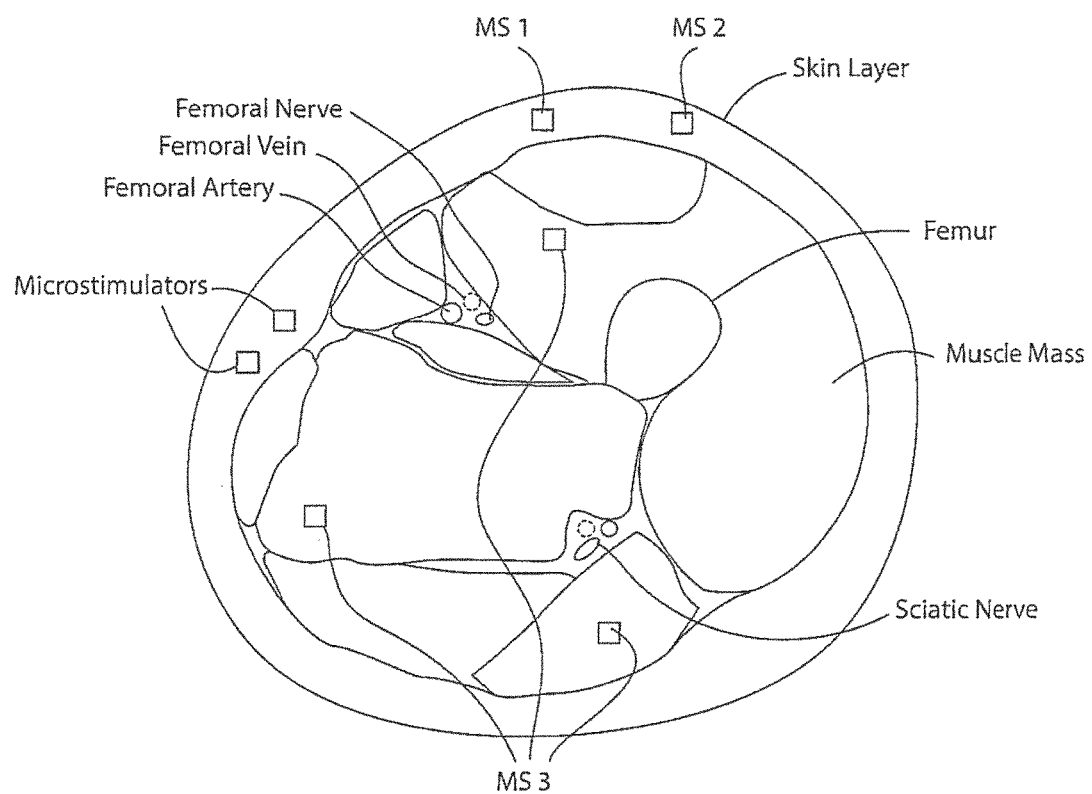
FIG. 5 is a diagram showing a cross-section of a human upper leg with sensory receptors in the skin.

Electrical stimulation can be applied using either surface techniques (electrodes on the skin surface) or implanted techniques (electrodes internal to the body). Electrical stimulation can be applied using two modalities: Motor Electrical Stimulation—the stimulus intensity is of sufficient intensity to trigger activation of motor neurons resulting in muscle contraction or Sensory Electrical Stimulation—the stimulation intensity is of sufficient intensity to trigger activation of sensory neurons giving rise to sensations normally attributed to the activation of sensory end organs—but the stimulation intensity is not sufficient to trigger motor activation. Neural activation from electrical stimulation through depolarization is dependent on the neuron's diameter and its proximity to the stimulation source (FIG. 5). The larger the axon diameter of the neuron, the lower its threshold of excitability, The greater the distance of an axon from the stimulation source the lower the depolarisation current at the neuron site.

Sensory neurons of the skin, while smaller in diameter than motor neurons are normally orders of magnitude closer to the skin surface than the motor nerves. Propagation of current flow from skin surface electrical stimulation electrodes is such that for a given electrical stimulation intensity the level of depolarization will be higher at the more superficial sensory neurons than at the deeper larger motor neurons. As stimulation intensity at the skin surface is increased the nerves associated with the sensory organs fire first—the stimulation intensity at which this occurs may be called the "Sensory Threshold". Continuing to increase the stimulation intensity will eventually result in the deeper motor nerves being triggered—the stimulation intensity at which this occurs is the "Motor Threshold". If the Motor Threshold has been exceeded, then clearly the Sensory Threshold has also been exceeded. Thus when the apparatus carries out motor FES stimulation it is in fact carrying out both motor FES stimulation and sensory FES stimulation.

We have carried out extensive testing of both sensory and motor electrical stimulation cueing in PD patients and it is very well tolerated by PD patients and highly effective as a cueing mechanism.

Motor electrical stimulation results in muscle contraction, and this can be used for two purposes: as a cueing mechanism as the contraction of the muscle and movement of the limb will provide a cue to the user through the mechanism of somatosensory proprioception signals travelling to the CNS from the PNS in response to muscle contraction, and also as a means to move a limb artificially and thus provide a mechanism for gait correction.

The rationale for placing the stimulation electrodes on the skin surface over the muscles is that the electrodes can ultimately have a dual function and when required deliver stimulation at a sensory level for cueing purposes but if required also stimulus can be delivered at a level which will directly via the efferent nerves cause a functional muscle contraction, which may also assist in overcoming gait disturbances using a different modality, for example contraction of the quadriceps muscle to extend the knee if required.

Stimulation Waveform

Figure 6:
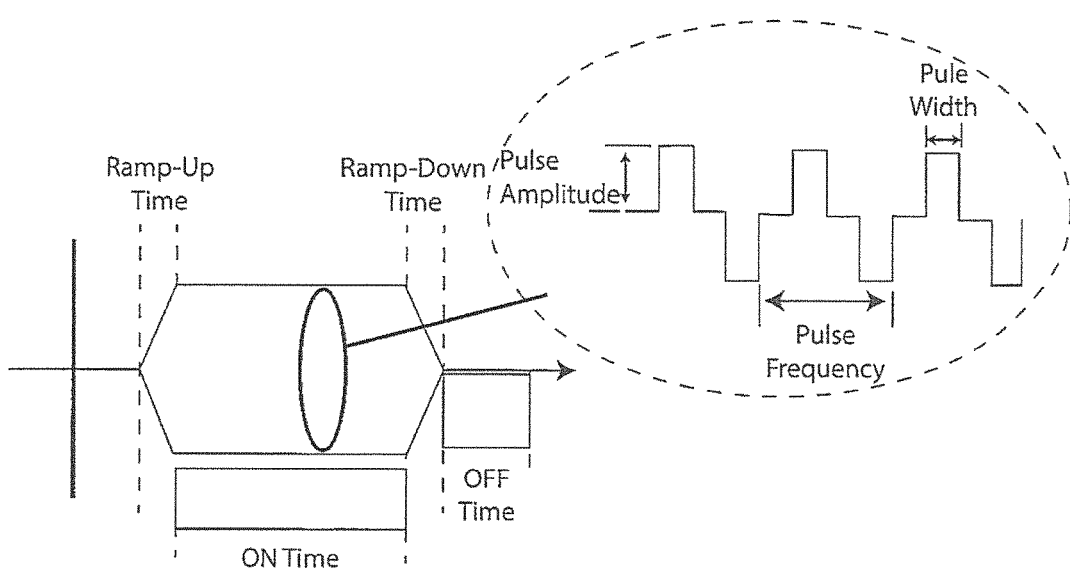
FIG. 6 is a plot illustrating a single electrical stimulation burst.

In some embodiments, for all cases of cueing, bipolar (biphasic) pulse stimulation waveforms are used, which allow for neural stimulation without causing tissue damage. These stimulus waveforms are characterized by three main parameters, pulse frequency, pulse amplitude and pulse width. The waveforms are delivered in short envelope bursts. Each envelope is defined by, Ramp-Up Time, ON Time, Ramp-Down Time and OFF time as shown in FIG. 6. The amplitude, inter-burst frequency and intra-burst pulse frequency can be unique and customized to each user for maximum clinical benefit. Furthermore the inter-envelope frequency and number of bursts can be predefined depending on user requirements.

Typical values are a pulse width of 350 μs, inter-pulse interval of 100 μs, pulse frequency of 36 Hz, and for surface stimulation a maximum stimulation voltage of 68V and for implanted stimulation intensity ranges from 10 μA to 50 mA of stimulation.

All these values are adjustable within defined ranges of appropriate electrical stimulation parameters including but are not limited to: pulse widths ranging from 0 μs up to 1000 μs, inter-pulse intervals ranging from 0 μs up to 1000 μs, pulse frequencies ranging from 0 Hz up to 60 Hz, surface stimulation intensity voltages up to 100V, surface stimulation intensity currents up to 200 mA, implanted stimulation intensity currents ranging from 0 μA to 200 mA, stimulation signals with an stimulation intensity envelope having characteristics of a ramp-up time of up to 1000 ms, an ON time of up to 10,000 ms, a ramp-down of up to 1000 ms, and an OFF time of up to 10,000 ms.

In another embodiment, the ranges are a pulse width of up to 1000 μs, inter-pulse interval of up to 100 ms, pulse frequency of up to 60 Hz and surface voltages of up to 68 V and current of 10 μA to 50 mA. An example envelope has characteristics of a ramp-up time of 100 ms, ON time of 1000 ms, ramp-down of 100 ms, and an OFF time of 100 ms. All of these values are adjustable within defined ranges of ramp-up time of up to 5000 ms, ON time of up to 10000 ms, ramp-down of up to 5000 ms and an OFF time of up to 5000 ms.

Cueing Stimulation Profiles

The various embodiments of the present invention provide a method of correcting gait disturbance, relieving FOG and preventing FOG in a number of configurable setups depending on user preference, capabilities and clinical requirements. The electrical cueing is delivered in one of two modes depending on the configuration and user needs or preference. Stimulation can be delivered in Burst or Continuous mode. Both modes can be manually or automatically activated.

FOG Relief

In one embodiment the user is set up for automatic FOG relief with Burst mode cueing. In this configuration the motion sensor block monitors gait parameters. If FOG is detected, a burst of electrical stimulation of predefined duration is delivered (FIG. 7(A)). In another embodiment, the user is set up for automatic FOG relief and Continuous mode cueing. In this configuration the motion sensor block monitors gait parameters. If FOG is detected a continuous block of electrical stimulation is delivered (customizable frequency, for example 1 burst per second) until the FOG is relieved (FIG. 7(B)).

Figure 8:
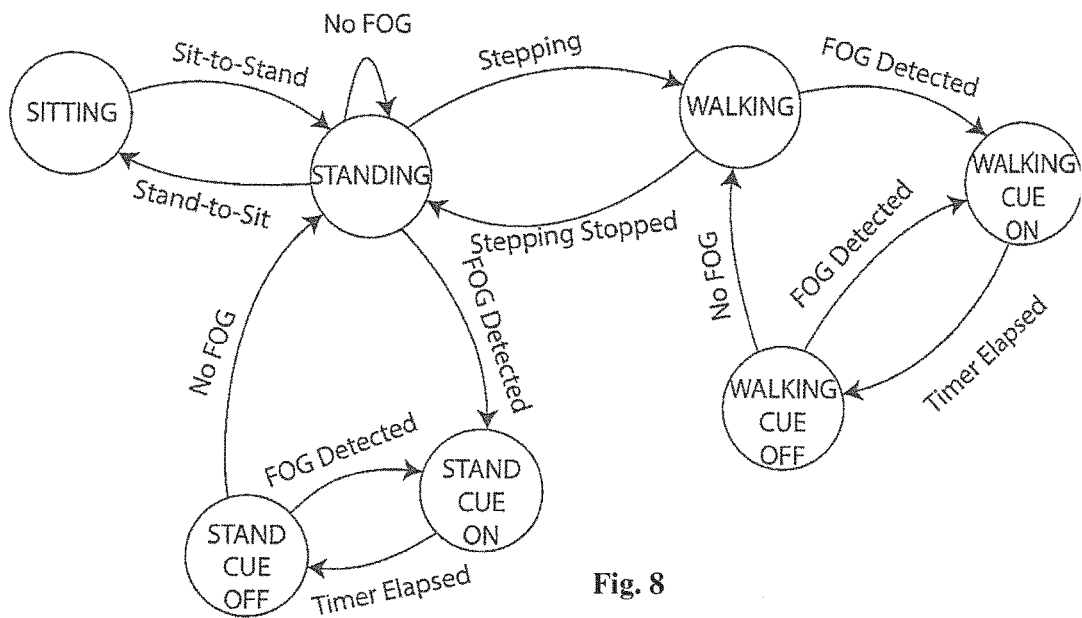
FIG. 8 is a diagram showing state transitions for FOG relief using electrical cueing in which the user starts in the sitting state.

The activation of the cueing system for FOG relief can be represented by a state transition diagram (FIG. 8).

Figure 9:
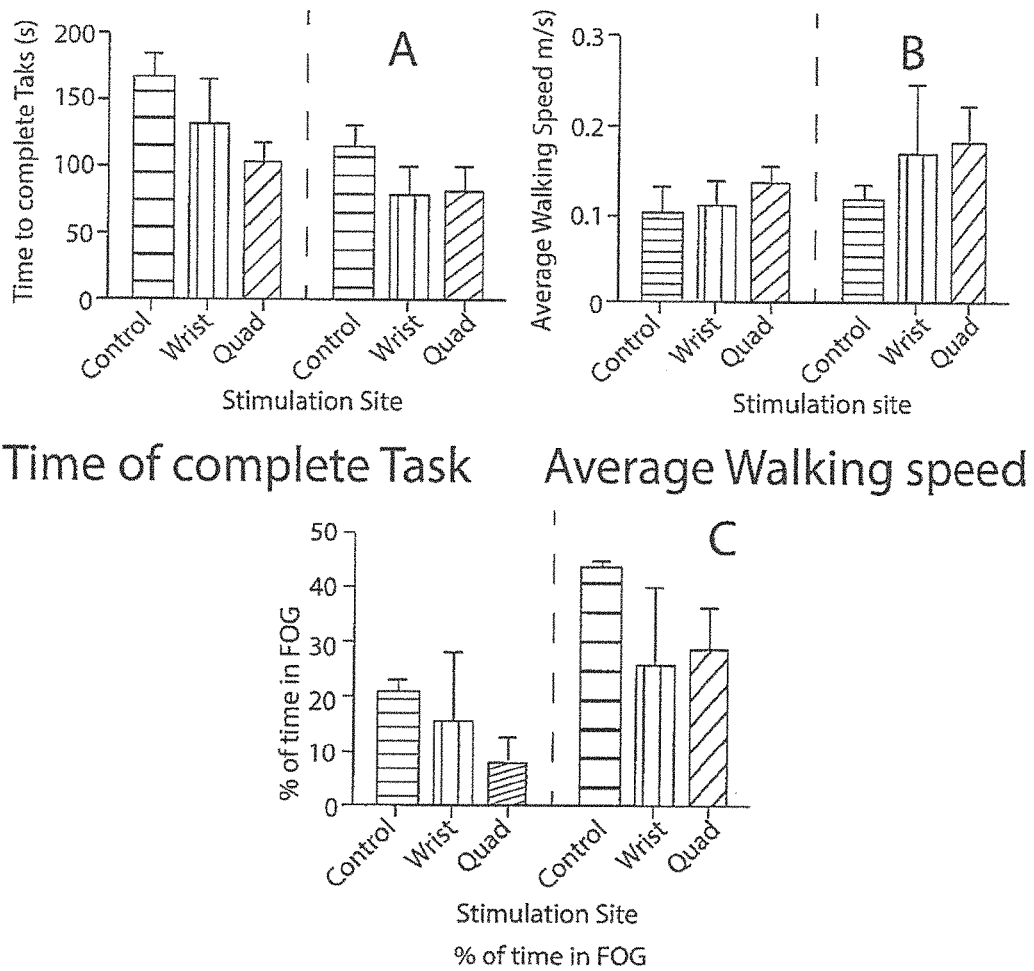
FIG. 9 is a set of plots A, B, and C, in which (A) plots effect of continuous cueing on time to complete a 14 meter walking task where cueing was applied at one of two sites when FOG was detected, (B) plots effect of continuous cueing on average walking speed over a 14 meter walking task where cueing was applied at one of two sites when FOG was detected, and (C) plots effect of continuous cueing on time spent in FOG state over the duration of a 14 meter walking task where cueing was applied at one of two sites when FOG was detected.

In real life testing, continuous cueing for FOG relief has proved very effective in reducing the time to complete a walking task, increasing walking speed and reducing the percentage of time spent in FOG. FIG. 9 (A) shows the effect of continuous cueing on the amount of time taken to complete a 14 meter walking task when cueing was applied at one of two sites when FOG was detected. FIG. 9 (B) shows the effect of continuous cueing on average walking speed over a 14 meter walking task when cueing was applied at one of two sites when FOG was detected. FIG. 9 (C) plots the effect of continuous cueing on the amount of time spent in a FOG state over the duration of a 14 meters walking task when cueing was applied at one of two sites when FOG was detected.

FOG Prevention

FOG prevention can be in one of two modes; Always ON or Adaptive.

In the always-ON embodiment, cueing is applied whenever the user is not seated, standing still or lying. Intention to stand, or walk activates the stimulator and stimulation is applied until the user stops walking as detected by the gait sensor block in the control unit device (FIGS. 11 and 12).

Figure 10:
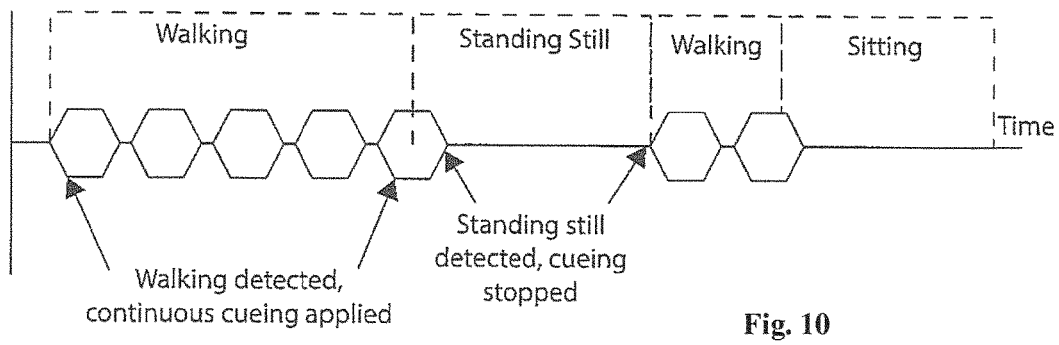
FIG. 10 is a plot illustrating always-on cueing.

FIG. 10 shows always-ON cueing. A continuous cue is applied in response to walking being detected and when the user is not standing or sitting. The frequency of waveform delivery is customizable.

Figure 11:
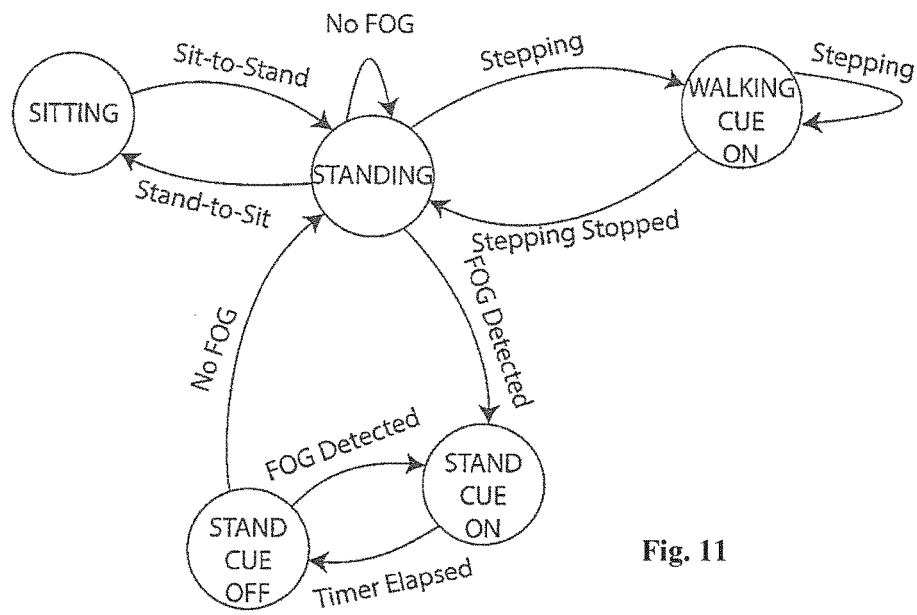
FIG. 11 is a state diagram for always-on operation.
Figure 12:
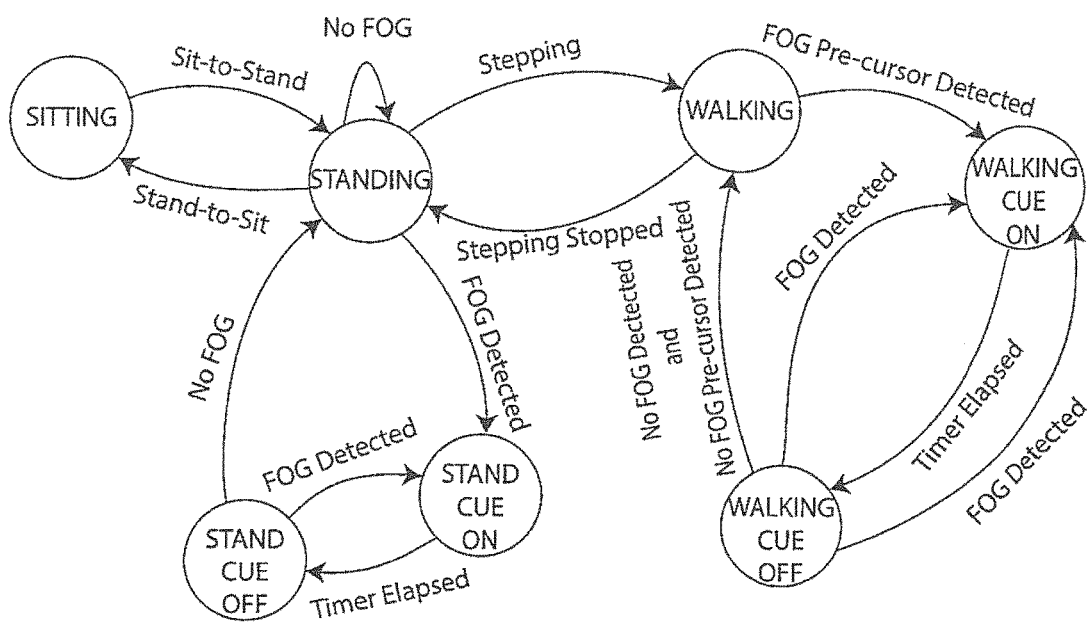
FIG. 12 is such a diagram for adaptive cueing.

FIG. 11 shows a FOG prevention, always-ON cueing state transition diagram. A continuous cue is applied in response to walking being detected and when the user is not standing or sitting. If the user enters a FOG state cueing is delivered in the absence of stepping. The frequency of waveform delivery is customizable.

In another embodiment, cueing (adaptive) involves activation to prevent FOG only in response to alterations in gait dynamics or detection of a FOG pre-cursor, cueing delivery can be Continuous or Burst until the gait correction is achieved. This adaptive type of cueing is an alternative to always-on cueing in cases where the user does not require or wish to have continuous cueing. Signals received from the gait sensors automatically control stimulus delivery (FIG. 12).

FIG. 12 shows a FOG prevention Adaptive cueing state transition diagram. A cue (Continuous or Burst) is applied only when the user is walking when a FOG pre-cursor is detected. If the user enters a FOG state cueing is delivered. The frequency of waveform delivery is customizable.

Additional Embodiments Depending on Peripherals

The apparatus uses electrodes placed either on the surface of the skin or implanted just below the skin surface and requires no third party devices (FIGS. 13, 14, 15, and 16). The invention could be effective using third party gait or tremor sensors to detect gait disturbances. A disturbance in gait can be transmitted to the control unit wirelessly and appropriate stimulation delivered. Additionally third party physiological sensors for heart rate and autonomic nervous system and EEG activity can be used to detect impending FOG events and transmit this information to the control unit wirelessly and appropriate stimulation can be delivered.

Additionally, a complete or partially implanted solution could be adopted. In the partially implanted embodiment a stimulator device could be minimally implanted at appropriate sites and the surface control unit worn at the waist (communicating wirelessly with the implant).

Additionally, sensors could also be implanted and again the sensors are communicating with the surface control unit on the gait status of the patient, which triggers activation of implanted stimulator devices. Additionally, a fully implanted approach could be used where stimulator, controller and sensors could be implanted. The sensors could be used to detect both EMG and provide inertial sensing, giving information on muscle activation and movement, providing a basis for sensing movement, intention to change posture, normal gait and gait disturbance.

Figure 13:
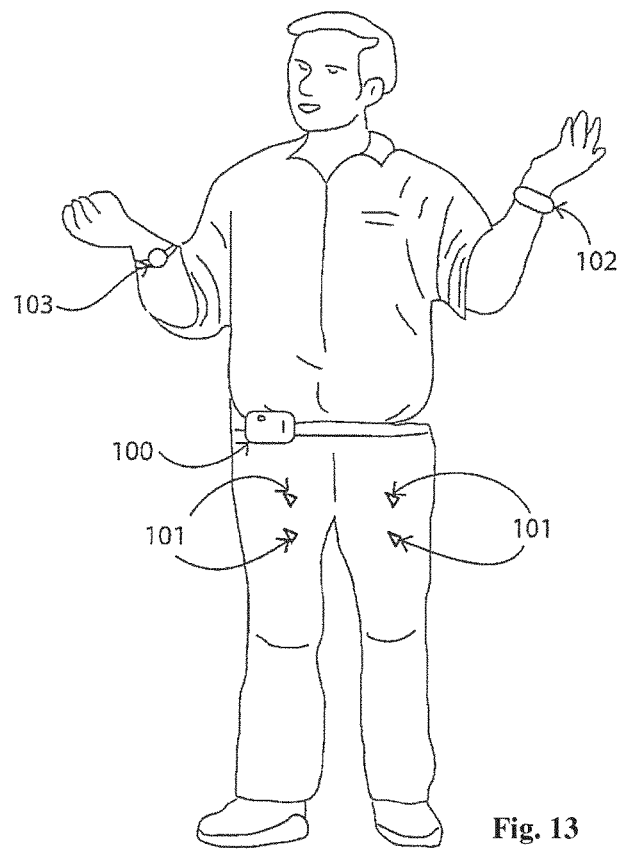
FIG. 13 illustrates wearing of components of an alternative system of the invention.

FIG. 13 shows a control unit 100 being worn attached to a belt or can be placed in a custom belt for easy placement at the waist. There are implanted stimulator devices 101, gait sensors 102, and physiological sensors 103.

Figure 14:
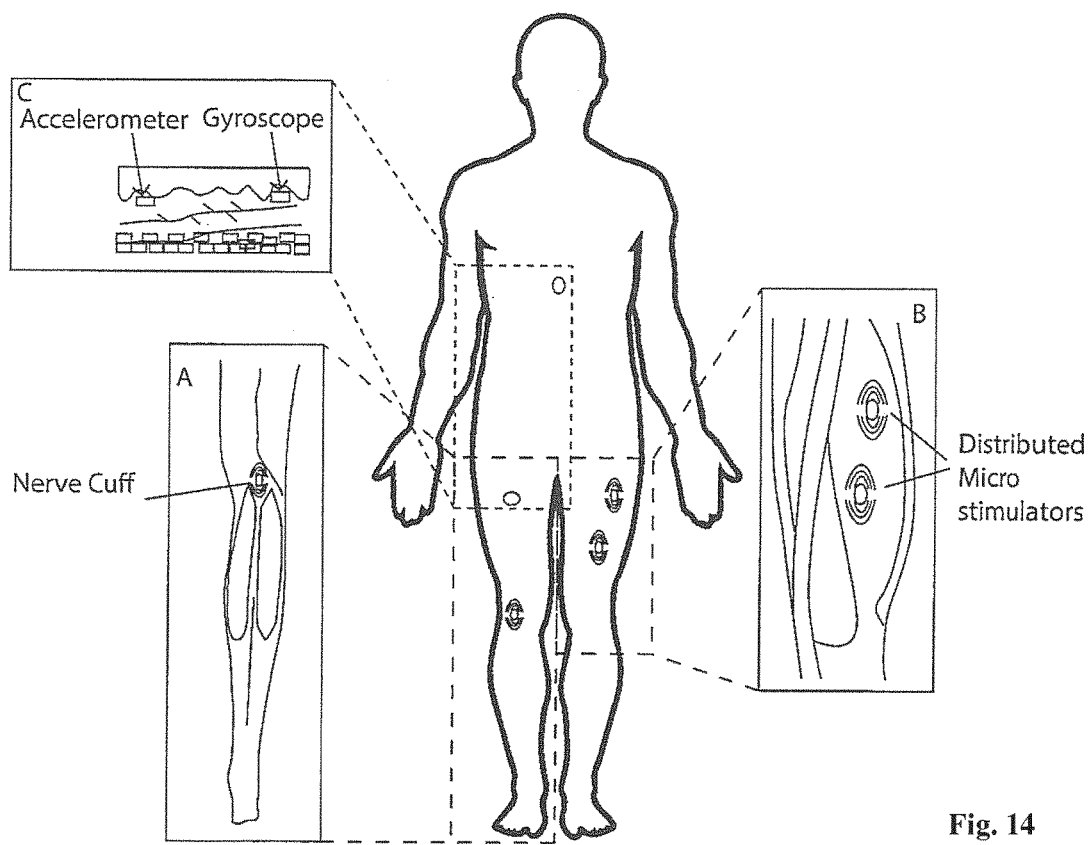
FIG. 14 shows electrical stimulation sites for implanted electrical stimulation cueing.

FIG. 14 is an example of an implanted sensing and cueing arrangement, in which (A) shows use of a nerve cuff electrode for sensory or motor activation, and (B) shows distributed micro-stimulation for sensory or motor activation, and (C) shows implanted distributed sensing for motion sensing.

Figure 15:
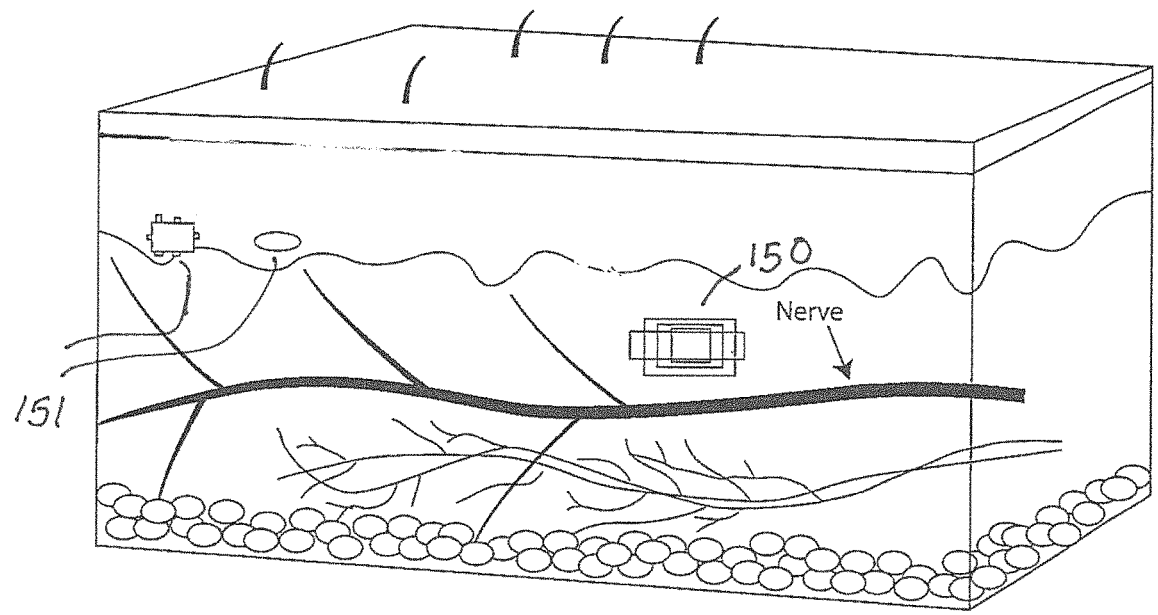
FIG. 15 shows a representation of implanted distributed micro-stimulators and micro-sensor (for motion sense capture) in a cross section of skin, in which the location could be from any appropriate anatomical site on the body suitable for implantation.

FIG. 15 shows an example of the relative position of a distributed micro-stimulation device 150 in the skin compared to underlying nervous tissue. Also shown is an implanted motion sensing unit 151 for motion sense capture (accelerometer or gyroscope). The implantation site for the stimulator device could be any site on the body appropriate for implantation. The implantation site for the motion sense device would be any site on the body appropriate for implantation and gait/posture detection.

Figure 16:
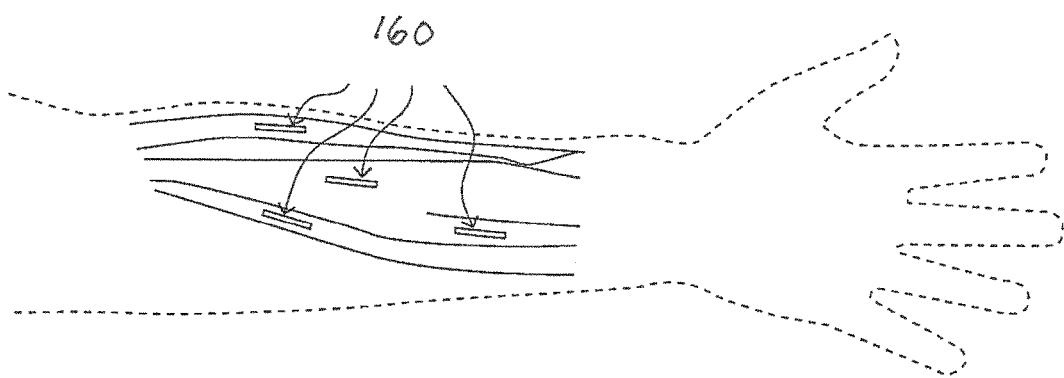
FIG. 16 is a representation of distributed electrical stimulation sites in the forearm, but the location could alternatively be from any appropriate anatomical site on the body suitable for implantation.

FIG. 16 is an example of distributed micro-stimulation setup for sensory or motor activation in the forearm using a BION type stimulation device 160, this arrangement could be employed at any appropriate anatomical site.

Examples of Manual Activation

The cueing system can be activated automatically using the motion sensing block in the control unit or external gait sensors as described previously. Manual activation of the cueing is based on the generation of an interrupt by the motion sensing block in response to a double tap on the control unit enclosure by the patient or using the wrist worn companion device (FIG. 17).

For FOG relief the system is only active when a FOG event occurs. Electrical stimulation can be initiated in one of three ways. 1. By the user tapping directly on the control unit enclosure. This embodiment would deliver burst mode stimulus only. 2. By the user activating a wrist-worn companion device/switch, which is connected to the control unit wirelessly. In this embodiment pressing or tapping the companion device/switch in a customizable fashion can initiate activation. Additionally activation can be initiated based on an algorithm in the companion device detecting specific actions (motion sense) of the wrist, by user preference the stimulation mode can be continuous or burst in nature.

Figure 17:
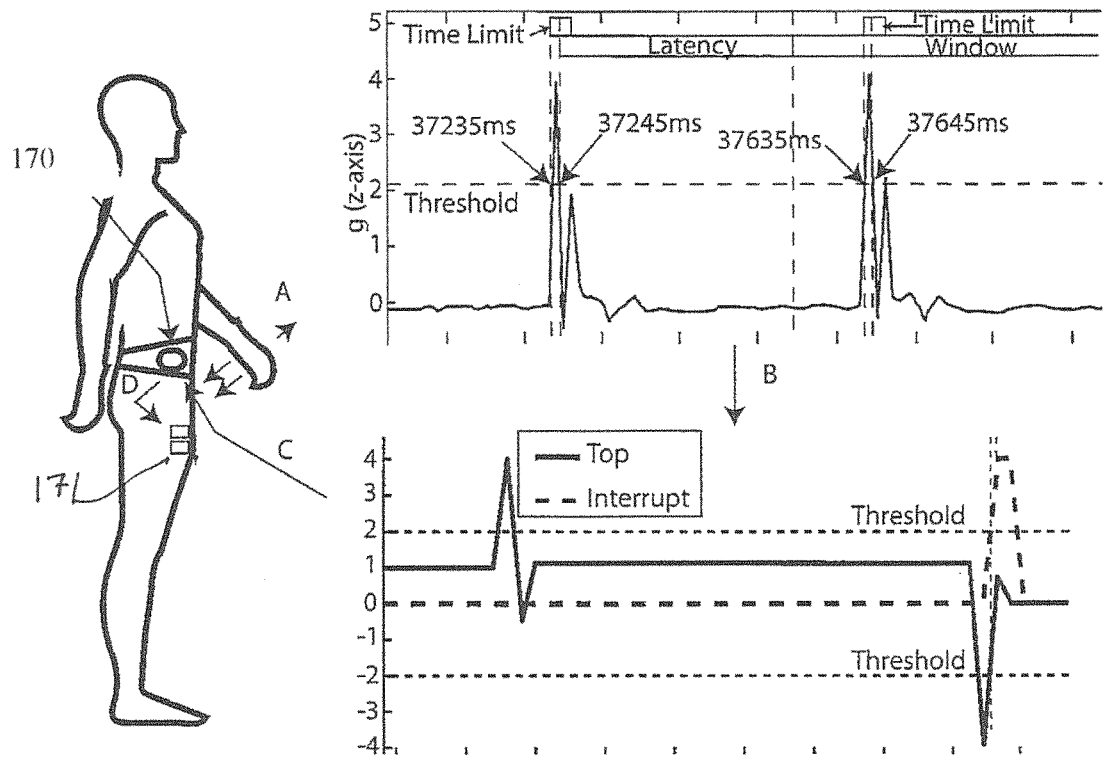
FIG. 17 is a diagram with plots for (A) user enters FOG state and performs a double-tap on the control unit, which is identified by the motion sensor block in the control unit; (B) an interrupt is generated in response to an identifying double tap, and (C) an interrupt is sent to the control unit electrical output stage block to deliver stimulus, and (D) Stimulus is delivered at the electrode site.

FIG. 17 shows manual activation of stimulation by a double-tap on a device enclosure 170. The user enters FOG state and performs a double-tap A on the control unit 170; B, an interrupt is generated in response to identifying a double tap; and C an interrupt is sent to the control unit electrical output stage block to deliver a stimulus; D, Stimulus is delivered at the electrodes 171.

Figure 18:
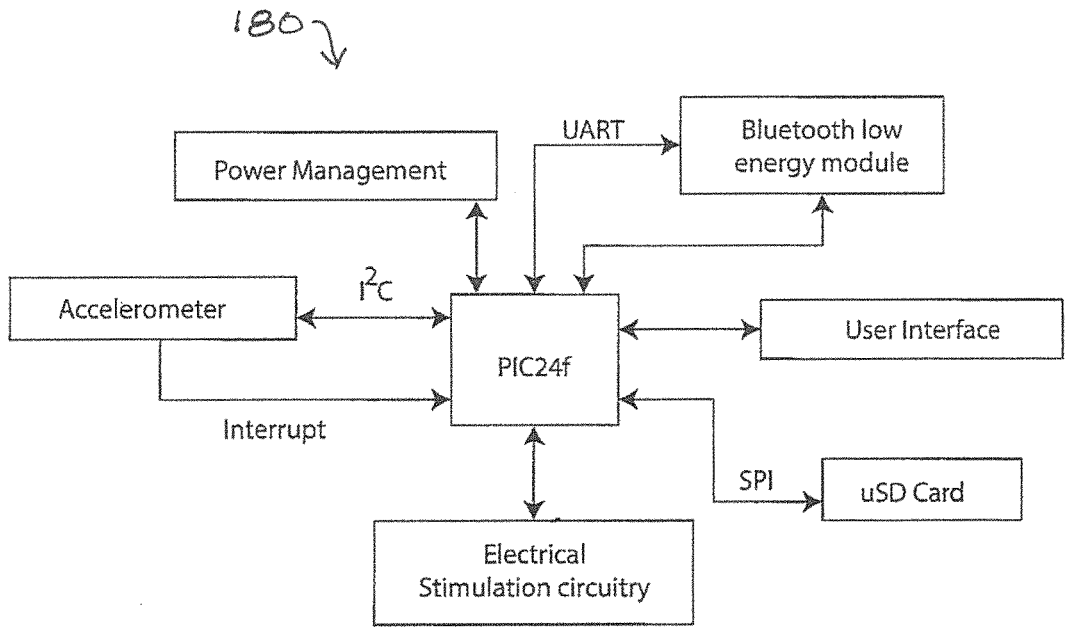
FIG. 18 is a system architecture diagram and FIG. 19 is a more detailed architecture diagram.
Figure 19:
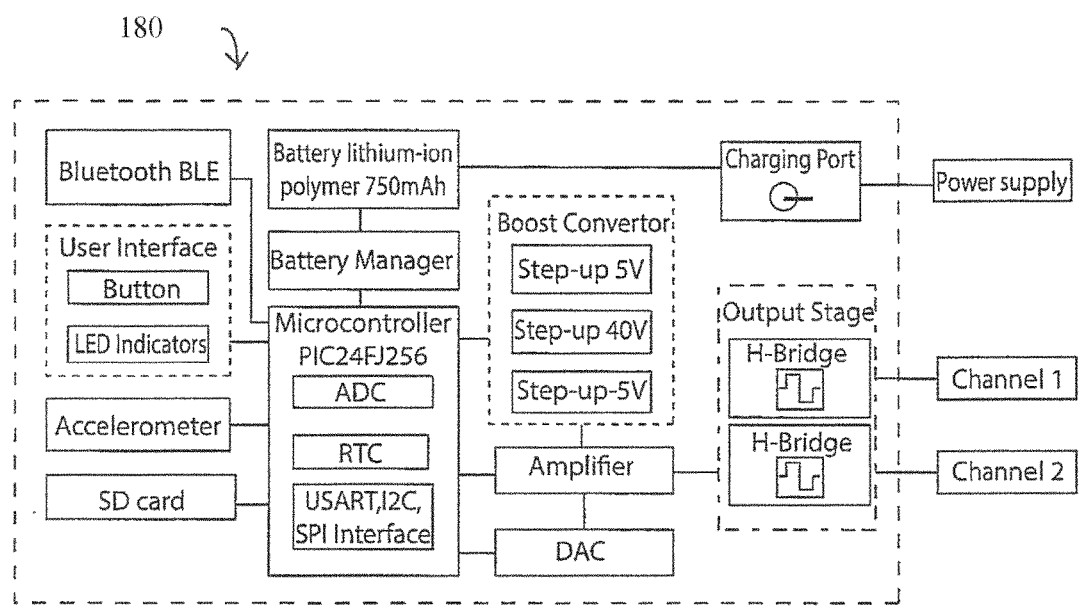

The architecture of a system 180 of one embodiment is shown in FIGS. 18 and 19, in which the controller is a PIC24F processor linked with a power management circuit, an accelerometer motion sensor, electrical stimulation circuitry, a μSD card, a user interface, and a Bluetooth module.

Stimulus Amplitude

The stimulus when delivered by the system is above the user's sensory threshold but below their motor threshold. Thus, the user feels the sensation on their skin but muscle contraction is completely under voluntary control. However, in another embodiment the amplitude of the electrical stimulus could be set sufficiently high so as to achieve a muscle contraction. Thus, the system can deliver sensory cueing and motor cueing. Motor cueing can be employed in a number of scenarios including for step initiation, more aggressive cueing for FOG relief and guidance around objects in the walking pathway. Motor cueing is controlled and activated in a similar manner to sensory cueing.

Example Uses

Table 1 below shows the surface electrical stimulation parameter values which were demonstrated to be highly effective in FOG relief (25% reduction in time to complete a walking task) and FOG prevention (43% reduction in time to complete a walking task) when used during testing on patients with Parkinson's disease using skin surface electrodes on the skin surface of the hamstrings muscle as the site for the electrode pair and when cutaneous multi-modal somatosensory stimulation was applied. The apparatus used was that illustrated in FIGS. 1 and 2 with the electrode position being position D in FIG. 4(b).

TABLE 1

| Stimulation Parameters | FOG Relief mode | FOG Prevention mode |
| --- | --- | --- |
| Stimulation Intensity Voltage | 10-25 V | 10-25 V |
| Pulse Frequency | 36 Hz | 36 Hz |
| Pulse Width | 350 μs | 350 μs |
| Inter-Pulse Interval | 100 μs | 100 μs |
| Ramp-Up Time | 100 ms | 100 ms |
| ON Time | 1000 ms | 500 ms |
| Ramp-Down Time | 100 ms | 100 ms |
| OFF Time | 200 ms | 0 ms (gait cycle time 0.7 s) |

Table 2 below provides representative raw data on the performance of the FOG Relief and FOG Prevention ES versus No ES for two patients with Parkinson's disease. Two outcome measures were used: the number of FOG events occurring during a specified walking task and the time to complete this walking task. It is clear that FOG Relief and FOG Prevention both provide very significant improvements in these outcome measures when the stimulation parameters of Table 1 were applied.

TABLE 2

| Gait Parameters | No ES Patient 1 | FOG Relief Patient 1 | FOG Prevention Patient 1 | No ES Patient 2 | FOG Relief Patient 2 | FOG Prevention Patient 2 |
|---|---|---|---|---|---|---|
| No of FOG Events | 6 | 3 | 0 | 13 | 8 | 6 |
| Time to Complete Walking Task | 82.54 s | 73.13 s | 59.10 s | 139.6 s | 109.9 s | 85.36 s |

For the performance data in Table 2, FOG Relief ES was initiated by the patient self-activating the delivery of stimulus by performing a double-tap action on the surface of the device enclosure with their hand as illustrated in FIG. 17. This double tap action is detected by an on-board accelerometer (ST Microelectronics LIS2DH™ device was used) and an interrupt was generated by the accelerometer device, provided the double tap 'characteristics' matched the programmed settings in the accelerometer. This interrupt was used to trigger deliver of stimulus.

Table 3 below lists the programmed accelerometer double tap parameters successfully used for the FOG Relief results shown in Table 2 and which are illustrated in FIG. 17. There are four LIS2DH accelerometer double tap parameters, which must be customised to the unique needs of persons with Parkinson's disease due to the speed at which they are typically capable of executing a double tap (typically slower than persons without PD) and due to the force at which they are capable of performing a double tap (typically lower forces than persons without PD).

The first double tap parameter is the Latency (FIG. 17), which is the minimum time which must elapse between the first and the second tap being performed. The second double tap parameter is the Threshold, which is the minimum acceleration which must be detected before the acceleration spike is recognised as a tap. The values given use the unit "g", in which 1 g=9.81 m/s.sup.2, the force of the tap being detected as an acceleration on the accelerometer. In general the preferred range is 5 m/s.sup.2 to 100 m/s.sup.2. The third double tap parameter is the Time Limit, which is the maximum time which can elapse from the acceleration signal exceeding the Threshold to returning below the Threshold. The fourth double tap parameter is the Window, which is the time after the Latency, by which time the second tap must have crossed the Threshold.

The values for these parameters that will be effective with persons with Parkinson's disease have to be determined through experimental means by testing with this patient group. We have carried out this testing.

TABLE 3

| Double Tap Parameters | Accelerometer Double Tap Parameters Range | Value Used in FOG Relief Testing (Table 2 data) |
|---|---|---|
| Latency | 0-635 ms | 175-185 ms |
| Threshold | 2-8 g | 3 g |
| Time Limit | 0-1270 ms | 25 ms |
| Window | 0-1270 ms | 340 ms |

Stimulus Modulation Strategy for Both FOG Prevention and FOG Relief

As described above the controller can dynamically change its mode of operation according to conditions. Examples are "always on", "adaptive", "continuous" and "burst". In various embodiments the controller is programmed to modulate stimuli in real-time using a close loop technique and three dimensional stimulus spaces, an example for cutaneous multi-modal somatosensory electrical stimulation is shown in FIG. 24 and an example for motor multi-modal somatosensory electrical stimulation is shown in FIG. 25.

The controller functions as follows: The stimulus effect can be considered to be the effect of three independent stimulation parameters working together to increase or decrease the effect of the electrical stimulus: Stimulus Intensity Voltage, Ramp Up Time, Pulse Frequency. Two points in stimulus parameters 3D space are identified: the lowest stimulus values considered to work for multi-modal somatosensory electrical stimulation (Stimulus Intensity Voltage 10V, Ramp Up Time 0.4 s, Pulse Frequency 40 Hz) and the highest stimulus values that will maintain the stimulus as non-motor and still function as multi-modal somatosensory electrical stimulation (Stimulus Intensity Voltage 30V, Ramp Up Time 0.0 s, Pulse Frequency 20 Hz). These two points in 3D stimulus space are two diagonally opposite points in a cube as shown in FIG. 24.

The controller is programmed to modulate stimulus intensity by moving along a stimulation modulation profile line from the point of lowest intensity to the point of highest intensity. By using this line, which combines the adjustment of three parameters simultaneously, a more effective and efficient modulation of stimulus is achieved. By way of example, stimulus could be modulated using a 10 s window but the window size could be adjusted to other values to optimize the performance of the controller.

Advantageously, the line may follow any suitable curve according to combinations of the parameters contributing to it. Such relative combinations will vary from patient to patient, and the shape of the line may be pre-set as part of the patient characteristics.

The stimulation modulation profile line is divided into 100 steps from the minimum stimulus point to maximum stimulus point (a larger step number could be adopted, this number being presented by way of example FOG Prevention With the 10 s window, the controller measures the percentage of time the patient was in FOG for the previous 10 s and modulates the stimulus to be used for the next cycle on the basis of this measurement using the flow-chart of FIG. 26.

The patient is detected to be walking, cueing is turned on in the FOG Prevention mode at the lowest stimulus point on the stimulation modulation profile line. If during the previous 10 s cycle, the FOG incidence was less than or equal 12.5%, then the stimulus parameter point on the stimulation modulation profile line is unchanged. If during the previous 10 s cycle, the FOG incidence was greater than 12.5% and less than or equal 25%, then the stimulus parameter point on the stimulation modulation profile line is incremented by 5 points. If during the previous 10 s cycle, the FOG incidence was greater than 25% and less than or equal 50%, then the stimulus parameter point on the stimulation modulation profile line is incremented by 10 points. If during the previous 10 s cycle, the FOG incidence was greater than 50%, then the stimulus parameter point on the stimulation modulation profile line is incremented by 20 points.

This process is continuously repeated each 10 s cycle with the stimulus point moving along the stimulation modulation profile line as required based on the effectiveness (as measured by the percentage of time in FOG) of the stimulus preventing FOG during the previous cycle.

The rationale for this modulation strategy is that: at low levels of FOG (12.5%<FOG 25%) the controller adopts a conservative approach in trying to eliminate the low levels of FOG through the gradual increase in stimulus effect, the small increment step here of 5 points gives scope to use twenty 5 increments steps along the stimulation modulation profile line in our efforts to eliminate FOG. At medium levels of FOG (25%<FOG 25%) there is a less conservative approach in trying to eliminate this medium level of FOG through a larger more aggressive increase in stimulus effect to counter the more frequent FOG. The increment step here of 10 points gives scope to use ten 10 increments steps along the stimulation modulation profile line to eliminate FOG. At high levels of FOG (25%<FOG 25%) there is a very aggressive approach in trying to eliminate this high level of FOG through a much larger aggressive increase in stimulus effect to counter the more frequent FOG. The increment step here of 20 points gives scope to use five 20 increments steps along the stimulation modulation profile line to eliminate FOG.

In all cases, stimulus intensity is modulated by moving along the stimulation modulation profile line from the point of lowest intensity to the point of highest intensity. By using this line, which combines the adjustment of three parameters simultaneously, a more effective and efficient modulation of stimulus is achieved.

FOG Relief

Prior to using the device, the patient first selects if stimulus will be incremented along the stimulation modulation profile line by 5, 10 or 20 increments with each repeated application of stimulus if FOG persists.

The patient is walking and FOG is detected and a burst of cueing is activated at the lowest stimulus point on the stimulation modulation profile line.

If after 5 s (other time periods could also be used), FOG still exists, then the stimulus parameter point on the stimulation modulation profile line is incremented by the preselected step point (5, 10 or 20 steps) and another burst of stimulus is applied.

This process is continued until either FOG ends or the end point of the stimulation modulation profile line is reached.

The rationale for this modulation strategy is that the patient decides on how aggressively stimulus will be increased to relieve FOG if it persists. Stimulus intensity is modulated by moving along the stimulation modulation profile line from the point of lowest intensity to the point of highest intensity. By using this line, which combines the adjustment of three parameters simultaneously, a more effective and efficient modulation of stimulus is achieved.

It will be appreciated that the invention is capable of operating effectively in environments with rapidly varying noise levels and in environments with rapidly varying light levels.

For PD patients FOG is a sudden, involuntary, and transient block in gait, typically occurring at gait initiation, turning, approaching targets, and passing narrow doorways and manifests as moving forward with very small steps, leg trembling in place, or total akinesia. The quality of life of patients is seriously affected by FOG, because it results in an unpredictable loss of control over movement and often results in falls, which are a major cause of hospitalization for PD patients. Our invention makes FOG relief and prevention feasible, unobtrusive with minimum burden on the patient and has wide application in almost any environment both inside and outside the home.

Cueing

Cueing can be delivered using either prevention mode, where stimulus is delivered in a cyclic, continuous manner to either prevent or mitigate FOG episodes from occurring or can be delivered in relief mode, where stimulus is delivered in a burst or bursts of stimulation, when a FOG episode is detected (these cueing types are described in Table 4 below), either automatically via a system of sensors, comprising one or more sensing elements or manually by the user or another person to relieve that FOG episode.

TABLE 4

Cueing Types

| Cueing Type # | Description of Cueing Type | Intended Use of Cueing |
| --- | --- | --- |
| 1. | Cueing can be delivered as a rhythmic, repetitive series of cues (bursts of stimulus) whose delivery is synched in some manner to the walking cadence of the person, and which are delivered each stride on a continuous basis or for a limited duration of time. | This form of cueing could be used to prevent, mitigate, or relieve FOG. |
| 2. | Cueing can be delivered as a rhythmic, repetitive series of cues (bursts of stimulus) whose delivery is synched in some manner to the walking cadence of the person, and which are delivered to predetermined or to a random number of strides on a continuous basis while the person is walking or intending to walk. | This form of cueing could be used to prevent, mitigate, or relieve FOG. |
| 3. | Cueing can be delivered in response to a detected activity or gait event as a rhythmic, repetitive series of cues (bursts of stimulus) whose delivery is synched in some manner to the walking cadence of the person, and which are delivered in this rhythmic manner for an appropriate duration. | This form of cueing could be used to relieve FOG. |

TABLE 4-continued

Cueing Types

| Cueing Type # | Description of Cueing Type | Intended Use of Cueing |
| --- | --- | --- |
| 4. | Cueing can be delivered as one or more bursts of stimulus, in response to a detected activity or gait event. | This form of cueing could be used to relieve FOG. |
| 5. | Cueing can be delivered as one or more bursts of stimulus at regular or irregular intervals of time. | This form of cueing could be used to prevent or mitigate FOG. |
| 6. | Cueing can be delivered during walking as a rhythmic, repetitive series of cues (bursts of stimulus) whose delivery is synched in some manner to the walking cadence of the person, and which are delivered to a predetermined or to a random number of strides on a continuous basis while the person is walking. Additionally, cueing can also be delivered at other times as one or more bursts of stimulus at regular or irregular intervals of time. | This form of cueing could be used to prevent or mitigate FOG. |

The system may switch between cueing type between and of the types 1 to 6 listed above in a predetermined or randomised order on detection of the lessening of cue effectiveness or on manual input.

Bilateral Cueing

Bilateral cueing is the process of providing cues to both sides of a patient's body, for example to initiate and/or maintain walking. Bilateral cueing is achieved using multiple cueing sites, with at least one site on the left half of the mid-sagittal plane of the body and at least one site on the right half of the mid-sagittal plane of the body. For example, cueing sites may be the left and right thighs, the left and right lower legs, the left and right lower arms, the left and right upper arms, or the left and right wrists.

A gait management apparatus for providing bilateral cueing may comprise at least one cueing actuator. The at least one cueing actuator includes at least one stimulation apparatus configured to be disposed at one or more cueing sites on each side of a patient's body to provide bilateral stimulation. The gait management apparatus may also comprise a memory for storing a non-transitory computer program, and a controller programmed to execute the program to allow the controller to activate cueing. The at least one cueing actuator, the memory and the controller are in electrical contact with one another.

There are a number of different possible approaches for how to arrange the cueing sites to achieve bilateral cueing. Some of these are explained below with reference to FIGS. 27a-d.

Figure 27A:
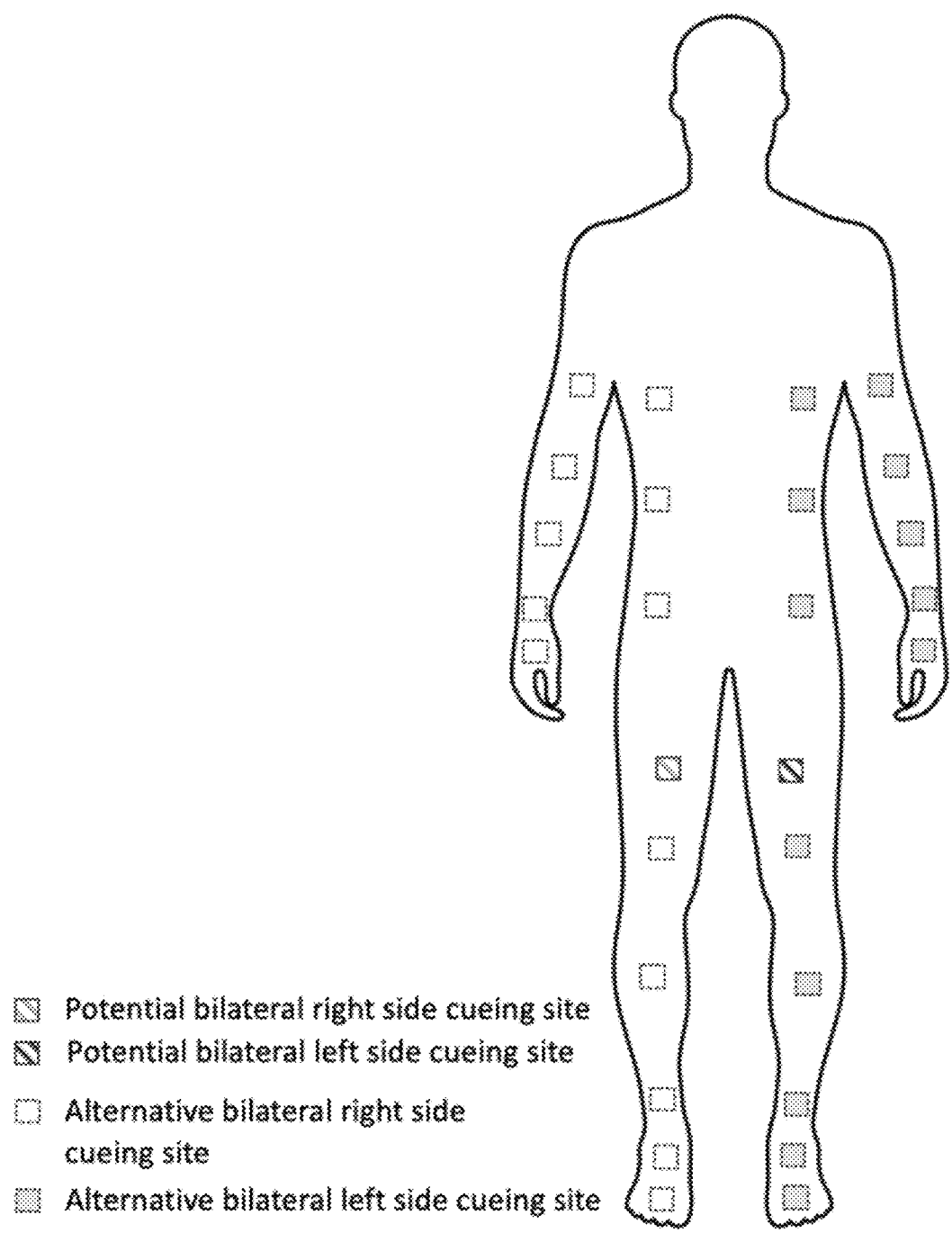
FIGS. 27A-D are diagrams illustrating possible cueing sites for bilateral cueing.

A first approach is shown in FIG. 27a, where a single cueing site is utilised for the left side and a single cueing site is utilised for the right side. There are multiple possible locations for these left-side and right-side sites. A number of possible sites illustrated are by way of example only.

Figure 27B:
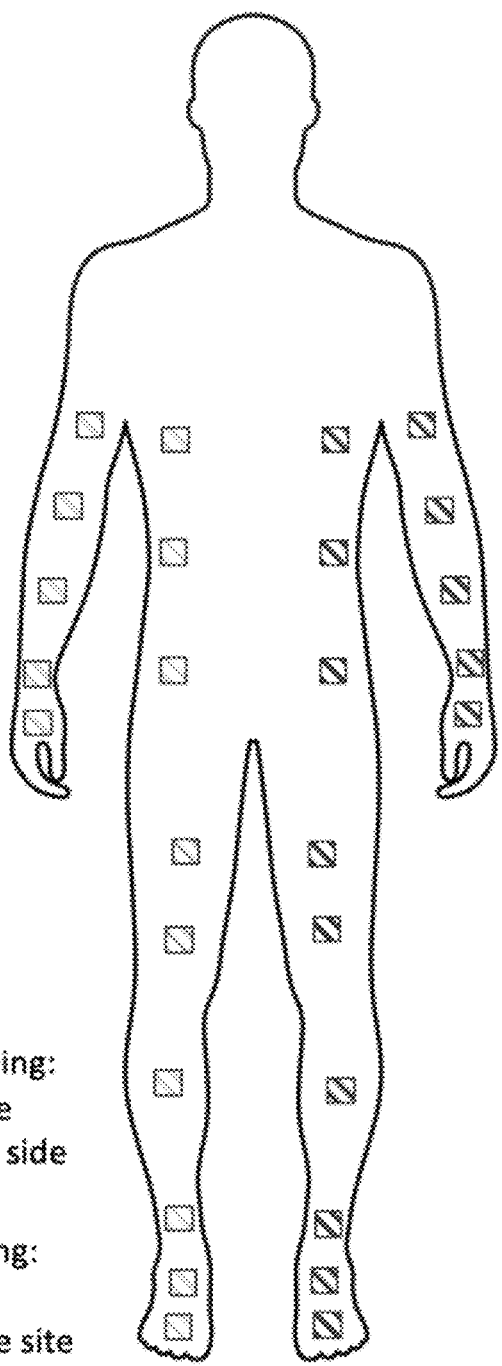

A second approach is shown in FIG. 27b, where multiple cueing sites are adopted for the left side and multiple cueing sites are adopted for the right side. Each cueing site on the left side can be independent from the other sites on the left side. Each cueing site on the right side can be independent from the other sites on the right side. Alternatively, the left sites can be activated together or with a specific relationship to each other, and the right sites can also be activated together or with a specific relationship to each other. For example, stimulation could be activated sequentially at different sites on a patient's leg. In one embodiment, cueing sites may be located on a quadriceps, a shank and a foot of the user. Stimulation may be applied sequentially starting with the quadriceps, then subsequently to the shank and finally to the foot. In another embodiment, multiple cueing sites may be located on each of a quadriceps, a shank and a foot of the patient. Stimulation may be applied at a quadriceps site near the hip, then a quadriceps site near the knee, followed by a shank site near the knee, then a shank site near the ankle, followed by a foot site near the ankle and finally a foot site near the mid-foot. More generally, the stimulation could be applied as a wave of stimulus starting at one cueing location on the patient and travelling towards another cueing location on the patient, for example from the upper thigh downwards towards the foot. Stimulation may be activated at each cueing site in anatomical order. The sites illustrated are presented by way of example, other sites would also be possible.

Figure 27C:
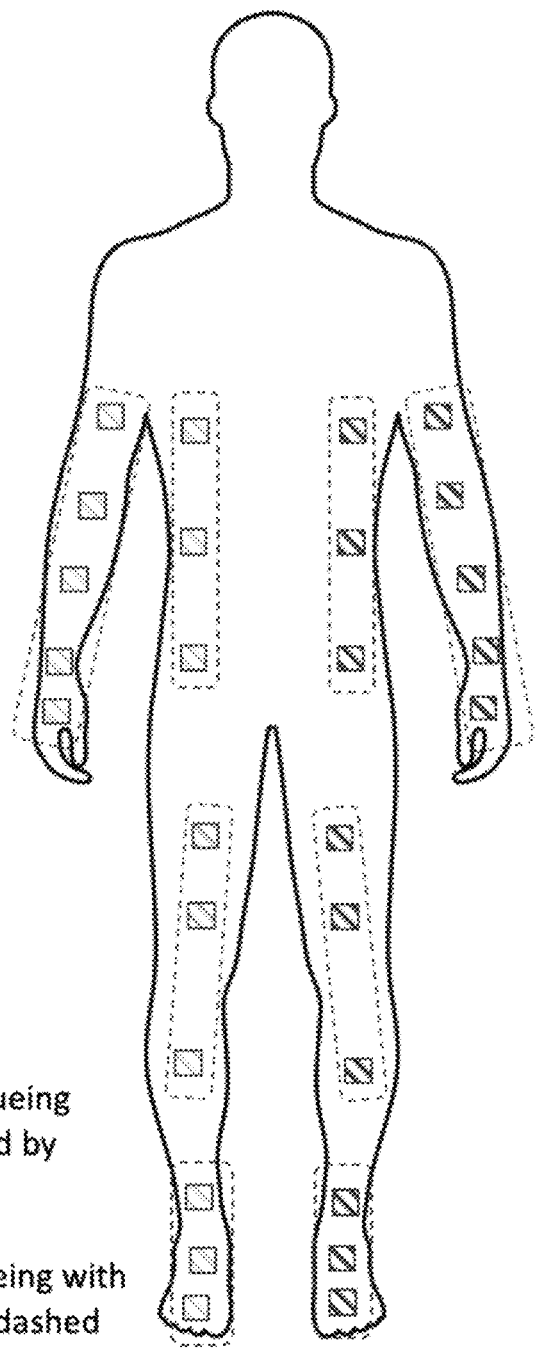

A third approach is shown in FIG. 27c, where multiple cueing sites are adopted for the left side and multiple cueing sites are adopted for the right side. In this setup, these multiple sites on the left side and multiple sites on the right side are composed of several groupings, where the sites in each grouping work in unison. The sites in one grouping can be independent from the other sites in other groupings. Alternatively, there may be a relationship between the activity of sites in one grouping and the activity of sites in a different grouping. For example, stimulation could be activated sequentially at different groups of sites on a patient's leg. In one embodiment, groups of cueing sites may be located on a quadriceps, a shank and a foot of the user. Stimulation may be applied sequentially starting with the quadriceps group of sites, then subsequently to the shank group of sites and finally to the foot group of sites. More generally, the stimulation could be applied as a wave of stimulus starting at one group of cueing locations on the patient and travelling towards another group of cueing locations on the patient, for example from the upper thigh downwards towards the foot. Stimulation may be activated at each group of cueing sites in anatomical order. The groupings illustrated are presented by way of example, and other groupings would also be possible.

Figure 27D:
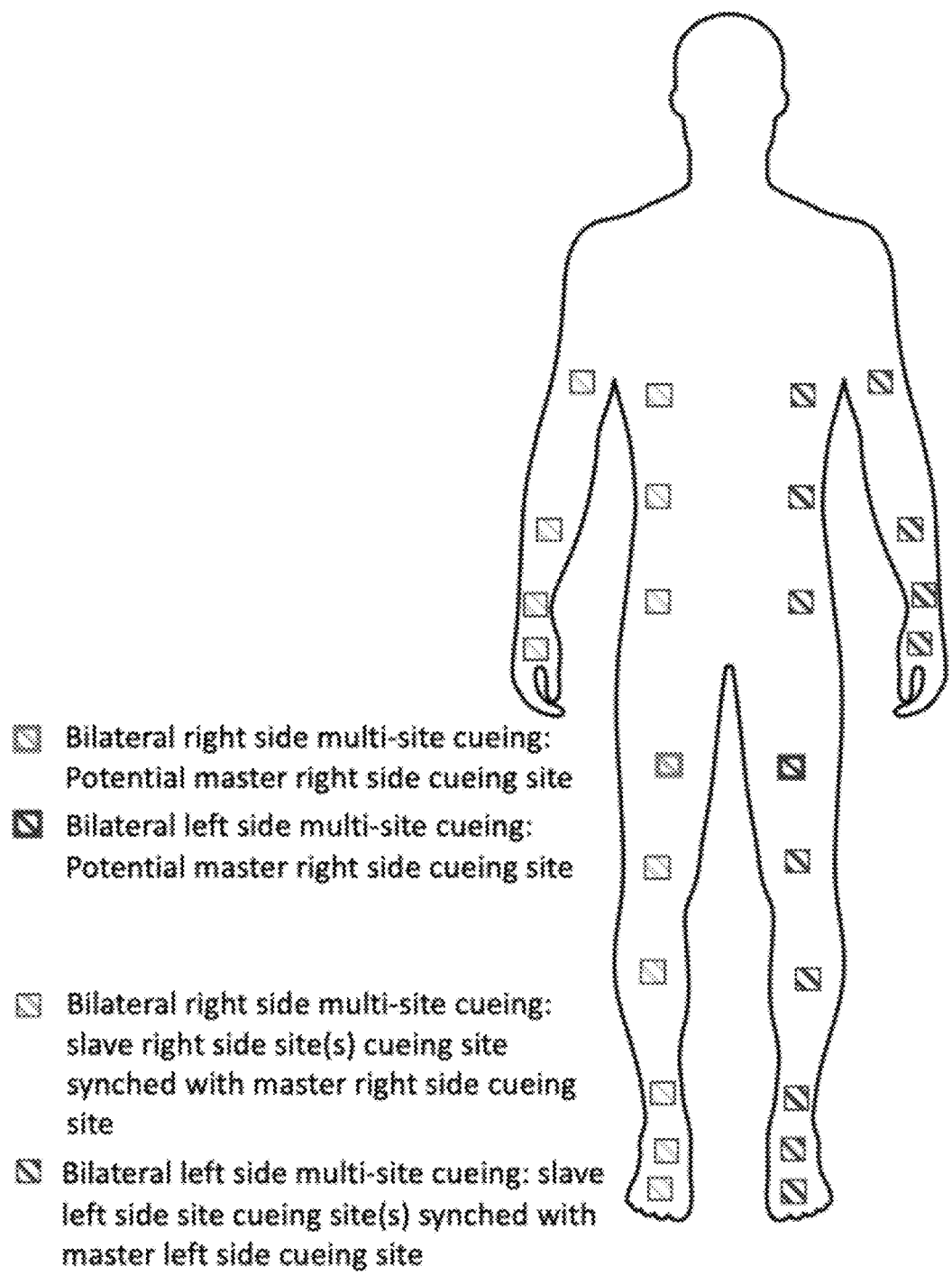

A fourth approach is shown in FIG. 27d, where multiple cueing sites are adopted for the left side and multiple cueing sites are adopted for the right side. In this case, one of the multiple sites on the left side is a master site and the other sites on the left side are slave sites that are individually synchronised in some manner with the left side master site.

Similarly, one of the multiple sites on the right side is a master site and the other sites on the right side are slave sites that are individually synchronised in some manner with the right-side master site. For example, a master site may be located on a quadriceps site, such as an upper quadriceps site, and one or more slave sites may be located on a shank site and/or a foot site of the patient. The quadriceps master site may be stimulated (for example, in response to detection of a heel-off event on that leg). The slave sites may then subsequently be stimulated, for example following a time delay (such as a pre-determined time delay, e.g., 0.01 s, 0.02 s, 0.03 s etc.) after stimulation of the master site. The slave sites may be stimulated in anatomical order, e.g., from a quadriceps site to a foot site as described above.

In addition to there being multiple ways in which to arrange the cueing sites, there are also different ways to provide cueing timing. Alternative approaches to cueing timing are explained below.

Fixed Timing Bilateral Cueing

For fixed timed bilateral cueing, stimulation is delivered alternatively to the cueing sites on the left and right sides of the patient's body. For example, stimulus to the left site(s) could be used as a cue to move the left leg to initiate/maintain walking and stimulus to the right site(s) could be used as cue to move the right leg to initiate/maintain walking.

Cueing is delivered to the left and right site(s) in an alternating, rhythmic, manner scaled to the person's previously measured un-cued step time. The cueing rhythm may be set to a time between 0-20% below the person's measured un-cued step-time for persons with festination (Table 5). For all other persons, the cueing rhythm may be set to a time between 0-20% above the person's measured un-cued step-time (Table 6).

TABLE 5

Bilateral festination timing left and right site.

Example Bilateral Timing with Festination
Un-cued Step Time = 0.5 s

| Fixed Timing Interval = 0.55 s | Step 1 | Step 2 | Step 3 | Step 4 |
|---|---|---|---|---|
| Left Stimulation Site Cue timing | 0 s | | 1.1 s | |
| Right Stimulation Site Cue timing | — | 0.55 s | — | 1.65 s |

TABLE 6

Bilateral non-festination timing left and right site.

Example Bilateral Timing without Festination
Un-cued Step Time = 0.5 s

| Fixed Timing Interval = 0.45 s | Step 1 | Step 2 | Step 3 | Step 4 |
|---|---|---|---|---|
| Left Stimulation Site Cue timing | 0 s | | 0.9 s | |
| Right Stimulation Site Cue timing | — | 0.45 s | — | 1.35 s |

Adaptive Timing Bilateral Cueing

A.

In Adaptive Timing Bilateral Cueing, the patient's previous gait cycle time is used to provide the cue timing. Adaptive Timing Bilateral Stimulation estimates the percentage of the current gait cycle which has elapsed based on the detected gait cycle time from the previous gait cycle, and provides cues based on this estimate. Thus, if the previous gait cycle time was 1.1 s and 0.1 s has elapsed in the current cycle, then the estimated percentage of the current cycle that has elapsed is (0.1/1.1)*100=9.09%.

B.

In the event, that the stride is the first stride performed and therefore a previous gait cycle time is not available, the system could use a previously stored/last stored value for cycle time for the calculation.

C.

Part 'A' above is based on the assumption, that the current cycle time will have the same value as the previous gait cycle time. This assumption will only be valid if the gait cycle time is un-changing. In the event, that the gait cycle time is changing—when the person is speeding up or slowing down their walking, then a prediction of the current cycle will have to be made. In this case, the current gait cycle time can be predicted by measuring, in real-time, a series or plurality of previous gait cycle times, using a motion sensing system, including one or more motion sensing elements, tracking these measurements in real-time, making a mathematical judgement on the trend in measured gait cycle times and then computing a predicted value for the current cycle time based on this measured trend. One way in which this could be achieved would be linear interpolation, where the trend in gait cycle times would be linearly modelled and the current value predicted from this linear model. Alternatively, a non-linear model could be used, where the measured gait cycle times are modelled using non-linear techniques and the current gait cycle time is predicted using this non-linear model. Machine learning techniques could also be used to predict the current gait cycle time.

Figure 28:
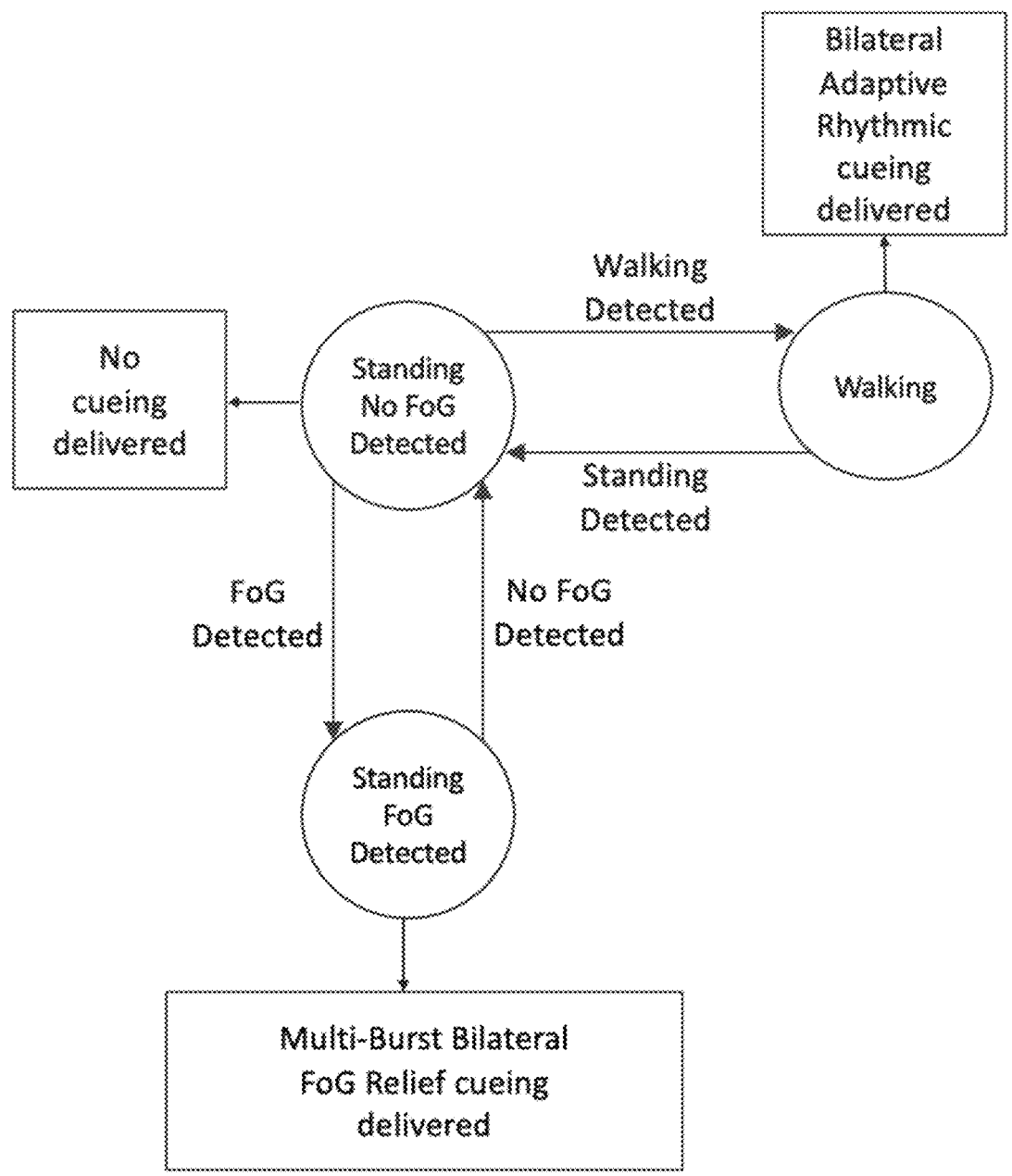
FIG. 28 shows a schematic diagram representing a bilateral cueing algorithm.

FIG. 28 shows an example of a bilateral cueing algorithm. Within the Bilateral cueing algorithm, Adaptive Timing Bilateral cueing occurs when the patient is walking. This cueing is delivered in synchronisation with the person's walking pace. In the event, that the person stops walking and adopts a standing posture, the Adaptive Timing Bilateral cueing will be superseded by a Bilateral Multi-Burst FoG Relief Stimulation where, if FoG is detected while the person is standing, bi-lateral multi-burst cueing is delivered to relieve FoG during standing, although that is not essential.

Adaptive Timing Bilateral Cueing can be performed in a number of different ways. Example embodiments are provided below.

Adaptive Timing Swing Phase Bilateral Stimulation

In one embodiment, on detection of initial contact (heel strike) of the right leg, adaptive timed stimulation is delivered to the right site(s) during the next swing phase of the right leg, based on the measured gait cycle time for the previous stride.

Similarly, in another embodiment, on detection of initial contact (heel strike) of the left leg, adaptive timed stimulation is delivered to the left site(s) during the next swing phase of the left leg, based on the measured gait cycle time for the previous stride.

Using adaptive timing cueing, if walking speed changes, the timing of the cueing will adapt to changing walking speed.

Figure 29A:
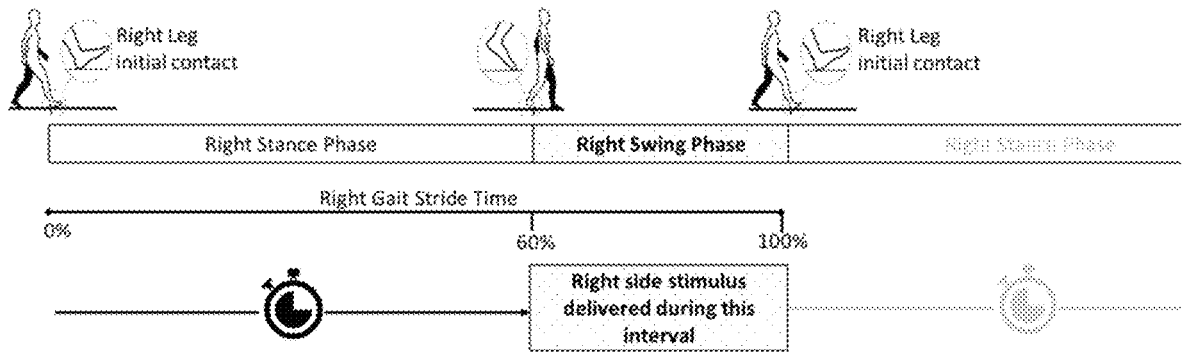
FIGS. 29A and B show a method for bilateral swing phase cueing.

For example, as shown in FIG. 29A, after detection of initial contact (heel strike) on the right leg, stimulation will be delivered to the right side cueing site(s) following the elapse of a gait cycle timer (typically 60%±tolerance of the right leg gait cycle, corresponding to the start of the right leg swing phase). The stimulus will then be delivered to the right side cueing site(s) for a specific duration of the right leg swing phase of gait, typically ranging from 0-40%±tolerance of the right leg gait cycle (stride) time.

Figure 29B:
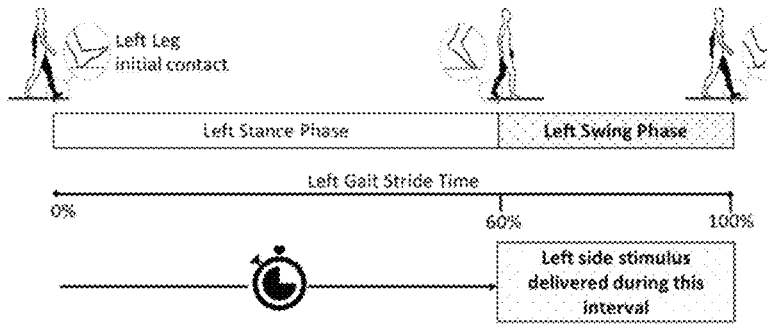

Similarly, as shown in FIG. 29B, after detection of initial contact (heel strike) on the left leg, stimulation will be delivered to the left side cueing site(s) following the elapse of a gait cycle timer (60%±tolerance of the left leg gait cycle, corresponding to the start of the left leg swing phase). The stimulus will then be delivered to the left side cueing site(s) for a specific duration of the left leg swing phase of gait, typically ranging from 0-40%±tolerance of the left leg gait cycle (stride) time.

Further, the delivery of stimulus to a leg (e.g. left leg) may be timed according to the contralateral leg (e.g. right leg).

Figure 30:
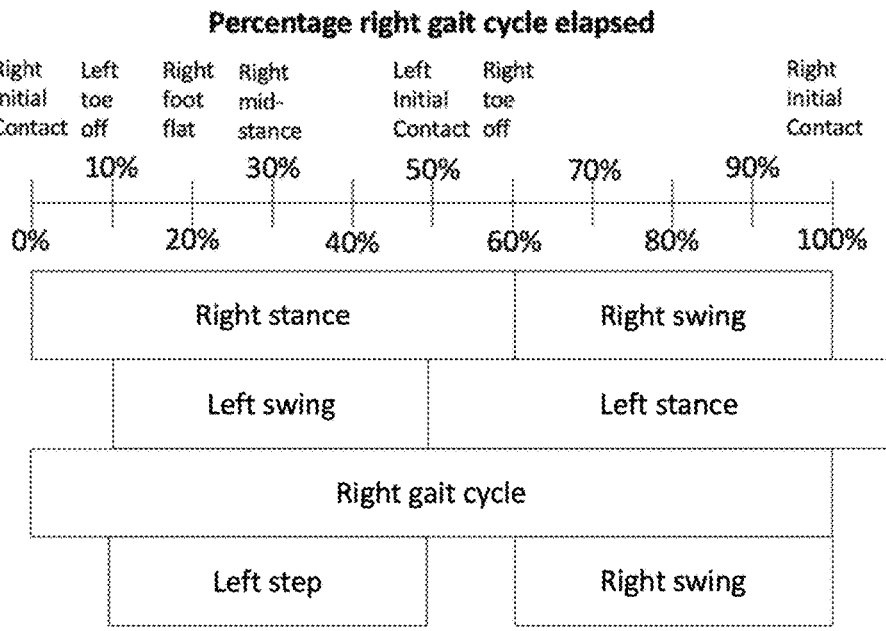
FIG. 30 shows the relationship between left and right legs during the gait cycle.

FIG. 30 shows a typical relationship between the left and right legs during walking. The right stance typically commences at 0%±tolerance of the right leg gait cycle and ends at 60%. The right leg typically swing commences at 60%±tolerance of the right leg gait cycle and ends at 100%. The left leg swing typically commences at 10%±tolerance of the right leg gait cycle and ends at 50%±tolerance of the right leg gait cycle.

Using the relationship shown in FIG. 30, stimulus to the left side can be timed from detection of heel strike on the right side in some embodiments. Similarly, stimulus to the right side can also be timed from detection of heel strike on the left side in some embodiments.

Figure 31A:
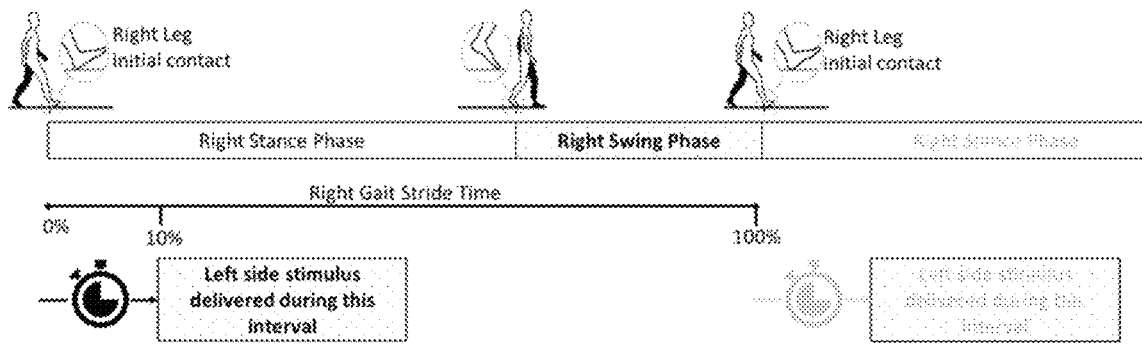
FIGS. 31A and B show a method for bilateral swing phase cueing based on initial contact of a contralateral leg.

Thus, as shown in FIG. 31A, after the detection of initial contact (heel strike) on the right leg, stimulation will be delivered to the left side cueing site(s) following the elapse of a gait cycle timer (typically 10% of the right leg gait stride time, corresponding to the start of the left leg swing phase). The stimulus will then be delivered to the left side cueing site(s) for a specific duration of the left leg swing phase of gait, typically ranging from 60-100% of the left leg gait cycle (stride) time or 10-50% of the right leg gait cycle (stride) time.

Figure 31B:
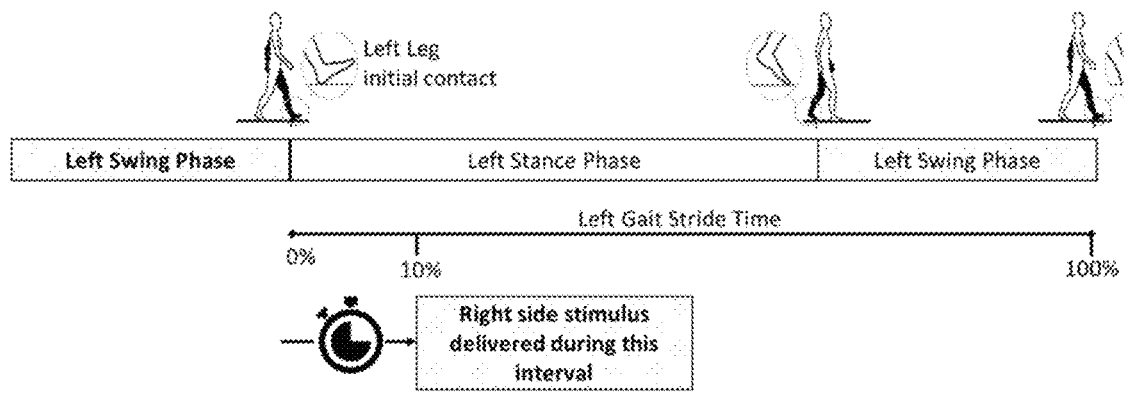

Similarly, as shown in FIG. 31B, after the detection of initial contact (heel strike) on the left leg, stimulation will be delivered to the right side cueing site(s) following the elapse of a gait cycle timer (10% of the left leg gait stride time, corresponding to the start of the right leg swing phase). The stimulus will then be delivered to the right side cueing site(s) for a specific duration of the right leg swing phase of gait, typically ranging from 60-100% of the right leg gait cycle (stride) time or 10-50% of the left leg gait cycle (stride) time.

Adaptive Timing Stance Phase Bilateral Stimulation

In some embodiments, on the detection of initial contact (heel strike) of the right leg, adaptive timed bilateral cueing stimulation is delivered to the right side cueing site(s) during the right leg gait stance phase.

Similarly, in some embodiments, on the detection of initial contact (heel strike) of the left leg, adaptive timed bilateral cueing stimulation is delivered to the left side cueing site(s) during the left leg gait stance phase.

Figure 32A:
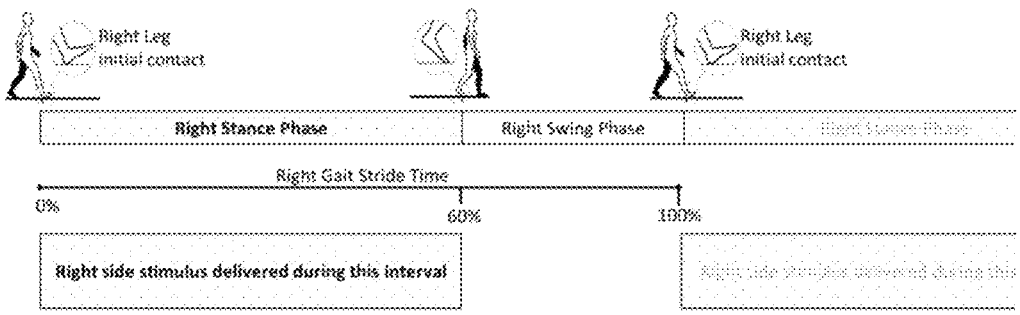
FIGS. 32A and B show a method for bilateral stance phase cueing.

For example, as shown in FIG. 32A, after the detection of initial contact (heel strike) on the right leg, stimulation will be delivered to the right side cueing site(s) for a specific duration of the right leg stance phase of gait, typically ranging from 0-60% of the right leg gait stride time).

Figure 32B:
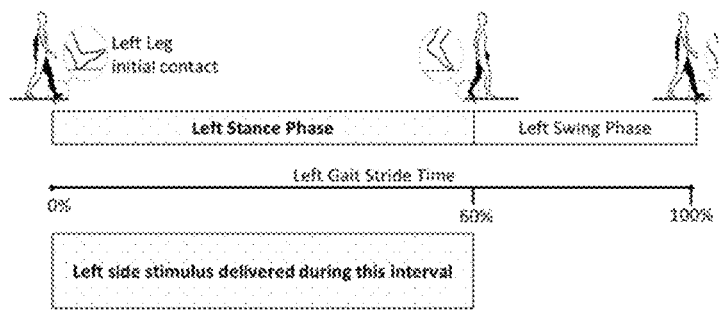

Similarly, as shown in FIG. 32B, after the detection of initial contact (heel strike) on the left leg, stimulation will be delivered to the left side cueing site(s) for a specific duration of the left leg stance phase of gait, typically ranging from 0-60% of the left leg gait stride time.

As described for swing phase stimulation, contralateral leg timing can also be used for stance phase cueing.

Adaptive Timing Swing/Stance Phase Bilateral Stimulation

In some embodiments, on the detection of initial contact (heel strike) of the right leg, adaptive timed bilateral cueing stimulation is delivered alternatively to the right site(s) over an interval during the combined stance and swing phases for the right leg. On the detection of initial contact (heel strike) of the left leg, adaptive timed bilateral cueing stimulation is delivered alternatively to the left site(s) over an interval during the combined stance and swing phases for the left leg.

Figure 33A:
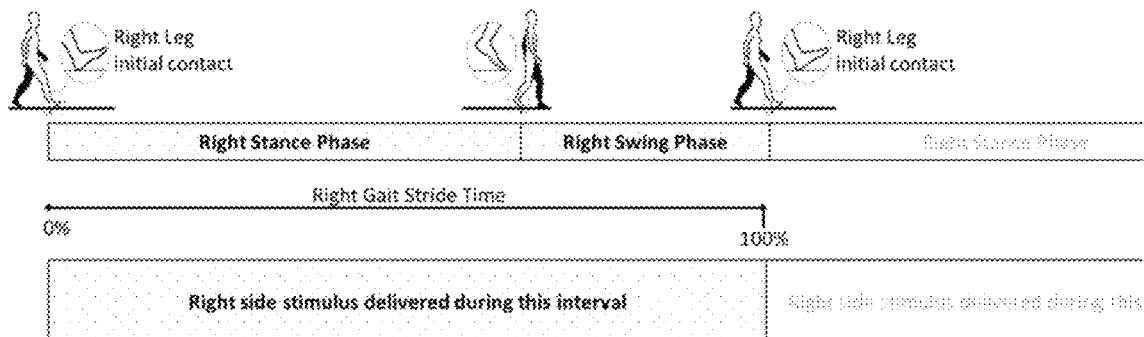
FIGS. 33A and B show a method for bilateral combined swing/stance phase cueing.

For example, as shown in FIG. 33A, after the detection of initial contact (heel strike) on the right leg, stimulation will be delivered to the right site(s) for a specific duration of the right leg gait stride time, ranging from 0-100%.

Figure 33B:
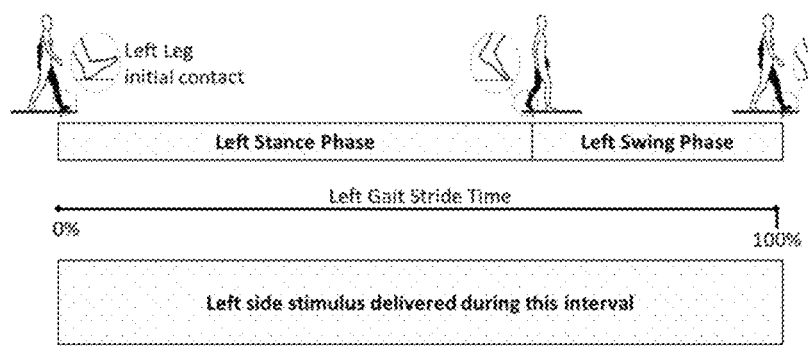

Similarly, as shown in FIG. 33B, after the detection of initial contact (heel strike) on the left leg, stimulation will be delivered to the left site(s) for a specific duration of the left leg gait stride time ranging from 0-100%.

As described for swing and stance phase stimulation, contralateral leg timing can also be used for combined swing/stance phase cueing.

Arm and Leg Movement Interaction

Figure 34:
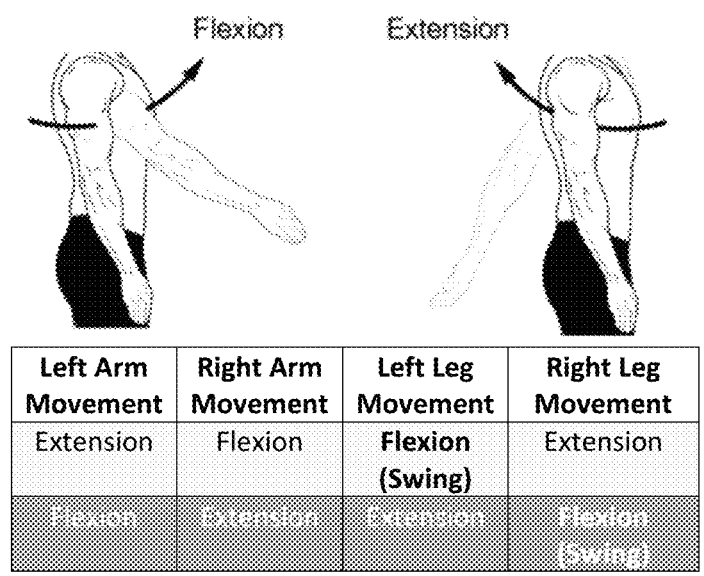
FIG. 34 shows arm extension and flexion in the sagittal plane.

In some embodiments, the timing is provided based on the phenomenon that, during walking, there is typically a contralateral relationship between arm swing and leg swing, as shown in FIG. 34. The swing phase of the right leg is associated with flexion of the left arm during walking and the swing phase of the left leg is associated with flexion of the right arm during walking.

With cueing, a number of different approaches can be adopted to take advantage of this phenomenon.

(i) Detection of arm swing (e.g., using an arm located sensor, although that is not essential) can be used to time delivery of stimulus to the contralateral leg as a cue to swing the contralateral leg in synch to the arm swing.

(ii) Detection of leg swing (occurs 60%±tolerance of leg gait cycle with 0% detected using heel-strike/initial contact of that leg) can be used to time delivery of stimulus to the contralateral arm as a cue to swing the contralateral arm in synch to leg swing.

(iii) On detection of the start of swing of a leg (occurs 60%±tolerance of leg gait cycle with 0% detected using heel-strike/initial contact of that leg), delivery of stimulus to the leg (during the swing phase of gait for that leg) and simultaneous delivery of stimulus to the contralateral arm (during flexion of the contralateral arm) as a cue to carry out flexion of the contralateral arm.

Figure 35A:
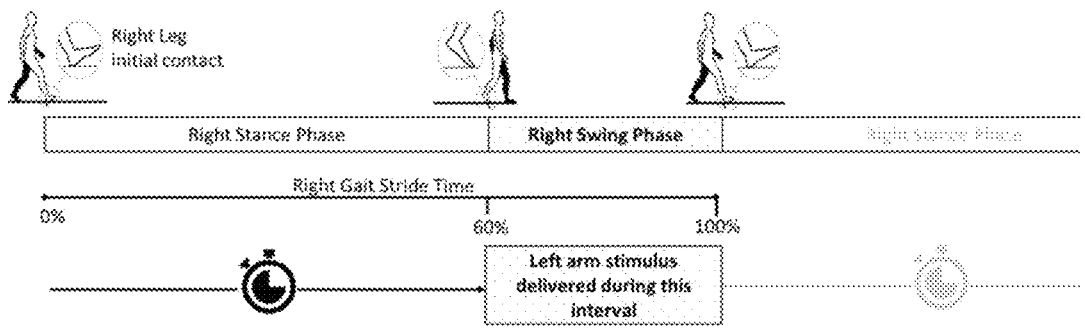
FIGS. 35A and B show a method for arm stimulation being applied in synchronisation with contralateral leg swing phase.

By way of example, as shown in FIG. 35A, after the detection of initial contact (heel strike) on the right leg, stimulation will be delivered to the left arm following the elapse of a gait cycle timer (typically 60% of the right leg gait cycle time, corresponding to the start of the right leg swing phase). The stimulus will then be delivered to the left arm for a specific duration of the right leg swing phase of gait, ranging from 60-100%±tolerance of the right leg gait cycle time.

Figure 35B:
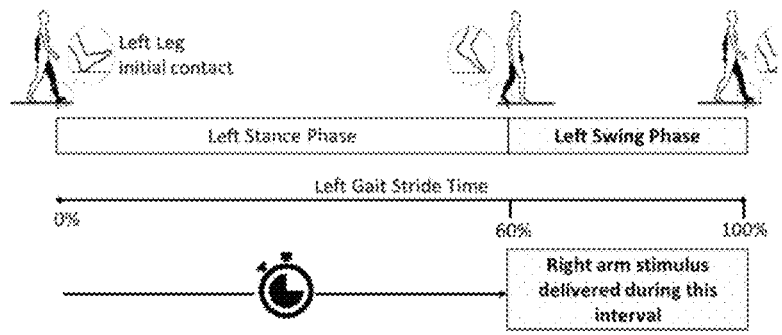

Similarly, as shown in FIG. 35B, after the detection of initial contact (heel strike) on the left leg, stimulation will be delivered to the right arm following the elapse of a gait cycle timer (60%±tolerance of the left leg gait stride time, corresponding to the start of the left leg swing phase). The stimulus will then be delivered to the right arm for a specific duration of the left leg swing phase of gait, ranging from 60-100%±tolerance of the left leg gait stride time.

Alternatively, stimulus to the right arm can also be timed from detection of sagittal plane extension event during right arm swing. The right leg heel strike event of gait will approximately correspond to the start of right arm sagittal plane extension.

Figure 36A:
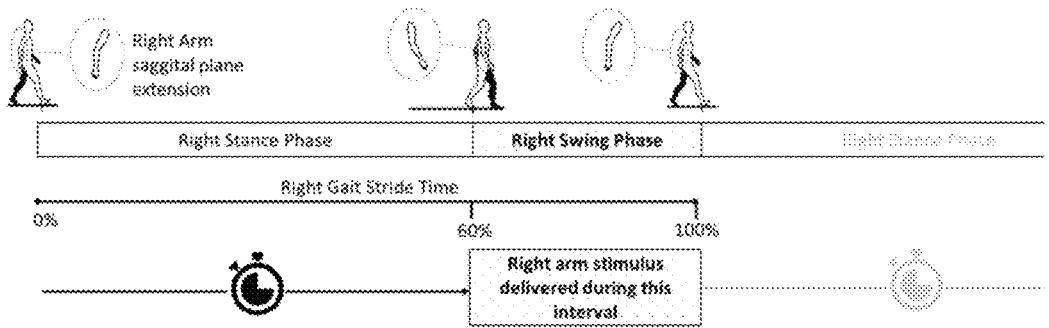
FIGS. 36A and B show a method for arm stimulation being applied in synchronisation with the arm's swing phase.

Thus, as shown in FIG. 36A, after the detection of the right arm sagittal plane extension, stimulation will be delivered to the right arm following the elapse of a gait cycle timer (typically 60% of the right leg gait stride time, corresponding to the start of the right leg swing phase). The stimulus will then be delivered to the right arm for a specific duration of the right leg swing phase of gait, ranging from 60-100%±tolerance of the right leg gait cycle time.

Figure 36B:
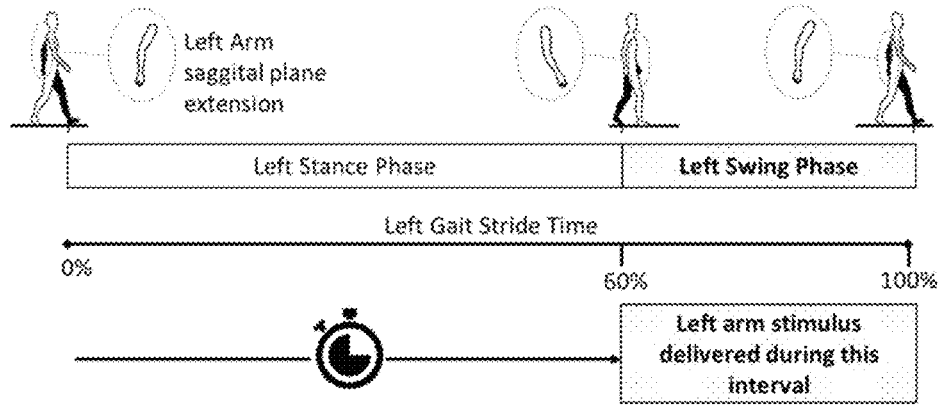

Similarly, as shown in FIG. 36B, after the detection of left arm sagittal plane extension, stimulation will be delivered to the left arm following the elapse of a gait cycle timer (60%±tolerance of the left leg gait stride time, corresponding to the start of the left leg swing phase). The stimulus will then be delivered to the left arm for a specific duration of the left leg swing phase of gait, ranging from 60-100%±tolerance of the left leg gait cycle time.

It will be appreciated the bilateral cueing approaches described above may be implemented for both FOG prevention and FOG relief, such as described above with respect to FIGS. 7 to 12.

For example, bilateral cueing may be used to prevent or mitigate FOG by applying cueing whenever the user is not seated, standing still or lying. Intention to walk or walking may be determined by the controller based on signals from the motion sensing system, and bilateral stimulation may be applied. Bilateral stimulation may be applied in a substantially continuous manner, for example in response to walking or intention to walk being detected and when the user is not standing still or sitting. Alternatively, bilateral cueing may be applied when the motion sensing system detects an alteration in gait dynamics or detection of a FOG pre-cursor. Bilateral cueing may then be delivered for a pre-defined duration, or substantially continuously until gait correction is achieved.

Alternatively, bilateral cueing may be used to relieve FOG by applying cueing when the motion sensing system detects FOG or a user manually activates cueing in responding to a FOG occurrence. Bilateral cueing may then be delivered for a pre-defined duration, or substantially continuously until FOG is relieved.

Mono-Lateral Cueing

Mono-lateral cueing is the process of providing cues to one side of a patient's body, for example to initiate and/or maintain walking. Mono-lateral cueing can be achieved by positioning cueing sites at various positions on a patient's body. For example, cueing sites may be positioned on the left or right thigh, or the left or right lower leg, or the left or right lower arm, or the left or right upper arm, or the left or right wrist.

A gait management apparatus for providing monolateral cueing may comprise at least one cueing actuator. The at least one cueing actuator includes stimulation means configured to be disposed at one or more cueing sites on one side of a patient's body to provide monolateral stimulation. The gait management apparatus may also comprise a memory for storing a non-transitory computer program, and a controller programmed to execute the program to allow the controller to activate cueing. The at least one cueing actuator, the memory and the controller are in electrical contact with one another.

As described for bilateral cueing, there are a number of different approaches for arranging cueing sites for mono-lateral cueing. Some of the possible approaches are described below with reference to FIGS. 37A-D.

Figure 37A:
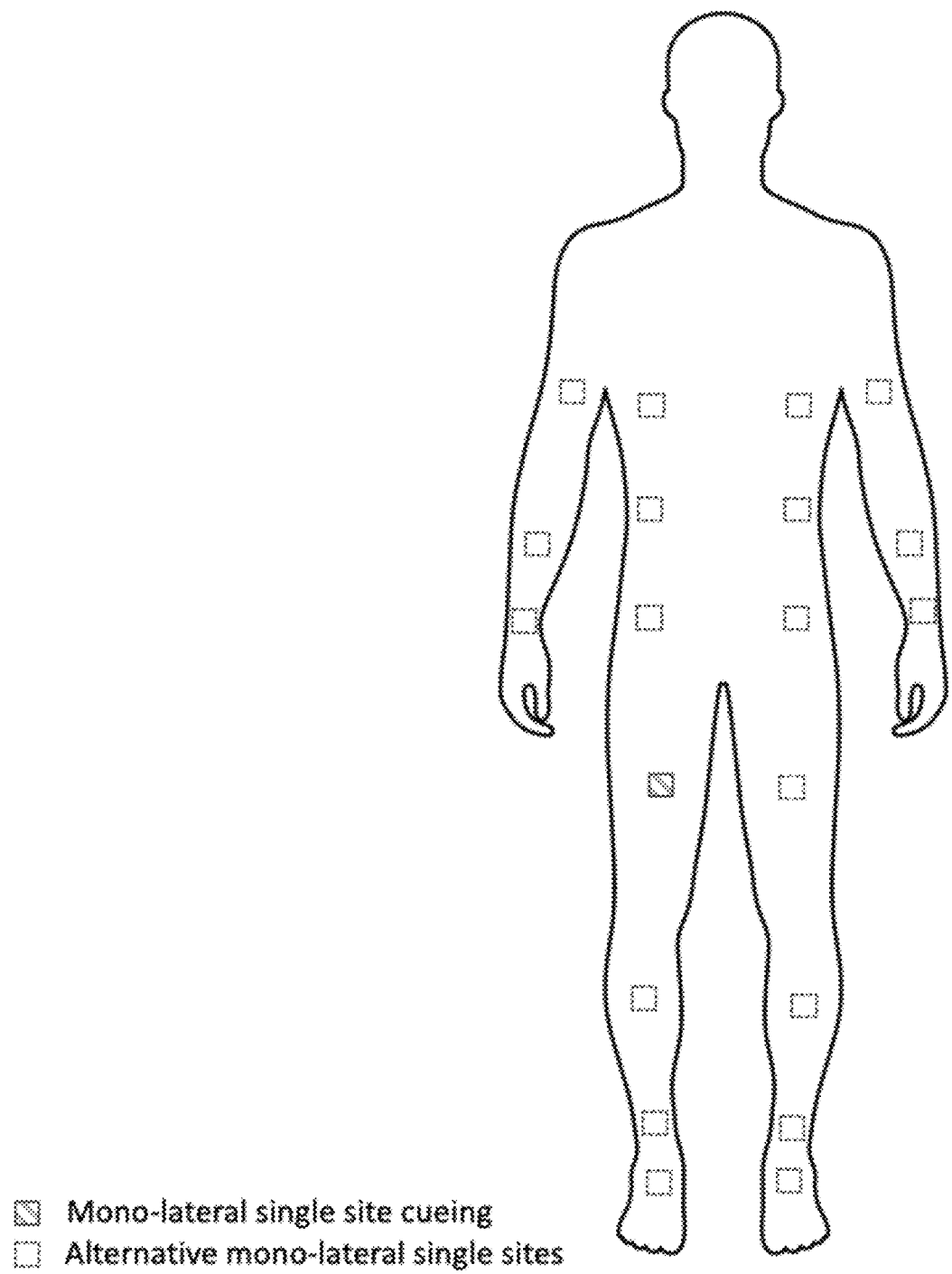
FIGS. 37A-D are diagrams illustrating possible cueing sites for mono-lateral cueing.

A first approach is shown in FIG. 37A, where a single cueing site is utilised and there are multiple possible locations for this site. The sites illustrated are by way of example.

Figure 37B:
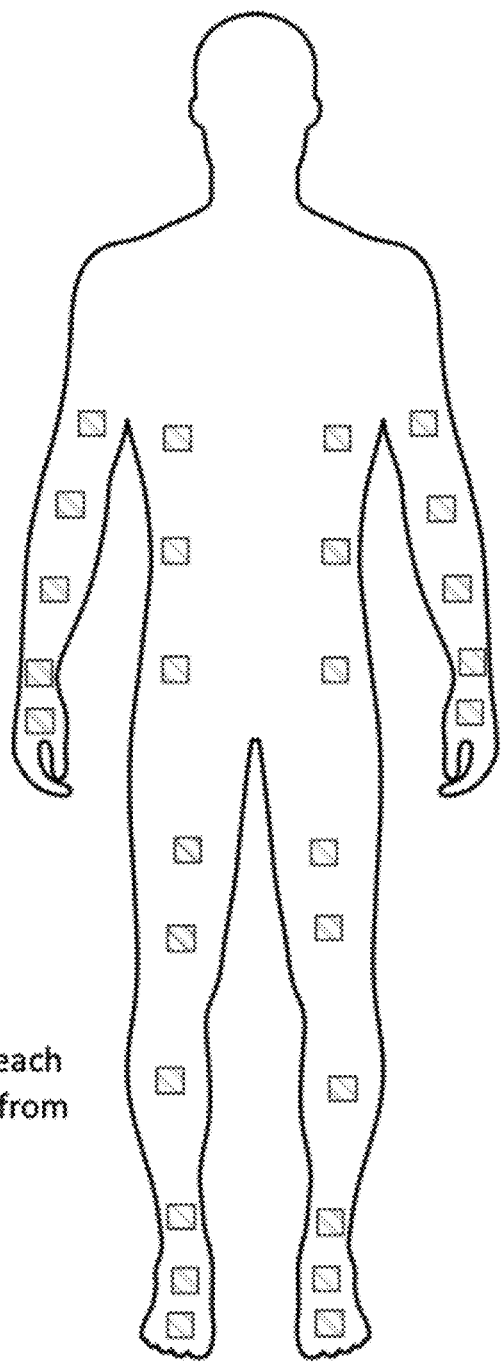

A second approach is shown in FIG. 37B, where multiple cueing sites are utilised. Each cueing site on the can be independent from the other sites. The sites can also be activated together or with a specific relationship to each other. For example, stimulation could be activated sequentially at different sites on a patient's leg. In one embodiment, cueing sites may be located on a quadriceps, a shank and a foot of the user. Stimulation may be applied sequentially starting with the quadriceps, then subsequently to the shank and finally to the foot. In another embodiment, multiple cueing sites may be located on each of a quadriceps, a shank and a foot of the patient. Stimulation may be applied at a quadriceps site near the hip, then a quadriceps site near the knee, followed by a shank site near the knee, then a shank site near the ankle, followed by a foot site near the ankle and finally a foot site near the mid-foot. More generally, the stimulation could be applied as a wave of stimulus starting at one cueing location on the patient and travelling towards another cueing location on the patient, for example from the upper thigh downwards towards the foot. Stimulation may be activated at each cueing site in anatomical order. The sites illustrated are presented by way of example, other sites would also be possible.

Figure 37C:
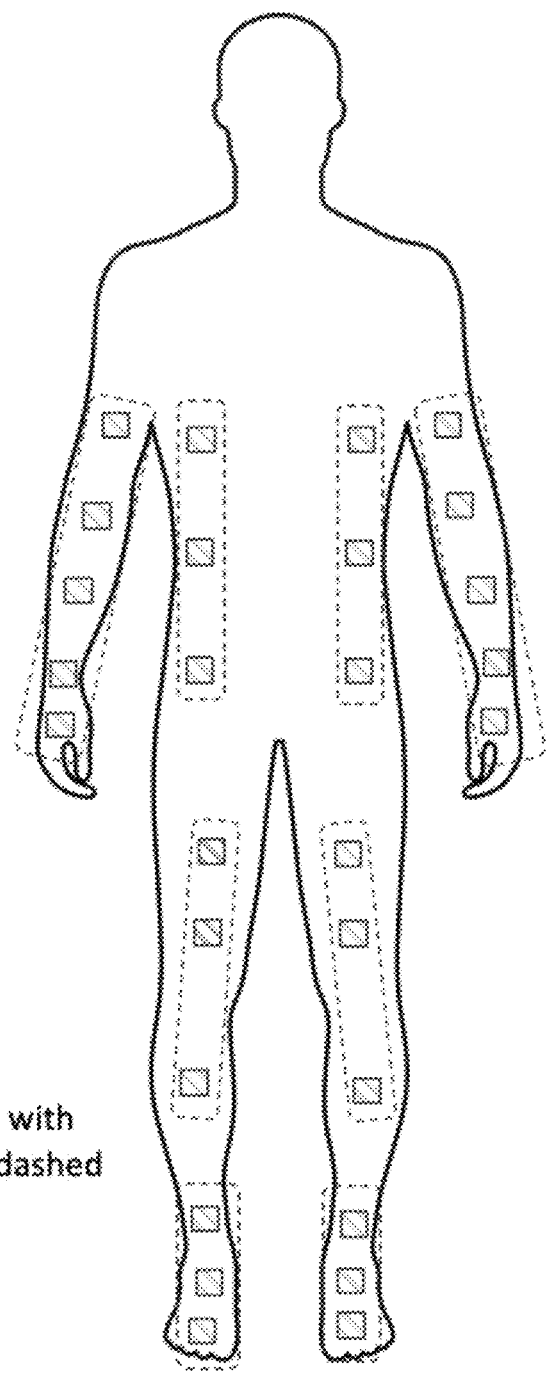

A third approach is shown in FIG. 37C where multiple cueing sites are used, but the multiple sites are composed of several groupings, where the sites in each grouping work in unison. Sites in one grouping can be independent from the other sites in other groupings. Alternatively, there can be a defined relationship between the activity in one grouping and the activity in another grouping. For example, stimulation could be activated sequentially at different groups of sites on a patient's leg. In one embodiment, groups of cueing sites may be located on a quadriceps, a shank and a foot of the user. Stimulation may be applied sequentially starting with the quadriceps group of sites, then subsequently to the shank group of sites and finally to the foot group of sites. More generally, the stimulation could be applied as a wave of stimulus starting at one group of cueing locations on the patient and travelling towards another group of cueing locations on the patient, for example from the upper thigh downwards towards the foot. Stimulation may be activated at each group of cueing sites in anatomical order. The groupings illustrated are presented by way of example, other groupings would also be possible.

Figure 37D:
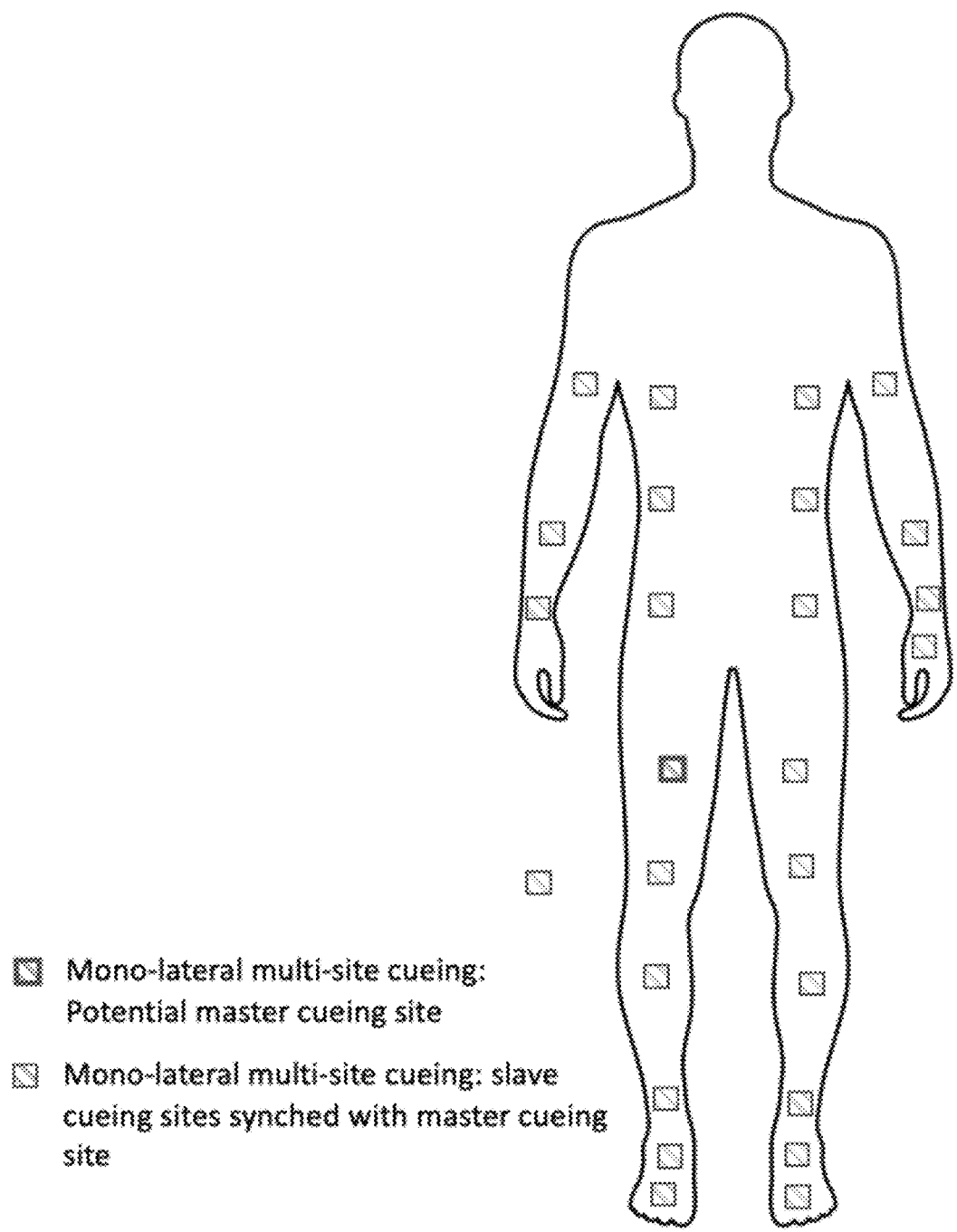

Finally, a fourth approach is shown in FIG. 37D, where multiple cueing sites are used. In this case one of the multiple sites is a master site and the other sites are slave sites that are individually synchronised in some manner with the master site. For example, a master site may be located on a quadriceps site, such as an upper quadriceps site, and one or more slave sites may be located on a shank site and/or a foot site of the patient. The quadriceps master site may be stimulated (for example, in response to detection of a heel-off event on that leg). The slave sites may then subsequently be stimulated, for example following a time delay (such as a pre-determined time delay, e.g., 0.01 s, 0.02 s, 0.03 s etc.) after stimulation of the master site. The slave sites may be stimulated in anatomical order, e.g., from a quadriceps site to a foot site as described above.

Fixed Timing Mono-lateral Cueing

Mono-lateral cueing can be delivered using either step-time cueing or stride time cueing, as shown in Tables 7 and. With step-time cueing, a cue is delivered to correspond to each step to be taken. With stride-time cueing, a cue is delivered to correspond to each stride to be taken.

With fixed timing mono-lateral Cueing, cueing is delivered to a site at the thigh/trunk/arm/lower leg/foot/wrist/hand/ankle in a rhythmic, manner scaled to the participant's measured un-cued step time. The cueing rhythm may be set to 0-20%±tolerance below the participant's measured un-cued step-time for participants with festination (Table 7).

For all other participants, the cueing rhythm may be set to 0-20%±tolerance above the participant's measured un-cued step-rate (Table 8).

TABLE 7

Bilateral festination timing left and right site.

Example Timing with Festination
Step Time = 0.5 s Stride Time = 1 s
Fixed Timing Interval = 0.55 s

| | Step 1 | Step 2 | Step 3 | Step 4 |
|---|---|---|---|---|
| Stimulation Site using Step Time cueing | 0 s | 0.55 s | 1.1 s | 1.65 s |
| Stimulation Site using Stride Time cueing | 0 s | — | 1.1 s | — |

TABLE 8

Bilateral non-festination timing left and right site.

Example Timing without Festination
Step Time = 0.5 s Stride Time = 1 s
Fixed Timing Interval = 0.45 s

| | Step 1 | Step 2 | Step 3 | Step 4 |
|---|---|---|---|---|
| Stimulation Site using Step Time cueing | 0 s | 0.45 s | 0.9 s | 1.35 s |
| Stimulation Site using Stride Time cueing | 0 s | — | 0.9 s | — |

Adaptive Timing Mono-Lateral Cueing

A.

In Adaptive Timing Mono-lateral Cueing, the patient's previous gait cycle time is used to provide the cue timing. Adaptive Timing Mono-lateral Stimulation estimates the percentage of the current gait cycle which has elapsed based on the detected gait cycle time from the previous gait cycle. If previous gait cycle time was 1.1 s, and 0.1 s has elapsed in the current cycle, then the estimated percentage of the current cycle that has elapsed is (0.1/1.1)*100=9.09%.

B.

In the event, that the stride is the first stride performed and therefore a previous gait cycle time is not available, the system could use a previously stored/last stored value for cycle time for the calculation.

C.

Part 'A' is based on the assumption, that the current cycle time will have the same value as the previous gait cycle time. This assumption will only be valid if the gait cycle time is un-changing. In the event, that the gait cycle time is changing—when the person is speeding up or slowing down their walking, then a prediction of the current cycle will have to be made. In this case, the current gait cycle time can be predicted by measuring, in real-time, a series or plurality of previous gait cycle times, using a motion sensing system, including one or more motion sensing elements, tracking these measurements in real-time, making a mathematical judgement on the trend in measured gait cycle times and then computing a predicted value for the current cycle time based on this measured trend. One way in which this could be achieved would be linear interpolation, where the trend in gait cycle times would be linearly modelled and the current value predicted from this linear model. Alternatively, a non-linear model could be used, where the measured gait cycle times are modelled using non-linear techniques and the current gait cycle time is predicted using this non-linear model. Machine learning techniques could also be used to predict the current gait cycle time.

Figure 38:
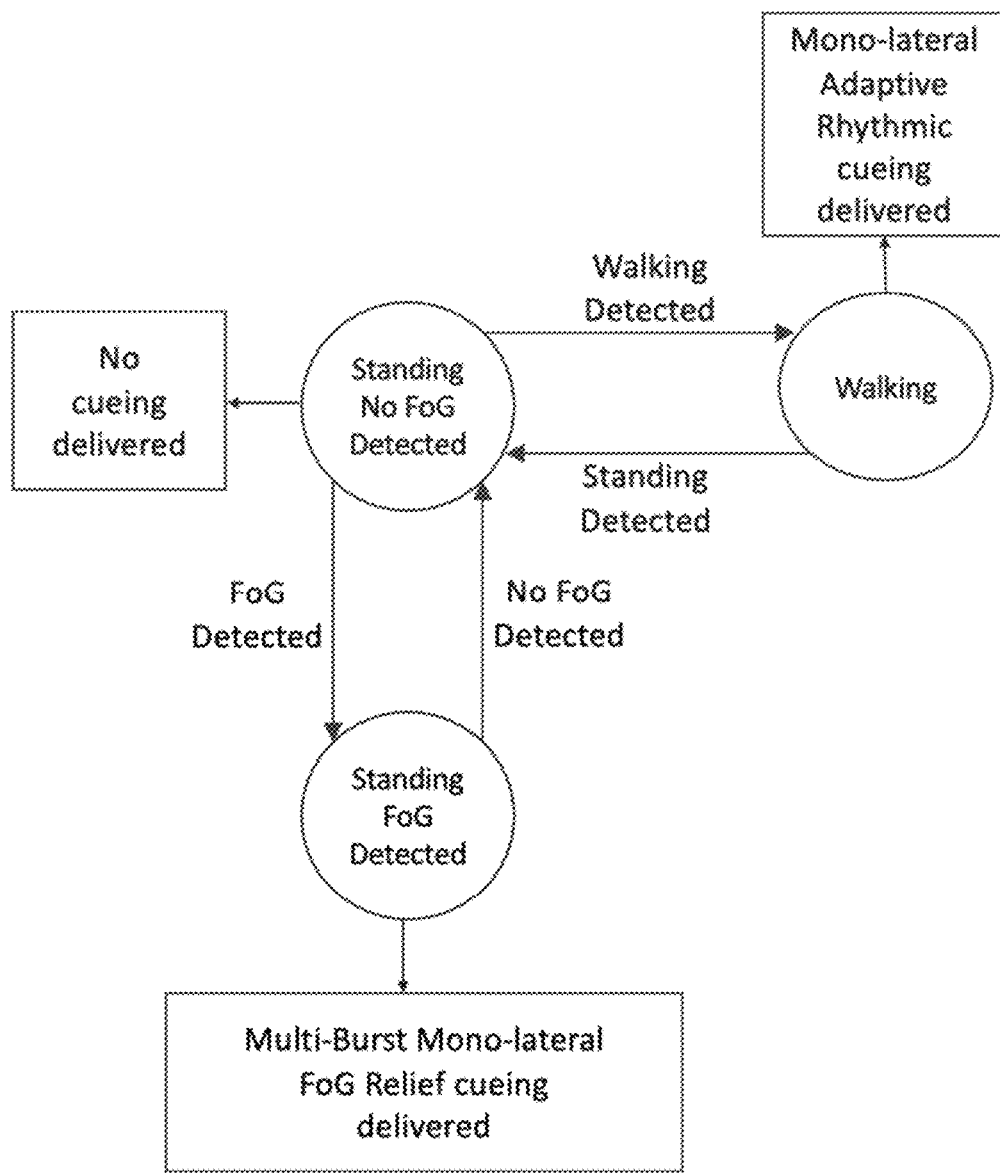
FIG. 38 shows a schematic diagram representing a bilateral cueing algorithm.

An example of a mono-lateral cueing algorithm is shown in FIG. 38. Within the Mono-lateral cueing algorithm, Mono-lateral Adaptive Timing cueing occurs when the person is walking and in this cueing is delivered in synch to the person's walking pace. In the event, that the person stops walking and adopts a standing posture, the Mono-lateral Adaptive Timing Stimulation will be super-ceded by a Mono-lateral Multi-Burst FoG Relief Stimulation, where if FoG is detected while the person is standing, bi-lateral multi-burst cueing is delivered to relieve FoG during standing, although that is not essential.

Adaptive Timing Mono-lateral Cueing can be performed in a number of different ways. Example embodiments are provided below.

Adaptive Timing Swing Phase Mono-Lateral Stimulation

In some embodiments, on the detection of right initial contact (heel strike), adaptive timed mono-lateral cueing stimulation is delivered to the right side cueing site(s), during right leg swing phase of gait and this is repeated every stride for stride time cueing.

Alternatively, in some embodiments, on the detection of right initial contact (heel strike), adaptive timed mono-lateral cueing stimulation is delivered to the right side cueing site(s), during right leg swing phase of gait and then is delivered to the right side cueing site(s), during left leg swing phase of gait and is repeated every stride for step time cueing.

Similarly, in some embodiments, on the detection of left initial contact (heel strike), adaptive timed mono-lateral cueing stimulation is delivered to the left side cueing site(s), during left leg swing phase of gait and this is repeated every stride for stride time cueing. This is referred to as stride time cueing as a cue is delivered every stride.

Alternatively, in some embodiments, on the detection of left initial contact (heel strike), adaptive timed mono-lateral cueing stimulation is delivered to the left side cueing site(s), during left leg swing phase of gait and then is delivered to the left side cueing site(s), during right leg swing phase of gait and is repeated every stride for step time cueing. This is referred to as step time cueing as a cue is delivered every step.

Figure 39A:
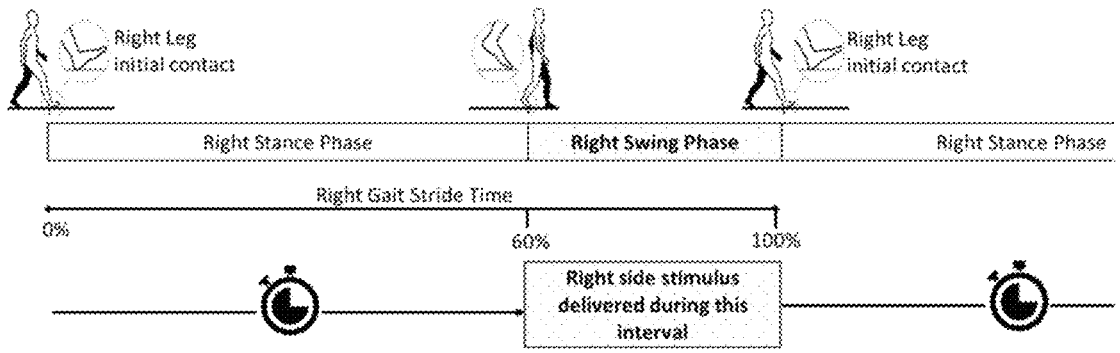
FIGS. 39A and B show a method for mono-lateral swing phase stride time cueing.

For example, as shown in FIG. 39A, after the detection of initial contact (heel strike) on the right leg, stimulation will be delivered to the right site(s) following the elapse of a gait cycle timer (60%±tolerance of the right leg gait cycle time, corresponding to the start of the right leg swing phase). The stimulus will then be delivered for a specific duration of the right leg swing phase of gait, ranging from 60-100%±tolerance of the right leg gait cycle (stride) time. This is referred to as stride time cueing as a cue is delivered every stride.

Figure 39B:
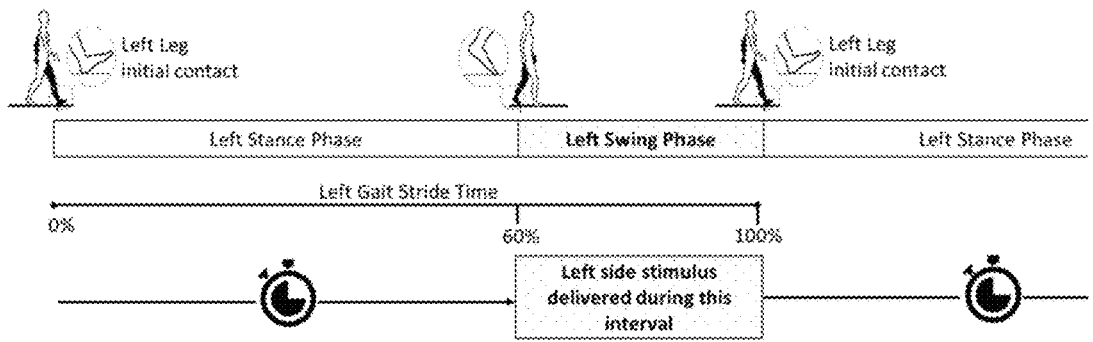

Similarly, as shown in FIG. 39B, after the detection of initial contact (heel strike) on the left leg, stimulation will be delivered to the left site(s) following the elapse of a gait cycle timer (60%±tolerance of the left leg gait stride time, corresponding to the start of the left leg swing phase). The stimulus will then be delivered for a specific duration of the left leg swing phase of gait, ranging from 60-100%±tolerance of the left leg gait cycle time. This is referred to as stride time cueing as a cue is delivered every stride.

Figure 40A:
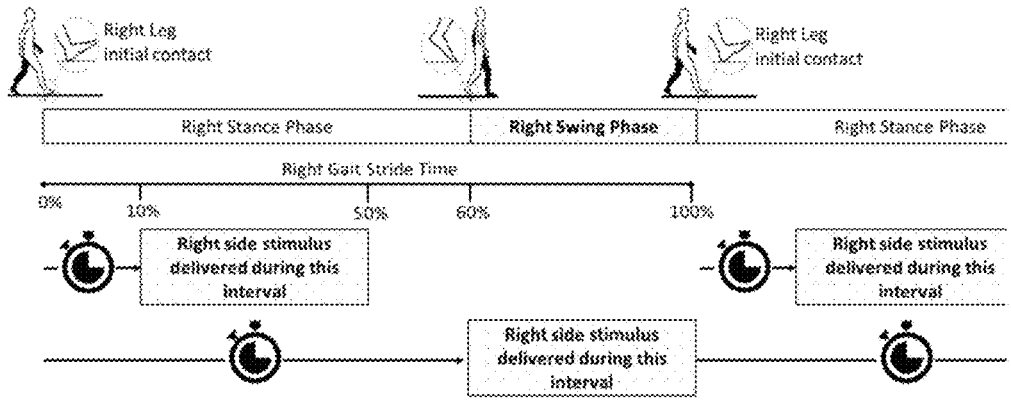
FIGS. 40A and B show a method for mono-lateral swing phase step time cueing.

Alternatively, as shown in FIG. 40A, after the detection of initial contact (heel strike) on the right leg, stimulation will be delivered to the right side cueing site(s) following the elapse of a gait cycle timer (10% of the right leg gait stride time, corresponding to the start of the left leg swing phase). The stimulus will then be delivered for a specific duration of the left leg swing phase of gait, ranging from 10-50% of the right leg gait stride time. Then, stimulation will be delivered to the right side cueing site(s) following the elapse of a gait cycle timer (60% of the right leg gait stride time, corresponding to the start of the right leg swing phase). The stimulus will then be delivered for a specific duration of the left leg swing phase of gait, ranging from 60-100% of the right leg gait stride time. This is referred to as step time cueing as a cue is delivered every step.

Figure 40B:
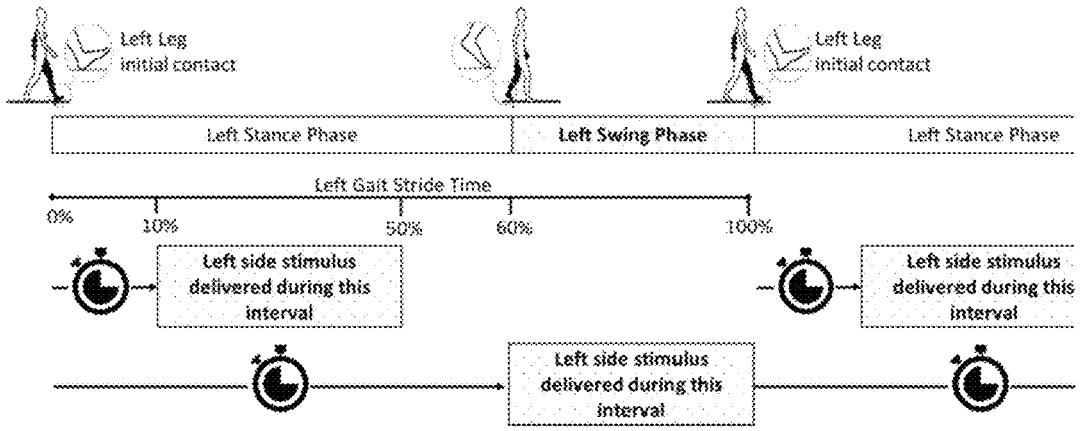

Similarly, as shown in FIG. 40B, after the detection of initial contact (heel strike) on the left leg, stimulation will be delivered to the left side cueing site(s) following the elapse of a gait cycle timer (10% of the left leg gait stride time, corresponding to the start of the right leg swing phase). The stimulus will then be delivered for a specific duration of the right leg swing phase of gait, ranging from 10-50% of the left leg gait stride time. Then, stimulation will be delivered to the left side cueing site(s) following the elapse of a gait cycle timer (60% of the left leg gait stride time, corresponding to the start of the left leg swing phase). The stimulus will then be delivered for a specific duration of the left leg swing phase of gait, ranging from 60-100% of the left leg gait stride time. This is referred to as step time cueing as a cue is delivered every step.

Adaptive Timing Stance Phase Mono-Lateral Stimulation

In some embodiments, on the detection of initial contact (heel strike), adaptive timed mono-lateral cueing stimulation is delivered to either the left or right side cueing site(s) (corresponding to leg performing the detected heel strike) during either the left or right leg gait stance phase (Stride Time cueing).

Figure 41A:
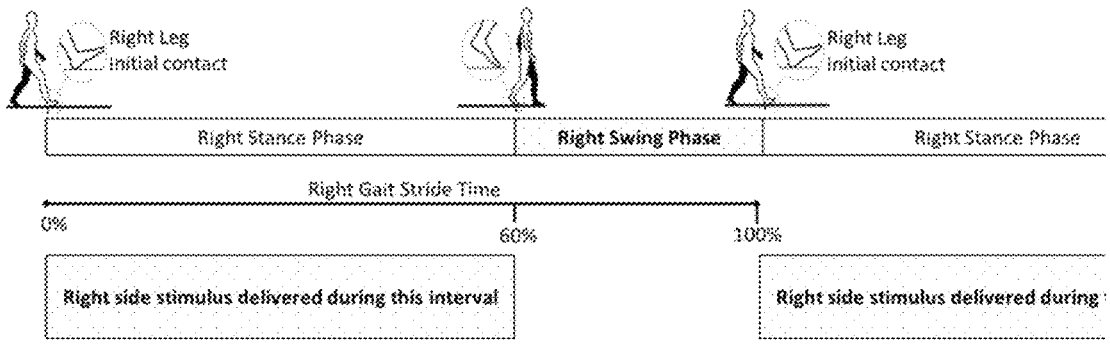
FIGS. 41A and B show a method for mono-lateral stance phase stride time cueing.

For example, as shown in FIG. 41A, after the detection of initial contact (heel strike) on the right leg, stimulation will be delivered to the right side cueing site(s) for a specific duration of the right leg stance phase of gait, ranging from 0-60%±tolerance of the right leg gait stride time.

Figure 41B:
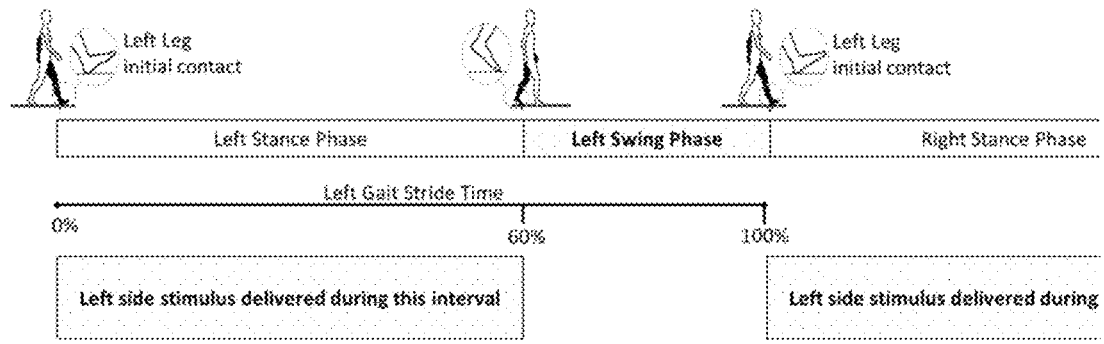

Similarly, as shown in FIG. 41B, after the detection of initial contact (heel strike) on the left leg, stimulation will be delivered to the left side cueing site(s) for a specific duration of the left leg stance phase of gait, ranging from 0-60%±tolerance of the left leg gait stride time.

Adaptive Timing Swing/Stance Phase Mono-Lateral Stimulation

In some embodiments, on the detection of initial contact (heel strike), adaptive timed mono-lateral cueing stimulation is delivered to either the left or right side cueing site(s) (corresponding to leg performing the detected heel strike).

Figure 42A:
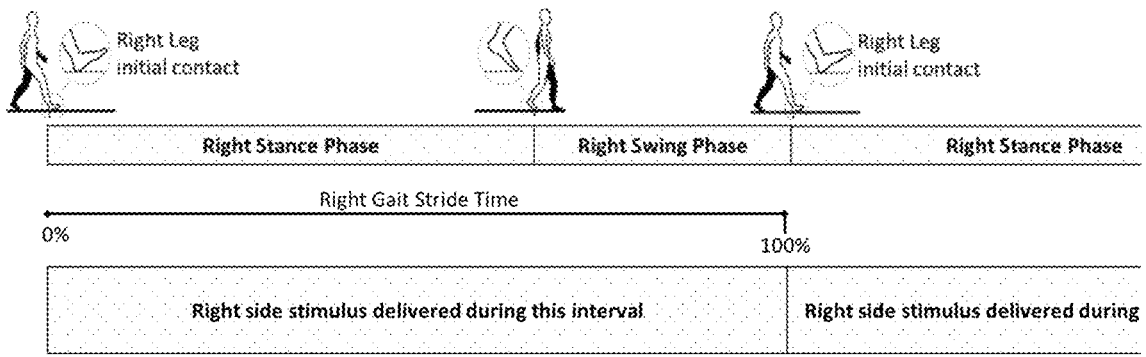
FIGS. 42A and B show a method for mono-lateral combined swing/stance phase cueing.

For example, as shown in FIG. 42A, after the detection of initial contact (heel strike) on the right leg, stimulation will be delivered to the right side cueing site(s) for a specific duration of the right leg gait cycle (combined stance and swing phase), ranging from 0-100% of the right leg gait cycle.

Figure 42B:
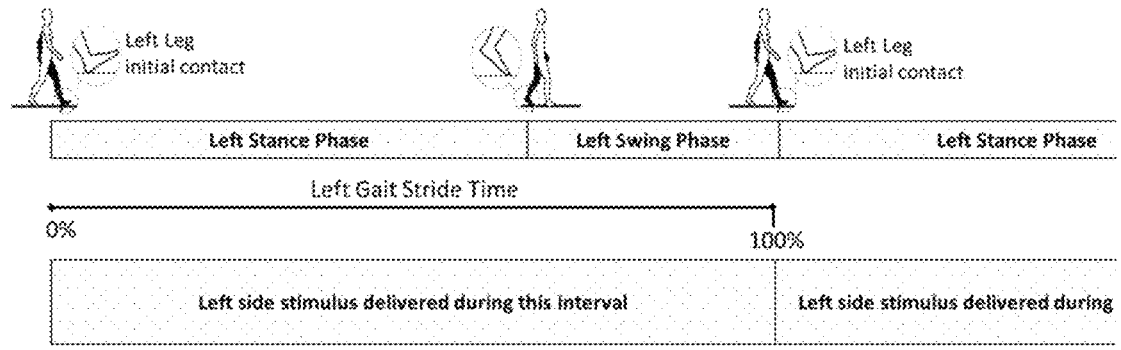

Similarly, as shown in FIG. 42B, after the detection of initial contact (heel strike) on the left leg, stimulation will be delivered to the left site(s) for a specific duration of the left leg gait cycle (combined stance and swing phase), ranging from 0-100% of the left leg gait cycle.

It will be appreciated the mono-lateral cueing approaches described above may be implemented for both FOG prevention and FOG relief, such as described above with respect to FIGS. 7 to 12.

For example, mono-lateral cueing may be used to prevent or mitigate FOG by applying cueing whenever the user is not seated, standing still or lying. Intention to walk or walking may be determined by the controller based on signals from the motion sensing system, and bilateral stimulation may be applied. Mono-lateral stimulation may be applied in a substantially continuous manner, for example in response to walking or intention to walk being detected and when the user is not standing still or sitting. Alternatively, mono-lateral cueing may be applied when the motion sensing system detects an alteration in gait dynamics or detection of a FOG pre-cursor. Mono-lateral cueing may then be delivered for a pre-defined duration, or substantially continuously until gait correction is achieved.

Alternatively, mono-lateral cueing may be used to relieve FOG by applying cueing when the motion sensing system detects FOG or a user manually activates cueing in responding to a FOG occurrence. Mono-lateral cueing may then be delivered for a pre-defined duration, or substantially continuously until FOG is relieved.

Both bilateral and mono-lateral cueing may also be applied in accordance with one or more of the following approaches.

1. Cueing may be delivered as a rhythmic, repetitive series of cues (bursts of stimulus) whose delivery is synchronised (for example, using fixed timing or adaptive timing as described above) to a walking cadence of the patient. The cueing is delivered each stride on a continuous basis, for example while the patient is walking or intending to walk. This form of cueing may be used to prevent or mitigate gait dysfunction such as FOG.

2. Cueing may be delivered as a rhythmic, repetitive series of cues (bursts of stimulus) whose delivery is synchronised (for example, using fixed timing or adaptive timing as described above) to a walking cadence of the patient. The cueing is delivered to predetermined or random different strides on a continuous basis, for example while the patient is walking or intending to walk. This form of cueing may be used to prevent or mitigate gait dysfunction such as FOG.

3. Cueing may be delivered in response to a detected activity or gait event of the patient (for example, a point or event in the gait cycle of the patient as described above, or a gait dysfunction) as a rhythmic, repetitive series of cues (bursts of stimulus) whose delivery is synchronised (for example, using fixed timing or adaptive timing as described above) to a walking cadence of the patient. The cueing is delivered for a predetermined duration of time. This form of cueing may be used to relieve gait dysfunction such as FOG.

Figure 7:
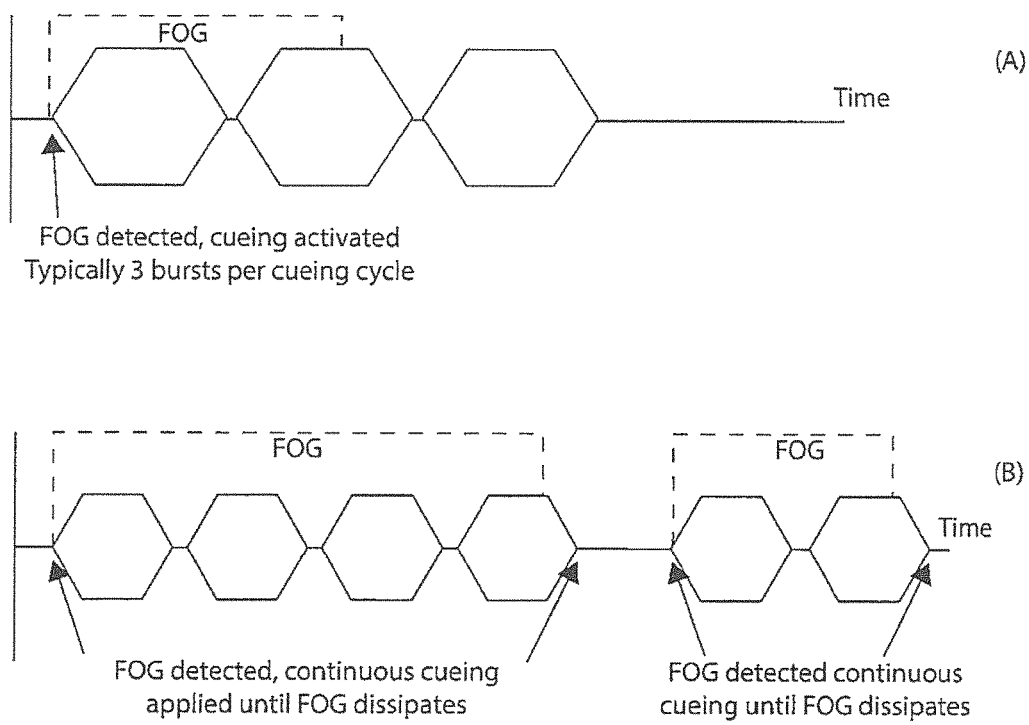
FIG. 7 is a pair of plots, (A) burst cueing activation in response to FOG detection, in which a typical burst consists of 3 stimulus bursts, (B) continuous stimulation applied while a FOG episode is present.

4. Cueing may be delivered as one or more bursts of stimulation in response to a detected activity or gait event of the patient (for example, a point or event in the gait cycle of the patient as described above, or a gait dysfunction). A burst is a unit of cueing stimulus with a Ramp-Up Time, an ON Time, a Ramp-Down Time and an OFF Time (FIG. 6). These timing parameters characterise the stimulation envelope, that specifies how the intensity of the stimulus varies with time and the different timing parameters of the stimulation intensity envelope can be varied to change the cue characteristics. One or multiple sequential bursts of stimulus can be delivered on detection of a gait dysfunction such as FOG (FIG. 7). The number of bursts of stimulus delivered can be varied based on the characteristics of the patient. This form of cueing may be used to relieve gait dysfunctions such as FOG. Multiple bursts of stimulus, delivered in a regular, rhythmic manner, are used to deliver rhythmic, repetitive series of cues whose delivery is synchronised (for example, using fixed timing or adaptive timing as described above) to a walking cadence of the patient.

5. Cueing may be delivered as one or more bursts of stimulation at regular or irregular intervals of time. A burst is a unit of stimulus, as described above. This form of cueing may be used to prevent or mitigate gait dysfunction such as FOG.

6. Cueing may be delivered at some times during walking as a rhythmic, repetitive series of cues (bursts of stimulus) whose delivery is synchronised (for example, using fixed timing or adaptive timing as described above) to a walking cadence of the patient. The cueing is delivered to predetermined or random different strides on a continuous basis, for example while the patient is walking. Additionally, cueing may be delivered at other times (e.g., intermittently between the rhythmic, repetitive cues) as one or more bursts of stimulus at regular or irregular intervals of time. This form of cueing may be used to prevent or mitigate gait dysfunction such as FOG.

Figure 43:
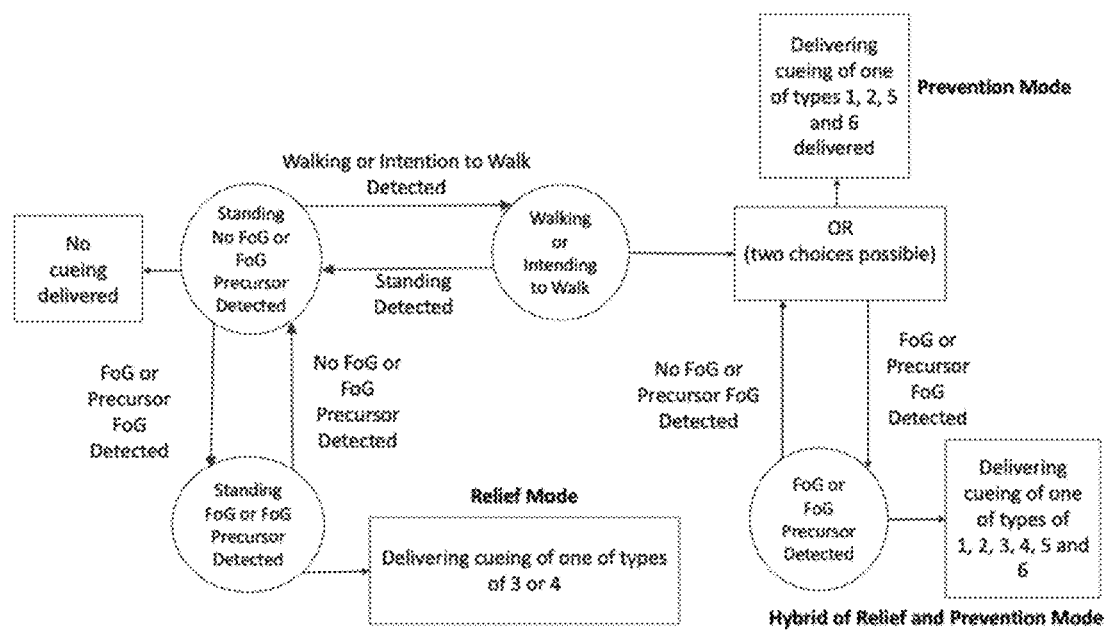
FIG. 43 shows a state transition diagram for applying monolateral or bilateral cueing.

FIG. 43 shows a state transition diagram illustrating activation of the gait management apparatus and the type of cueing the gait management apparatus may deliver.

Habituation Prevention/Relief Mechanisms

Habituation is where the user of the cueing device habituates or becomes used to the sensation caused by the stimulation delivered by the cueing device, and the effectiveness of the cueing in its original form is reduced.

Habituation may be prevented, mitigated or addressed by changing one or more stimulation parameters of the stimulation delivered by the cueing device, and hence changing the sensation experienced by the user. Stimulation parameters that can be changed may include a type of stimulation such as electrical stimulation, haptic or mechanical stimulation, and mixed stimulation combining electrical and haptic stimulation.

Stimulation parameters that may be changed may also include a location of the stimulation, such as a cueing site at which stimulation is delivered.

Stimulation parameters that may changed may also include a morphology of the stimulation, such as one or more of an amplitude or intensity, pulse frequency, pulse width, inter-pulse interval, ramp-up time, ramp-down time, on-time and off-time.

Stimulation parameters that may be changed may also include a mode of stimulation. Modes of stimulation may include a prevention mode and a relief mode. A prevention mode may be configured to prevent or mitigate a gait dysfunction, for example as described above. In prevention mode, stimulation may be delivered in a substantially continuous manner, for example a cyclic continuous manner. A relief mode may be configured to relieve a detected gait dysfunction, for example as described above. In relief mode, stimulation may be delivered as one or more bursts of stimulus when a gait dysfunction (such as a FOG episode) is detected. The gait dysfunction may be detected automatically, for example by the controller in cooperation with a motion sensing system. Alternatively, a patient or other person may manually activate relief mode cueing on experiencing or detecting a gait dysfunction.

The change of one or more stimulation parameters to prevent or mitigate habituation may occur in one or more of the following ways. The stimulation parameters may be automatically changed, either continuously or intermittently. For example, the stimulation parameters may be automatically changed after each of a succession of time periods of a pre-determined length (for example, hourly, daily, weekly, monthly).

Alternatively, the stimulation parameters may be automatically changed in response to detection of habituation (e.g., with no user or clinician input). That may address the onset of habituation and mitigate further progression of habituation. For example, using the controller and a motion sensing system as described above, different aspects of the patient's gait and activity may be determined and analysed to assess habituation.

For example, the following aspects of the patient's gait and activity may be assessed: a percentage of time in FOG per second of walking; a number of FOG episodes occurring per second of walking; an average walking speed; an average stride time; an average step time; an average stride length; and average step length; a number and intensity of heel strikes per second of walking; a step rate; a stride rate; a percentage of time in stance phase; and a percentage of time in swing phase.

Another approach for mitigating habituation may comprise changing the stimulation parameters on receiving a manual input or prompt, for example from a button or user interface operatively or communicatively coupled to the controller and manually operated by the patient or a clinician.

A number of approaches may be used to determine how and in what an order the stimulation parameters may be changed. For example, the stimulation parameters may be changed in a predefined or pre-determined manner through different values for different parameters. For example, a look-up table could be used for this purpose. Alternatively, different parameters may be randomly changed to different values, for example within set ranges using a random number generator.

A further alternative is to change one or more stimulation parameters in response to detection of habituation. For example, on initial detection of habituation, one or more elements of stimulation morphology may be changed. On further detection of inadequate relief from habituation, a cueing site and/or type of stimulation (e.g., electrical or haptic) may be changed, although it will be appreciated the stimulation parameters may be changed in other ways and in a different order in response to detection of habituation.

The invention is not limited to the embodiments described but may be varied in construction and detail.

The invention claimed is:

1. A gait management apparatus comprising:
   at least one cueing actuator comprising at least one stimulation apparatus configured to be disposed at one or more cueing sites on each side of a patient's body to provide bilateral stimulation;
   a memory for storing a non-transitory computer program;
   a motion sensing system including one or more motion sensing elements, configured to detect motion of the patient; and
   a controller programmed to execute the program stored in the memory to allow the controller to activate cueing, wherein the at least one cueing actuator, the memory, and the controller are in electrical contact; and
   wherein the controller is programmed to:
   determine movement of a leg of the patient during a current stride; and
   activate cueing customized to the patient, in response to signals received from the motion sensing system, to provide stimulation to a contralateral arm of the patient, to enable a timing relationship between the movement of the contralateral arm of the patient with movement of the leg of the patient.

2. The gait management apparatus of claim 1, wherein the at least one stimulation apparatus is configured to provide electrical and/or haptic stimulation.

3. The gait management apparatus of claim 1, wherein:
   i) the controller is programmed to activate cueing based on fixed timings; and/or
   ii) the controller is programmed to activate cueing based on adaptive timings.

4. The gait management apparatus of claim 1, wherein the at least one stimulation apparatus is disposed at a plurality of cueing sites on each side of the patient's body, and optionally wherein the cueing sites are located across a plurality of body parts.

5. The gait management apparatus of claim 1, wherein the controller is programmed to:
   determine gait cycles of one or more previous strides and/or gait activity of the patient using signals received from the motion sensing system; and
   activate cueing for a current stride of the patient based on the gait cycles of the one or more previous strides and/or gait activity.

6. The gait management apparatus of claim 1, wherein the motion sensing system is configured to be disposed on an arm of the patient and/or on a leg of the patient.

7. A gait management apparatus comprising:
   at least one cueing actuator comprising at least one stimulation apparatus configured to be disposed at one or more cueing sites on each side of a patient's body to provide bilateral stimulation;
   a memory for storing a non-transitory computer program;
   a motion sensing system including one or more motion sensing elements, configured to detect motion of the patient; and
   a controller programmed to execute the program stored in the memory to allow the controller to activate cueing, wherein the at least one cueing actuator, the memory, and the controller are in electrical contact; and
   wherein the controller is programmed to:
   determine movement of an arm of the patient during a current stride; and
   activate cueing customized to the patient, in response to signals received from the motion sensing system, to provide stimulation to a contralateral leg of the patient, to enable a timing relationship between the movement of the contralateral leg of the patient with movement of the arm of the patient.

8. The gait management apparatus of claim 7, wherein the at least one stimulation apparatus is configured to provide electrical and/or haptic stimulation.

9. The gait management apparatus of claim 7, wherein:
   i) the controller is programmed to activate cueing based on fixed timings; and/or
   ii) the controller is programmed to activate cueing based on adaptive timings.

10. The gait management apparatus of claim 7, wherein the at least one stimulation apparatus is disposed at a plurality of cueing sites on each side of the patient's body, and optionally wherein the cueing sites are located across a plurality of body parts.

11. The gait management apparatus of claim 7, wherein the controller is programmed to:
   determine gait cycles of one or more previous strides and/or gait activity of the patient using signals received from the motion sensing system; and
   activate cueing for a current stride of the patient based on the gait cycles of the one or more previous strides and/or gait activity.

12. The gait management apparatus of claim 7, wherein the motion sensing system is configured to be disposed on an arm of the patient and/or on a leg of the patient.

* * * * *